US011021751B2

(12) United States Patent
Roses

(10) Patent No.: US 11,021,751 B2
(45) Date of Patent: *Jun. 1, 2021

(54) DISEASE RISK FACTORS AND METHODS OF USE

(71) Applicant: Zinfandel Pharmaceuticals, Inc., Durham, NC (US)

(72) Inventor: Allen D. Roses, Chapel Hill, NC (US)

(73) Assignee: Zinfandel Pharmaceuticals, Inc., Durham, NC (US)

( * ) Notice: Subject to any disclaimer, the term of this patent is extended or adjusted under 35 U.S.C. 154(b) by 169 days.

This patent is subject to a terminal disclaimer.

(21) Appl. No.: 16/031,218

(22) Filed: Jul. 10, 2018

(65) Prior Publication Data

US 2019/0032137 A1 Jan. 31, 2019

Related U.S. Application Data

(63) Continuation of application No. 14/464,961, filed on Aug. 21, 2014, now abandoned, which is a continuation of application No. 13/029,713, filed on Feb. 17, 2011, now Pat. No. 8,846,315, which is a continuation-in-part of application No. 13/058,724, filed as application No. PCT/US2009/053373 on Aug. 11, 2009, now Pat. No. 8,815,508.

(60) Provisional application No. 61/088,203, filed on Aug. 12, 2008, provisional application No. 61/186,673, filed on Jun. 12, 2009, provisional application No. 61/224,647, filed on Jul. 10, 2009, provisional application No. 61/431,294, filed on Jan. 10, 2011.

(51) Int. Cl.
*C12Q 1/68* (2018.01)
*C12P 19/34* (2006.01)
*C12Q 1/6883* (2018.01)
*A61K 31/4439* (2006.01)

(52) U.S. Cl.
CPC ........ *C12Q 1/6883* (2013.01); *A61K 31/4439* (2013.01); *C12Q 2600/106* (2013.01); *C12Q 2600/118* (2013.01); *C12Q 2600/156* (2013.01)

(58) Field of Classification Search
CPC ............ C12Q 1/6883; C12Q 2600/106; C12Q 2600/118; C12Q 2600/156
See application file for complete search history.

(56) References Cited

U.S. PATENT DOCUMENTS

| | | | |
|---|---|---|---|
| 4,687,777 A | 8/1987 | Meguro et al. | |
| 5,002,953 A | 3/1991 | Hindley | |
| 5,112,460 A | 5/1992 | Karger et al. | |
| 5,171,750 A | 12/1992 | Brossi et al. | |
| 5,326,770 A | 7/1994 | Wilkerson | |
| 5,508,167 A | 4/1996 | Roses et al. | |
| 5,595,883 A | 1/1997 | Appleyard et al. | |
| 5,716,828 A | 2/1998 | Roses et al. | |
| 5,716,975 A | 2/1998 | Bue-Valleskey et al. | |
| 5,811,439 A | 9/1998 | Ogawa et al. | |
| 5,904,824 A | 5/1999 | Oh | |
| 5,965,569 A | 10/1999 | Camps Garcia et al. | |
| 5,965,584 A | 10/1999 | Ikeda et al. | |
| 5,990,126 A | 11/1999 | Park et al. | |
| 6,027,896 A | 2/2000 | Roses et al. | |
| 6,191,154 B1 | 2/2001 | Landreth et al. | |
| 6,291,182 B1 | 9/2001 | Schork et al. | |
| 6,303,633 B1 | 10/2001 | Chen et al. | |
| 6,355,429 B1 | 3/2002 | Nygren et al. | |
| 6,399,639 B1 | 6/2002 | Matsui et al. | |
| 6,401,043 B1 | 6/2002 | Stanton, Jr. et al. | |
| 6,432,985 B2 | 8/2002 | Alanine et al. | |
| 6,532,467 B1 | 3/2003 | Brocklebank et al. | |
| 6,559,188 B1 | 5/2003 | Gatlin et al. | |
| 6,642,267 B2 | 11/2003 | Przewosny et al. | |
| 6,673,780 B2 | 1/2004 | Dasseux et al. | |
| 6,680,299 B2 | 1/2004 | Or et al. | |
| 6,699,910 B2 | 3/2004 | Dasseux et al. | |
| 6,703,422 B2 | 3/2004 | Dasseux et al. | |
| 6,811,988 B2 | 11/2004 | Chojkier et al. | |
| 6,828,462 B2 | 12/2004 | Henrich et al. | |
| 6,838,452 B2 | 1/2005 | Harats et al. | |
| 6,956,055 B2 | 10/2005 | Sundermann et al. | |
| 6,964,868 B1 | 11/2005 | Williams et al. | |
| 7,052,849 B2 | 5/2006 | Jackowski et al. | |
| 7,122,373 B1 | 10/2006 | Williams et al. | |

(Continued)

FOREIGN PATENT DOCUMENTS

CN 1257205 A 6/2000
CN 1753675 A 3/2006

(Continued)

OTHER PUBLICATIONS

Yu, C.-E., etal "Comprehensive analysis of APOE and selected proximate markers for late-onset Alzheimer's disease: Patterns of linkage disequilibrium and disease/marker association" Genomics 89 (2007) 655-665 (Year: 2007).*
GenBank Locus NC_000019.8, "Homo sapiens chromosome 19, reference assembly, complete sequence." Aug. 30, 2006, printed the 12,501 bp that are the region 50,086,300-50,098,800 from https://www.ncbi.nlm.nih.gov/ (Year: 2006).
Mills et al. "An initial map of insertion and deletion (INDEL) variation in the human genome" Genome Res. 16: 1182-1190 (2006).
Submitted SN P(ss) Report in Submission Format for ss 14931806, Nov. 13, 2003, Handle—local_snp_id: Devin E_LAB-INDEL_GP34_WGS_6934. one page printed from https://www.ncbi.nlm.nih.gov/projects/SNP/snp_retrieve.cgi?subsnp_id=14931806 (Year: 2003).

(Continued)

*Primary Examiner* — Stephen T Kabushoc
(74) *Attorney, Agent, or Firm* — Myers Bigel, P.A

(57) ABSTRACT

Provided herein are genetic variants associated with development of a condition of interest (e.g., Alzheimer's disease). Methods of treatment with an active agent (e.g., with a particular active agent and/or at an earlier age) is also provided, upon detecting a genetic variant described herein. In some embodiments, the genetic variant is a deletion/insertion polymorphism (DIP) of the TOMM40 gene.

10 Claims, 10 Drawing Sheets

Specification includes a Sequence Listing.

(56) References Cited

U.S. PATENT DOCUMENTS

| | | |
|---|---|---|
| 7,127,466 B2 | 10/2006 | Brocklebank et al. |
| 7,132,244 B2 | 11/2006 | Jackowski et al. |
| 7,135,297 B2 | 11/2006 | Jackowski et al. |
| 7,186,704 B2 | 3/2007 | Harats et al. |
| 7,304,093 B2 | 12/2007 | Dasseux et al. |
| 7,329,501 B2 | 2/2008 | Jackowski et al. |
| 7,504,388 B2 | 3/2009 | Harats et al. |
| 7,608,412 B2 | 10/2009 | Wooten et al. |
| 7,625,882 B2 | 12/2009 | Harats et al. |
| 7,833,513 B2 | 11/2010 | De la Monte et al. |
| 7,888,035 B2 | 2/2011 | Klass et al. |
| 7,893,291 B2 | 2/2011 | Harats et al. |
| 7,897,356 B2 | 3/2011 | Klass et al. |
| 7,902,176 B2 | 3/2011 | Harats et al. |
| 7,973,023 B2 | 7/2011 | Harats et al. |
| 8,005,623 B2 | 8/2011 | Hellerstein |
| 8,815,508 B2 | 8/2014 | Roses |
| 8,846,315 B2 | 9/2014 | Roses |
| 9,102,666 B2 | 8/2015 | Roses et al. |
| 9,724,339 B2 | 8/2017 | Roses |
| 2002/0077316 A1 | 6/2002 | Dasseux et al. |
| 2003/0022865 A1 | 1/2003 | Dasseux et al. |
| 2003/0078239 A1 | 4/2003 | Dasseux et al. |
| 2003/0096431 A1 | 5/2003 | Jackowski et al. |
| 2003/0100126 A1 | 5/2003 | Jackowski et al. |
| 2003/0220374 A1 | 11/2003 | Needleman |
| 2003/0225035 A1 | 12/2003 | Harats et al. |
| 2004/0060077 A1 | 3/2004 | Esmond et al. |
| 2004/0106677 A1 | 6/2004 | Harats et al. |
| 2004/0122091 A1 | 6/2004 | Dasseux et al. |
| 2004/0198814 A1 | 10/2004 | Dasseux et al. |
| 2004/0204502 A1 | 10/2004 | Dasseux et al. |
| 2004/0265849 A1 | 12/2004 | Cargill et al. |
| 2005/0004179 A1 | 1/2005 | Pedersen |
| 2005/0020694 A1 | 1/2005 | Dasseux et al. |
| 2005/0021236 A1 | 1/2005 | Aston et al. |
| 2005/0043242 A1 | 2/2005 | Esmond et al. |
| 2005/0272813 A1 | 12/2005 | Harats et al. |
| 2005/0277129 A1 | 12/2005 | Aerssens et al. |
| 2006/0020440 A1 | 1/2006 | Hellerstein |
| 2006/0194339 A1 | 8/2006 | Jackowski et al. |
| 2006/0205091 A1 | 9/2006 | Jackowski et al. |
| 2006/0211138 A1 | 9/2006 | Jackowski et al. |
| 2006/0211139 A1 | 9/2006 | Jackowski et al. |
| 2006/0211140 A1 | 9/2006 | Jackowski et al. |
| 2006/0211141 A1 | 9/2006 | Jackowski et al. |
| 2006/0211145 A1 | 9/2006 | Jackowski et al. |
| 2006/0211146 A1 | 9/2006 | Jackowski et al. |
| 2006/0228728 A1 | 10/2006 | Cox et al. |
| 2007/0010029 A1 | 1/2007 | Jackowski et al. |
| 2007/0099868 A1 | 5/2007 | Harats et al. |
| 2007/0105856 A1 | 5/2007 | Carpino et al. |
| 2007/0105859 A1 | 5/2007 | Isshiki et al. |
| 2007/0149615 A9 | 6/2007 | Dasseux et al. |
| 2007/0203083 A1 | 8/2007 | Mootha et al. |
| 2007/0238643 A1 | 10/2007 | Wooten et al. |
| 2008/0045582 A1 | 2/2008 | Zineh et al. |
| 2008/0051318 A1 | 2/2008 | Li et al. |
| 2008/0153088 A1 | 6/2008 | Sun et al. |
| 2008/0226719 A1 | 9/2008 | Roses et al. |
| 2008/0261865 A1 | 10/2008 | Harats et al. |
| 2008/0262047 A1 | 10/2008 | Roses et al. |
| 2008/0286876 A1 | 11/2008 | Stephanie |
| 2009/0042849 A1 | 2/2009 | Birnbaum |
| 2009/0143442 A1 | 6/2009 | Colca et al. |
| 2009/0209775 A1 | 8/2009 | Harats et al. |
| 2010/0048515 A1 | 2/2010 | Harats et al. |
| 2010/0092470 A1 | 4/2010 | Bhatt et al. |
| 2010/0105034 A1 | 4/2010 | Hutton et al. |
| 2010/0113290 A1 | 5/2010 | Klass et al. |
| 2010/0120842 A1 | 5/2010 | Barlow et al. |
| 2010/0136584 A1 | 6/2010 | Bhatt et al. |
| 2010/0184046 A1 | 7/2010 | Klass et al. |
| 2010/0203529 A1 | 8/2010 | Kuslich et al. |
| 2010/0256235 A1 | 10/2010 | Puder et al. |
| 2011/0082187 A1 | 4/2011 | Campbell et al. |
| 2011/0097350 A1 | 4/2011 | Harats et al. |
| 2011/0151460 A1 | 6/2011 | Klass et al. |
| 2011/0159506 A1 | 6/2011 | Klass et al. |
| 2011/0166185 A1 | 7/2011 | Roses |
| 2011/0189165 A1 | 8/2011 | Roses |
| 2011/0189212 A1 | 8/2011 | Harats et al. |
| 2011/0195394 A1 | 8/2011 | Selinfreund et al. |
| 2011/0195395 A1 | 8/2011 | Selinfreund et al. |
| 2011/0195396 A1 | 8/2011 | Selinfreund et al. |
| 2011/0195397 A1 | 8/2011 | Selinfreund et al. |
| 2011/0195398 A1 | 8/2011 | Selinfreund et al. |
| 2011/0195399 A1 | 8/2011 | Selinfreund et al. |
| 2011/0195400 A1 | 8/2011 | Selinfreund et al. |
| 2011/0195401 A1 | 8/2011 | Selinfreund et al. |
| 2011/0195402 A1 | 8/2011 | Selinfreund et al. |
| 2011/0195403 A1 | 8/2011 | Selinfreund et al. |
| 2011/0195404 A1 | 8/2011 | Selinfreund et al. |
| 2011/0195421 A1 | 8/2011 | Selinfreund et al. |
| 2011/0195422 A1 | 8/2011 | Selinfreund et al. |
| 2011/0195423 A1 | 8/2011 | Selinfreund et al. |
| 2011/0195424 A1 | 8/2011 | Selinfreund et al. |
| 2011/0195425 A1 | 8/2011 | Selinfreund et al. |
| 2011/0195427 A1 | 8/2011 | Selinfreund et al. |
| 2011/0195439 A1 | 8/2011 | Selinfreund et al. |
| 2011/0195440 A1 | 8/2011 | Selinfreund et al. |
| 2011/0195487 A1 | 8/2011 | Selinfreund et al. |
| 2011/0195488 A1 | 8/2011 | Selinfreund et al. |
| 2011/0195491 A1 | 8/2011 | Selinfreund et al. |
| 2011/0195508 A1 | 8/2011 | Selinfreund et al. |
| 2011/0195851 A1 | 8/2011 | Selinfreund et al. |
| 2011/0195855 A1 | 8/2011 | Selinfreund et al. |
| 2011/0195856 A1 | 8/2011 | Selinfreund et al. |
| 2011/0195857 A1 | 8/2011 | Selinfreund et al. |
| 2011/0195858 A1 | 8/2011 | Selinfreund et al. |
| 2011/0195859 A1 | 8/2011 | Selinfreund et al. |
| 2011/0195871 A1 | 8/2011 | Selinfreund et al. |
| 2011/0195872 A1 | 8/2011 | Selinfreund et al. |
| 2011/0195873 A1 | 8/2011 | Selinfreund et al. |
| 2011/0195874 A1 | 8/2011 | Selinfreund et al. |
| 2011/0196085 A1 | 8/2011 | Selinfreund et al. |
| 2011/0236317 A1 | 9/2011 | Cravo et al. |
| 2011/0237450 A1 | 9/2011 | Klass et al. |
| 2012/0184584 A1 | 7/2012 | Roses et al. |
| 2015/0073025 A1 | 3/2015 | Roses |
| 2016/0000769 A1 | 1/2016 | Roses et al. |
| 2018/0363060 A1* | 12/2018 | Roses .............. A61P 43/00 |
| 2019/0032137 A1 | 1/2019 | Roses |

FOREIGN PATENT DOCUMENTS

| | | |
|---|---|---|
| EP | 2172200 A1 | 4/2010 |
| JP | 2000-273040 A | 10/2000 |
| JP | 2001-514663 | 9/2001 |
| WO | WO 00/66102 A2 | 11/2000 |
| WO | WO 01/35941 A2 | 5/2001 |
| WO | WO 02/30860 A2 | 4/2002 |
| WO | WO 02/30882 A2 | 4/2002 |
| WO | WO 02/30884 A2 | 4/2002 |
| WO | WO 02/41827 A2 | 5/2002 |
| WO | WO 03/046001 A2 | 6/2003 |
| WO | WO 03/046005 A2 | 6/2003 |
| WO | WO 03/046573 A2 | 6/2003 |
| WO | WO 2004/005510 A1 | 1/2004 |
| WO | WO 2004/058258 A1 | 7/2004 |
| WO | WO 2004/106486 A2 | 12/2004 |
| WO | WO 2005/003766 A2 | 1/2005 |
| WO | WO 2005/047236 A1 | 5/2005 |
| WO | WO 2005/081943 A2 | 9/2005 |
| WO | WO 2006/054297 A2 | 5/2006 |
| WO | WO 2007/038112 A2 | 4/2007 |
| WO | WO 2007/038115 A2 | 4/2007 |
| WO | WO 2007/044522 A1 | 4/2007 |
| WO | WO 2007/109024 A2 | 9/2007 |
| WO | WO 2008/019187 A2 | 2/2008 |
| WO | WO 2008/036678 A2 | 3/2008 |
| WO | WO 2008/098318 A1 | 8/2008 |
| WO | WO 2008/147562 A2 | 12/2008 |
| WO | WO 2010/019550 A2 | 2/2010 |

(56) References Cited

FOREIGN PATENT DOCUMENTS

| WO | WO 2010/033913 A1 | 3/2010 |
|---|---|---|
| WO | WO 2010/053788 A1 | 5/2010 |
| WO | WO 2010/056337 A2 | 5/2010 |
| WO | WO 2010/062706 A2 | 6/2010 |
| WO | WO 2010/066901 A2 | 6/2010 |
| WO | WO 2010/100653 A2 | 9/2010 |
| WO | WO 2010/123720 A1 | 10/2010 |
| WO | WO 2011/109440 A1 | 9/2011 |
| WO | WO 2011/127219 A1 | 10/2011 |

OTHER PUBLICATIONS

Database: dbSNP [online], rs10524523, Jul. 7, 2019, [retrieved Dec. 11, 2019], https://www.ncbi.nlm.nih.gov/snp/rs10524523#submissions.
Database: dbSNP [online], Submitted SNP(ss) Details: ss81535143, Nov. 27, 2007, [retrieved Dec. 11, 2019], https://www.ncbi.nlm.nih.gov/projects/SNP/snp_ss.cgi?subsnp_id=ss81535143.
Japanese Office Action corresponding to JP2018-228465, dated Dec. 11, 2019 (9 pp, including English translation).
"AD, Risk, ApoE—Tomm40 No Tomfoolery," Alzheimer Research Forum, Nov. 15, 2009, http://www.alzforum.org/new/detailprint.asp?id=2285, 3 pages.
Abbatecola et al., "Rosiglitazone and Cognitive Stability in Older Individuals With Type 2 Diabetes and Mild Cognitive Impairment," Diabetes Care Aug. 2010, 33(8):1706-1711.
Abeid et al., "Apolipoprotein-E genotype and the risk of developing cholelithiasis following bariatric surgery: a clue to prevention of routine prophylactic cholecystectomy," Obesity Surgery, 2002, 12:354-357.
Abraham et al., "A genome-wide association study for late-onset Alzheimer's disease using DNA pooling," BMC Med Genomics, 2008, 1: 44.
Ahmad et al., "Myelin-associated Glycoprotein Protects Brain From NMDA-induced Acute Excitotoxicity: Critical Role of Myelination on Neuron Survival," Stroke, Apr. 2009, 40(4):e216-e217.
Akuffo et al., "The discovery and early validation of novel plasma biomarkers in mild-to-moderate Alzheimer's disease pateitns responding to treatment with rosiglitazone," Biomarkers, 2008, 13(6), 618-636.
Albert et al., "The diagnosis of mild cognitive impairment due to Alzheimer's disease: Recommendations from the National Institute on Aging-Alzheimer's Association workgroups on diagnostic guidelines for Alzheimer's disease," Alzheimer's & Dementia, 2011, 7:270-279.
Allen et al., "Reduced Hippocampal Functional Connectivity in Alzheimer Disease," Archives of Neurology, Oct. 2007, 64(10):1482-1487.
Andreotti et al., "Polymorphisms of genes in the lipid metabolism pathway and risk of biliary tract cancers and stones: a population-based case-control study in Shanghai, China," Cancer Epidemiol Biomarkers Prev, 2008, 17(3):525-534.
Bang et al., "Important link between dementia subtype and apolipoprotein E: a meta-analysis," Yonsei Med J, 2003, 44(3):401-413.
Bardel et al., "On the use of haplotype phylogeny to detect disease susceptibility loci," BMC Genetics, May 18, 2005, 6: 24-37.
Barnes et al. "Risk in drug trials," The Lancet, Dec. 2006, 368:2205-2206.
Baum et al., "Apolipoprotein Eϵ4 allele is associated with vascular dementia," Dement. Geriatr. Cogn. Disord., Aug. 22, 2006, 22: 301-305.
Beecham et al., "PCDH11X variation is not associated with late-onset Alzheimer disease susceptibility," Psychiatr. Genet., 2010, 20(6):321-324.
Bekris et al., "APOE mRNA and protein expression in postmortem brain are modulated by an extended haplotype structure," Am. J. Med. Genet. Part B, 2010, 153B: 409-417.
Bekris et al., "Multiple SNPs within and surrounding the apolipoprotein E gene influence cerebrospinal fluid apolipoprotein E protein levels," J. Alzheimers Dis., 2008, 13:255-266.
Bennet et al., "Association of apolipoprotein E genotypes with lipid levels and coronary risk," JAMA, Sep. 19, 2007, 298(11):1300-1311.
Bertram et al., "Systematic meta-analyses of Alzheimer disease genetic association studies: the AlzGene database," Nat. Genet., Jan. 2007, 39(1):17-23.
Birks, JS, Cholinesterase inhibitors for Alzheimer's disease (Review), Cochrane Database of Systematic Reviews, 2006, issue 1, Art. No. CD005593, 107 pages.
Blacker et al., "ApoE-4 and Age at Onset of Alzheimer's Disease: The NIMH Genetics Initiative," Neurology, 1997, 48:139-147.
Blagosklonny, Mikhail V., "Validation of anti-aging drugs by treating age-related diseases," Aging, Mar. 2009, 1(3):281-288. Electronic Publication: 2009-03-28. Ref: 107 Journal code: 101508617.
Blalock et al., "Effects of Long-Term Pioglitaozne Treatment on Peripheral and Central Markers of Aging," PLoS One, Apr. 2010, 5(4):1-14.
Bojanowski et al., "An Apolipoprotein E variant may protect against age-related macular degeneration through cytokine regulation," Environ. Mol. Mutagen., 2006, 47:594-602.
Boland et al., "Apolipoprotein E Genotype and Gallbladder Disease Risk in a Large Population-Based Cohort," Annals of Epidemiology, Oct. 2006, 16(10):763-769.
Bright et al., "PPAR Regulation of Inflammatory Signaling in CNS Diseases," PPAR Research, 2008, 658520, 12 pages.
Brodbeck et al., "Rosiglitazone increases dendritic spine density and rescues spine loss caused by apolipoprotein E4 in primary cortical neurons," Proc. Natl. Acad. Sci. USA, 2008, 105(4):1343-1346.
Brookmeyer et al., "Forecasting the global burden of Alzheimer's disease," Alzheimer's & Dementia, The Journal of the Alzheimer's Association, 2007, 3(3):186-191.
Brookmeyer et al., "Projections of Alzheimer's Disease in the United States and the Public Health Impact of Delaying Disease Onset," American Journal of Public Health, Sep. 1998, 88(9):1337-1342.
Brune et al., "Polymorphism in the peroxisome proliferator-activated receptor α gene influences the risk for Alzheimer's disease," Journal of Neural Transmission, Sep. 2003, 110(9):1041-1050.
Bruno et al., "Cerebrospinal fluid cortisol concentrations in healthy elderly are affected by both APOE and TOMM40 variants," Psychoneuroendocrinology in Press, Epub ahead of print: Jul. 30, 2011, 6 pages.
Bunsey et al., "Conservation of hippocampal memory function in rats and humans," Nature, Jan. 18, 1996, 379:255-257.
Burt et al., "Apolipoprotein (apo) E4 enhances HIV-1 cell entry in vitro, and the APOE epsilon4/epsilon4 genotype accelerates HIV disease progression," Proc. Nati. Acad. Sci. USA, Jun. 24, 2008, 105(25):8718-8723.
Cacabelos R., Chapter 10, Pharmacogenomics in Alzheimer's disease, Methods in Molecular Biology, 2008, 448:213-357.
Cacabelos, R., "Molecular Pathology and Pharmacogenomics in Alzheimer's Disease: Polygenic-related Effects of Multifactorial Treatments on Cognition, Anxiety, and Depression," Methods Find. Exp. Clin. Pharmacol., 2007, 29(SupplA):1-91.
Camacho et al., "Peroxisome Proliferator-Activated Receptor γ Induces a Clearance Mechanism for the Amyloid-$\beta^2$ Peptide," The Journal of Neuroscience, Dec. 1, 2004, 24(48):10908-10917.
Carrasquillo et al., "Genetic variation in PCDH11X is associated with susceptibility to late-onset Alzheimer's disease," Nat. Genet., Feb. 2009, 41(2):192-198.
Caselli et al., "Longitudinal modeling of age-related memory decline and the APOE ϵ4 effect," N. Engl. J. Med., Jul. 16, 2009, 361(3):255-263.
Caselli et al., "TOMM40, APOE and preclinical memory decline," Presented at International Conference on Alzheimer's Disease, Paris, France. Jul. 18, 2011, Alzheimer's and Dementia, 7: S293, O2-03-01.

(56) References Cited

OTHER PUBLICATIONS

Caselli et al., "TOMM40, APOE, and age of onset of Alzheimer's disease," Presented at International Conference on Alzheimer's Disease, Honolulu, Hawaii on Jul. 10-15. Published in *Alzheimer's and Dementia* 6: S202, P1-096, 2010.
Chang et al., "Lipid- and receptor-binding regions of apolipoprotein E4 fragments act in concert to cause mitochondrial dysfunction and neurotoxicity," Proc. Natl. Acad. Sci. USA, Dec. 20, 2005, 102(51):18694-18699.
Chiang et al., "Hippocampal atrophy rates and CSF biomarkers in elderly APOE2 normal subjects," Neurology, Nov. 30, 2010, 75(22):1978-1981.
Chu et al., "TOMM40 poly-T repeat lengths, age of onset and psychosis risk in Alzheimer disease," Neurobiology of Aging, 2011, 32:2328.e1-2328.e9, In Press, Epub ahead of print: Aug. 4, 2011.
CINAPS Compound Dossier, Pioglitazone, Dec. 22, 2009, 21 pages.
Clement et al., "TCS: a computer program to estimate gene genealogies," Mol. Ecol., 2000, 9:1657-1659.
Cogswell et al., "Identification of miRNA Changes in Alzheimer's Disease Brain and CSF Yields Putative Biomarkers and Insights into Disease Pathways," Journal of Alzheimer's Disease, May 2008, 14(1):27-41.
Collino et al., "Modulation of the oxidative stress and inflammatory response by PPAR-γ agonists in the hippocampus of rats exposed to cerebral ischemia/reperfusion," European Journal of Pharmacology, 2006, 530:70-80.
Combs et al., "Inflammatory mechanisms in Alzheimer's disease: inhibition of β-amyloid-stimulated proinflammatory responses and neurotoxicity by PPARγ agonists," Journal of Neuroscience, 2000, 20(2): 558-567.
Comment by Allen Roses http://www.alzforum.org/new/detail.asp?id=2873, Primary Papers: Association and Expression Analyses With Single-Nucleotide Polymorphisms in TOMM40 in Alzheimer Disease., Submitted Aug. 15, 2011, Posted Aug. 15, 2011.
Coon et al., "A high-density whole-genome association study reveals that APOE is the major susceptibility gene for sporadic late-onset Alzheimer's disease," J. Clin. Psychiatry, Apr. 2007, 68(4):613-618.
Corder et al., "Gene dose of apolipoprotein E type 4 allele and the risk of Alzheimer's disease in late onset families," Science, Aug. 13, 1993, 261:921-923.
Corder et al., "Protective effect of apolipoprotein E type 2 allele for late onset Alzheimer disease," Nat. Genet., Jun. 1994, 7:180-184.
Costa et al., "Multiplex allele-specific fluorescent PCR for haplotyping the IVS8 $(TG)_m(T)_n$ locus in the CFTR gene," Clin. Chem., 2008, 54(9):1564-1567.
Costello et al., "Agonists of peroxisome proliferator-activated receptor-[γ] attenuate the A[β]-mediated impairment of LTP in the hippocampus in vitro," Neuropharmacology, 2005, 49:359-366.
Crenshaw et al., "Using Genetics to Enable Studies on the Prevention of Alzheimer's Disease," Clinical Pharmacology & Therapeutics, Feb. 2013, 93(2):177-185.
Cruchaga et al. for the Alzheimer's Disease Neuroimaging Initiative, "Association and Expression Analyses With Single-Nucleotide Polymorphisms in TOMM40 in Alzheimer Disease," Arch. Neurol., Aug. 2011, 68(8):1013-1019.
Das, Undurti N., "Acetylcholinesterase and butyrylcholinesterase as possible markers of low-grade systemic inflammation," Medical Science Monitor, 2007, 13(12):RA214-RA221.
De la Monte et al., "Alzheimer's Disease Is Type 3 Diabetes-Evidence Reviewed," Journal of Diabetes Science and Technology, Nov. 2008, 2(6):1101-1113.
De la Monte et al., "Nitrosamine exposure exacerbates high fat diet-mediated type 2 diabetes mellitus, non-alcoholic steatohepatitis, and neurodegeneration with cognitive impairment," Molecular Neurodegeneration, 2009, 4:54 (pp. 1-21).
Dean et al., "Plasma apolipoprotein E is decreased in schizophrenia spectrum and bipolar disorder," Psychiatry Research, 2008, 158:75-78.

Deng et al., "Meta-analysis of the association of the LRP C766T polymorphism with the risk of Alzheimer's disease," Genetics, Dec. 31, 2006, 28(4):393-398, English abstract.
Devi et al., "Accumulation of Amyloid Precursor Protein in the Mitochondrial Import Channels of Human Alzheimer's Disease Brain is Associated with Mitochondrial Dysfunction," Journal of Neuroscience, Aug. 30, 2006, 26(35):9057-9068.
Devi et al., "Mitochondrial trafficking of APP and alpha synuclein: Relevance to mitochondrial dysfunction in Alzheimer's and Parkinson's diseases," Biochimica et Biophysica Acta (BBA)—Molecular Basis of Disease, 2010, 1802:11-19.
Doraiswamy et al., "Pharmacological strategies for the prevention of Alzheimer's disease," Expert Opinion on Pharmacotherapy, Jan. 2006, 7(1):1-10.
Dubois et al., "Research criteria for the diagnosis of Alzheimer's disease: revising the NINCDS-ADRDA criteria," Lancet Neurol., Aug. 2007, 6:734-746.
Dubois et al., "Revising the definition of Alzheimer's disease: a new lexicon," Lancet Neurol., Nov. 2010, 9:1118-1127.
Efron et al., "Bootstrap confidence levels for phylogenetic trees," Proc. Natl. Acad. Sci. USA, 1996, 93:13429-13434.
Elliott et al., "Genetic Loci associated with C-reactive protein levels and risk of coronary heart disease," JAMA, Jul. 1, 2009, 302(1):37-48.
Elosua et al., "Obesity Modulates the Association among APOE Genotype, Insulin, and Glucose in Men," Obesity Research, Dec. 2003, 11(12):1502-1508.
Escribano et al., "Rosiglitazone rescues memory impairment in Alzheimer's transgenic mice: mechanisms involving a reduced amyloid and tau pathology," Neuropsychopharmacology, 2010, 35:1593-1604.
Escribano et al., "Rosiglitazone reverses memory decline and hippocampal glucocorticoid receptor down-regulation in an Alzheimer's disease mouse model," Biochemical & Biophysical Research Communications, 2009, 379:406-410.
Farrer et al., "Effects of Age, Sex, and Ethnicity on the Association Between Apolipoprotein E Genotpye and Alzheimer Disease," JAMA, Oct. 22/29, 1997, 278(16):1349-1356.
Fu, P.C., "The Effect and Mechanism Research of Pioglitazone to the Memory Impairment of Ad Rats," Globe Thesis [online] Sep. 22, 2010 (retrieved on Sep. 4, 2012), 2 page abstract.
Gao et al., "An experimental study of pioglitazone in treating vascular dementia," Academic Journal of Xi'An Jiaotong University, Aug. 2010. 22(3):179-182.
Gemma et al., "Rosiglitazone improves contextual fear conditioning in aged rats," Neuroreport, Oct. 5, 2004, 15(14):2255-2259.
Green et al., "Presymptomatic Genetic Testing for Neurodegenerative Diseases," Virtual Mentor, Aug. 2004, 6(8):1-4.
Groman et al., "Variation in a repeat sequence determines whether a common variant of the cystic fibrosis transmembrane conductance regulator gene is pathogenic or benign," Am. J. Hum. Genet., 2004, 74(1):176-179.
Grossman et al., "Alzheimer's disease: diagnostics, prognostics and the road to prevention," EPMA Journal, Jun. 29, 2010, 1:293-303.
Grossman et al., "Alzheimer's disease: diagnostics, prognostics and the road to prevention," The EPMA Journal, 2010, 1:293-303.
Grupe et al., "Evidence for novel susceptibility genes for late-onset Alzheimer's disease from a genome-wide association study of putative functional variants," Hum. Mol. Genet., 2007, 16(8):865-873.
Gupta et al., "Polymorphism in apolipoprotein E among migraineurs and tension-type headache subjects," J. Headache Pain, 2009, 10:115-120.
Hahn et al., "Population genetic and phylogenetic evidence for positive selection on regulatory mutations at the factor VII locus in humans," Genetics, Jun. 2004, 167:867-877.
Haines et al., "Whole-genome SNP linkage screen for dementia in the midwestern U.S. Amish," Alzheimer's and Dementia, 2008, 4: T586-T587, P3-225.
Hanyu et al., "The role of tumor necrosis factor-alpha in cognitive improvement after peroxisome proliferator-activator receptor gamma

(56) References Cited

OTHER PUBLICATIONS agonist pioglitazone treatment in Alzheimer's disease," Journal of the American Geriatrics Society, vol. 58, No. 5, 1000-1001, May 2010.
Hanyu et al., "Alzheimer's Disease," Nihon Rinsho, Feb. 2010, 68(2):330-334 (article in Japanese).
Hanyu et al., "Pioglitazone Improved Cognition in a Pilot Study on Patients with Alzheimer's Disease and Mild Cognitive Impairment with Diabetes Mellitus," J. Am. Geriart. Soc., Jan. 2009, 57(1):177-179.
Harikumar et al., "Resveratrol, A multitargeted agent for age-associated chronic diseases," Cell Cycle, Apr. 15, 2008, 7(8):1020-1035.
Harold et al., "Genome-wide association study identifies variants at CLU and PICALM associated with Alzheimer's disease," Nature Genetics, Oct. 2009, 41:1088-1093.
Harvie et al., "The effects of intermittent or continuous energy restriction on weight loss and metabolic disease risk markers: a randomized trial in young overweight women," International Journal of Obesity, May 2011, 35(5):714-727.
Hayden et al., "TOMM40 "523" Genotype Affects Age of Alzheimer's Disease Onset Differentially by Race," Presented at International Conference on Alzheimer's Disease, Paris, France. Alzheimer's and Dementia, 2011, 7:S186, p. 1-235.
Hegele, Robert A., "SNP Judgments and Freedom of Association," Arterioscler. Thromb. Vasc. Biol., 2002, 22;1058-1061.
Heneka et al., "Acute treatment with the PPARγ agonist pioglitazone and ibuprofen reduces glial inflammation and Aβ1-42 levels in APPV717I transgenic mice," Brain, 2005, 128:1442-1453.
Heneka et al., "Peroxisome proliferator-activated receptor-γ ligands reduce neuronal inducible nitric oxide synthase expression and cell death in vivo," [Erratum appears in J Neurosci Nov. 15, 2000;20(22)1 a] Journal of Neuroscience, Sep. 15, 2000, 20(18):6862-6867.
Hermann et al., "Current and Emerging Drug Treatment Options for Alzheimer's Disease," Drugs, 2011, 71(15):2031-2065.
Huang et al., "APOE-ε2 allele associated with higher prevalence of sporadic Parkinson disease," Neurology, 2004, 62:2198-2202.
Huang et al., "Apolipoprotein E and dementia in Parkinson disease: a meta-analysis," Arch. Neurol., Feb. 2006, 63:189-193.
Hubacek et al., "Apolipoprotein E Polymorphism in Hemodialyzed Patients and Healthy Controls," Biochemical Genetics, 2009, 47:688-693.
Humphries et al., "Dissection of the Mitochondrial Import and Assembly Pathway for Human Tom40," J. Biol Chem., Mar. 25, 2005, 280(12):11535-11543.
Hurley et al., "Strength Training as a Countermeasure to Aging Muscle and Chronic Disease," Sports Medicine, Apr. 1, 2011, 41(4):289-306.
Inestrosa et al., "Peroxisome proliferator-activated receptor γ is expressed in hippocampal neurons and its activation prevents β-amyloid neurodegeneration: role of Wnt signaling," Experimental Cell Research, 2005, 304:91-104.
International Search Report and Written Opinion dated Apr. 22, 2011, in corresponding PCT/US2011/24251, 12 pages.
International Search Report and Written Opinion dated Feb. 23, 2010, in PCT/US2009/053373, 15 pages.
James et al., "Pharmacogenomic effects of apolipoprotein E on intracerebral hemorrhage," Stroke, 2009, 40:632-639.
Johnson et al., "A comparative study of five technologically diverse CFTR testing platforms," J. Mol. Diagn., Jul. 2007, 9(3): 401-407.
Johnson et al., "The Effect of TOMM40 Poly-T length on Gray Matter Volume and Cognition in Middle-Aged Persons with APOE ε3/ε3 Genotype," Alzheimer's and Dementia, 2011, 7:456-465.
Johnson et al., "Tomm40 Is Associated With Gray Matter Volume In Middle-aged Persons With Apoe ε3/ε3 Genotype," Presented at International Conference of Alzheimer's disease, Honolulu, Hawaii. Alzheimer's and Dementia, 6: e16, O4-03-04.
Jueppner, H., "Functional Properties of the PTH/PTHrP Receptor," Bone, Aug. 1995, 17(2)Supplement:39S-425.

Kampman et al., "Apolipoprotein E polymorphism is associated with age of onset in schizophrenia," J. Hum. Genet., 2004, 49:355-359.
Kaur et al., "Exploring mechanism of pioglitazone-induced memory restorative effect in experimental dementia," Fundamental & Clinical Pharmacology, 2009 23:557-566.
Kenter et al., "Establishing risk of human experimentation with drugs: lessons from TGN1412," The Lancet, Oct. 14, 2006, 368:1387-1391.
Khachaturian et al., "Developing a national strategy to prevent dementia: Leon Thal Symposium 2009," Alzheimer's and Dementia, 2010, 6:89-97.
Khachaturian et al., "Creating a transatlantic research enterprise for preventing Alzheimer's disease," Alzheimer's & Dementia, The Journal of the Alzheimer's Association, 2009, 5(4):361-366.
Kobler et al., "Identification of an 11T allele in the polypyrimidine tract of intron 8 of the CFTR gene," Genet. Med., Feb. 2006, 8(2):125-128.
Koutsis et al., "APOE genotypes in Greek multiple sclerosis patients: no effect on the MS Severity Score," J. Neurol., 2007, 254:394-395.
Kumar et al., "Beneficial effects of pioglitazone on cognitive impairment in MPTP model of Parkinson's disease," Behavioural Brain Research, 2009, 197:398-403.
Label Actos-Pioglitazone FDA 1999. 42 pages.
Lai et al., "A 4-Mb high-density single nucleotide polymorphism-based map around human APOE," Genomics, 1998, 54:31-38.
Lambert et al., "Genome-wide association study identifies variants at CLU and CR1 associated with Alzheimer's disease," Nat. Genet., Oct. 2009, 41(10):1094-1099.
Landreth et al., "PPARγ Agonists as Therapeutics for the Treatment of Alzheimer's Disease," Neurotherepeutics, Jul. 2008, 5(3):481-489.
Landreth G, "PPARγ agonists as new therapeutic agents for the treatment of Alzheimer's disease," Experimental Neurology, 2006, 199:245-248.
Landreth, G., "Therapeutic use of agonists of the nuclear receptor PPARgamma in Alzheimer's disease," Curr. Alzheimer Res., Apr. 2007, 4(2):159-164, abstract.
Langer, Robert, "Drug delivery and targeting," Nature, Apr. 30, 1998, 392(Supp):5-10.
Larkin et al., "Clustal W and Clustal X version 2.0," Bioinformatics, 2007, 23(21): 2947-2948.
Leiva et al., "Relationship between Apolipoprotein E polymorphism and nephropathy in type-2 diabetic patients," Diabetes Res. Clin. Pract., 2007, 78:196-201.
Lencel et al., "Inflammaging: The driving force in osteoporosis?" Medical Hypotheses, Mar. 2011, 76(3):317-321.
Lescai et al., "An APOE Haplotype Associated with Decreased ε4 Expression Increases the Risk of Late Onset Alzheimer's Disease," Journal of Alzheimer's Disease, 2011, 24:235-245.
Lewis et al., "Methodological problems in genetic association studies of longevity—the apolipoprotein E gene as an example," Int. J. Epidemiol., 2004, 33:962-970.
Li et al., "Candidate single-nucleotide polymorphisms from a genomewide association study of Alzheimer disease," Arch. Neurol., 2008, 65(1):45-53.
Li et al., "Infection induces a positive acute phase apolipoprotein E response from a negative acute phase gene: role of hepatic LDL receptors," J. Lipid Res., 2008, 49:1782-1793.
Librado et al., "DnaSP v5: a software for comprehensive analysis of DNA polymorphism data," Bioinformatics, 2009, 25(11):1451-1452.
Linnertz, Colton et al., "Characterization of the Poly-T Variant in the TOMM40 Gene in Diverse Pupulations," PLOS One, Feb. 16, 2012, 7(2):e30994, 6 pages.
Liu et al., "Effect of pioglitazone on insulin resistance in fructose-drinking rats correlates with AGEs/RAGE inhibition and block of NAPDH oxidase and NF kappa B activation," European Journal of Pharmacology, 2010, 629:153-158.
Lo et al., "Modulating effect of apolipoprotein E polymorphisms on secondary brain insult and outcome after childhood brain trauma," Childs Nerv. Syst., 2009, 25:47-54.

(56) References Cited

OTHER PUBLICATIONS

Lutz et al., "Frequencies of the Alzheimer's disease associated TOMM40 polyT allele in different ethnic groups," Presented at The American Society of Human Genetics 60th Annual Meeting, Washington, DC on Nov. 3, 2010, 1 page poster.
Lutz et al., "Genetic variation at a single locus and age of onset for Alzheimer's disease," Alzheimer's and Dementia, 2010, 6: 125-131.
Lutz et al., "The importance of being connected," J. Alzheimers Dis., 2011, 24:247-251.
Mahley et al. "Apolipoprotein E4: a causative factor and therapeutic target in neuropathology, including Alzheimer's disease," Proc. Natl. Acad. Sci. USA, 2006, 103(15):5644-5651.
Majima et al., "Safety and Efficacy of Low-dose Pioglitazone (7.5 mg/day) vs. Standard-dose Pioglitazone (15 mg/day) in Japanese Women with Type 2 Diabetes Mellitus," Endocrine Journal, 2006, 53(3):325-330.
Martin et al., "Analysis of Association at Single Nucleotide Polymorphisms in the APOE Region," Genomics, 2000, 63:7-12.
Martin et al., "SNPing Away at Complex Diseases: Analysis of Single-Nucleotide Polymorphisms around APOE in Alzheimer Disease," The American Journal of Human Genetics, 2000, 67:383-394.
Martinez et al., "Apolipoprotein E4 is probably responsible for the chromosome 19 linkage peak for Parkinson's disease," Am. J. Med. Genet. B Neuropsychiatr. Genet., 2005, 136B: 72-74.
Masterman et al., "The telltale scan: APOE $\epsilon$4 in multiple sclerosis," Lancet Neurology, Jun. 2004, 3:331.
Miglio et al., "PPAR$\gamma$ stimulation promotes mitochondrial biogenesis and prevents glucose deprivation-induced neuronal cell loss," Neurochemistry International, 2009, 55:496-504.
Miglio et al., "PPAR$\gamma$ stimulation promotes neurite outgrowth in SH-SY5Y human neuroblastoma cells," Neuroscience Letters, 2009, 454:134-138.
Morales-Garcia et al., "Peroxisome proliferator-activated receptor $\gamma$ ligands regulate neural stem cell proliferation and differentiation in vitro and in vivo," GLIA, 2011, 59:293-307.
Moreno et al., "The Apolipoprotein E Gene Promoter (-219G/T) Polymorphism Determines Insulin Sensitivity in Response to Dietary Fat in Healthy Young Adults," J. Nutr., 2005, 135:2535-2540.
Morine et al., "Bi-directional gene set enrichment and canonical correlation analysis identify key diet-sensitive pathways and biomarkers of metabolic syndrome," BMC Bioinformatics, 2010, 11:499 (pp. 1-13).
Myllykangas et al., "APOE $\epsilon$3-haplotype modulates Alzheimer $\beta$-amyloid deposition in the brain," American Journal of Medical Genetics, 2002, 114:288-291.
Nicodemus et al., "Comprehensive association analysis of APOE regulatory region polymorphisms in Alzheimer disease," Neurogenetics, 2004, 5:201-208.
Nicolakakis et al., "Complete Rescue of Cerebrovascular Function in Aged Alzheimer's Disease Transgenic Mice by Antioxidants and Pioglitazone, a Peroxisome Proliferator-Activated Receptor $\gamma$-Activated," The Journal of Neuroscience, Sep. 10, 2008, 28(37):9287-9296.
Nicolakakis et al., "Intact memory in TGF-$\beta$1 transgenic mice featuring chronic cerebrovascular deficit: recovery with pioglitazone," J. Cereb. Blood Flow Metab., 2011, 31:200-211.
Norata et al., "Effects of PCSK9 variants on common carotid artery intima media thickness and relation to ApoE alleles," Atherosclerosis, 2010 [Epub Jun. 27, 2009], 208: 177-182.
North et al., "Further investigation of linkage disequilibrium SNPs and their ability to identify associated susceptibility loci," Ann. Hum. Genet., 2004, 68:240-248.
Notice of Oppositions dated Oct. 15, 2014, in Chilean Patent Application No. 1947-2013, and Oppositions filed by Laboratorios Andromaco S.A. and Laboratorios Recalcine S.A.
Oda et al., "Apolipoprotein E polymorphism and renal disease," Kidney Int. Suppl., 1999, 71:S25-S27.
O'Keefe et al., "Alcohol and Cardiovascular Health," Journal of the American College of Cardiology, Sep. 11, 2007, 50(11):1009-1014.

Paternoster et al., "Association between apolipoprotein E genotype and carotid intima-media thickness may suggest a specific effect on large artery atherothrombotic stroke," Stroke, 2008, 39:48-54.
Pathan et al., "Chronic administration of pioglitazone attenuates intracerebroventricular streptozotocin induced-memory impairment in rats," Life Sci., 2006, 79:2209-2216.
Peck et al., "The genetics of primary haemorrhagic stroke, subarachnoid haemorrhage and ruptured intracranial aneurysms in adults," PLoS One, Nov. 2008, 3(11):e3691, 1-12.
Pedersen et al., "Rosiglitazone attenuates learning and memory deficits in Tg2576 Alzheimer mice," Experimental Neurology, 2006, 199:265-273.
Pericak-Vance et al., "Linkage studies in familial Alzheimer disease: evidence for chromosome 19 linkage," Am. J. Hum. Genet., 1991, 48:1034-1050.
Pomara et al., "TOMM40 poly-T Variants and Cerebrospinal Fluid Amyloid Beta Levels in the Elderly," Neurochem. Res., 2011, 36:1124-1128.
Pomara et al., "Translocase of Outer Mitochondrial Membrane 40 Homolog (TOMM40) Poly-T Length Modulates Lorazepam-Related Cognitive Toxicity in Healthy APOE e4-Negative Elderly," Journal of Clinical Psychopharmacology, 2011, 31:544-546.
Ponce-Lopez et al., "Lithium, phenserine, memantine and pioglitazone reverse memory deficit and restore phosphor-GSK3$\beta$ decreased in hippocampus in intracerebroventricular streptozotocin induced memory deficit model," Brain Research, Oct. 1, 2011, 1426:73-85.
Potkin et al., "Hippocampal atrophy as a quantitative trait in a genome-wide association study identifying novel susceptibility genes for Alzheimer's disease," PLoS ONE, Aug. 2009, 4(8):e6501,1-15.
Rabiner et al., "Effects of 12 months of treatment with the PPAR$\gamma$ agonist rosiglitazone on brain glucose metabolism in Alzheimer's Disease: A 18F-FDG PET study," Presented at Alzheimer's Association International Conference on Alzheimer's Disease, Published in Alzheimers & Dementia 5: P207, p. 1-112.
Rannala et al. "Using linked markers to infer the age of a mutation," Hum. Mutat., 2001, 18(2):87-100.
Rasgon et al., "Insulin resistance and hippocampal volume in women at risk for Alzheimer's disease," Neurobiology of Aging, Nov. 2011, 32(11):1942-1948.
Reference SNP (refSNP) cluster report: rs10524523, printed on Apr. 10, 2013 from www.ncbi.nlm.nih.gov, 2 pages.
RefSNP Cluster Report rs10524523 [online] Jan. 24, 2006, 2 pages.
RefSNP Cluster Report rs10602329 [online] May 6, 2008, 2 pages.
Risner et al., "Efficacy of rosiglitazone in a genetically defined population with mild-to-moderate Alzheimer's disease," Pharmacogenomics J., 2006, 6(4):246-254.
Rodriguez-Rivera et al., "Rosiglitazone reversal of Tg2576 cognitive deficits is independent of peripheral gluco-regulatory status," Behavioural Brain Research, 2011, 216:255-261.
Roses AD et al., "Haplotypes Within The APOE LD Region May Have Pharmacogenetic Effects Predicting Efficacy of Alzheimer's Patients Receiving Rosiglitazone," Presented at IX International Meeting on Human Genome Variation and Complex Genome Analysis, Barcelona, Spain, Sep. 7, 2007.
Roses AD, "Alzheimer's disease—what is upstream from the amyloid cascade? Whole genome insights into new targets for therapy," Genome Medicine Seminar, Duke University, Jan. 2, 2008.
Roses AD, "NIA Workshop: The Role of ApoE and normal brain aging and Alzheimer's disease: Genetic basis for an APOE4-independent susceptibility locus related to mitochondrial metabolism," Aug. 13, 2008, 35 pages.
Roses AD, "On the discovery of the genetic association of Apolipoprotein E genotypes and common late-onset Alzheimer disease," Journal of Alzheimer's Disease, 2006, 9:361-366.
Roses et al., "A TOMM40 variable-length polymorphism predicts the age of late-onset Alzheimer's disease," The Pharmacogenomics Journal, 2010 (published online Dec. 22, 2009), 10:375-384.
Roses et al., "APOE$\epsilon$3 and Tomm-40 Haplotypes Determine Inheritance of Alzheimer's Disease Independently of APOE$\epsilon$4 Risk," Presented at International Conference on Alzheimer's Disease, Vienna, Austria on Sunday, Jul. 12, 2009, 3:00 PM-3:15 PM Published in Alzheimer's & Dementia 5: e1, O1-06-01.

(56) References Cited

OTHER PUBLICATIONS

Roses et al., "Cis-acting human ApoE tissue expression element is associated with human pattern of intraneuronal ApoE in transgenic mice," Neurobiol. of Aging, 1998, 19(1S):S53-S58.
Roses et al., "Complex disease-associated pharmacogenetics: drug efficacy, drug safety, and confirmation of a pathogenetic hypothesis (Alzheimer's disease)," Pharmacogenomics Journal, 2007, 7(1):10-28.
Roses et al., "New applications of disease genetics and pharmacogenetics to drug development," Current Opinion in Pharmacology, 2014, 14:81-89.
Roses et al., "TOMM40 "523" polyT allele frequencies in different ethnic groups," Presented at International Conference on Alzheimer's Disease, Honolulu, Hawaii on Jul. 10-15. Published in Alzheimer's and Dementia 4: e41, p. 4-067.
Roses, Allen D., "The Medical and Economic Roles of Pipeline Pharmacogenetics: Alzheimer's Disease as a Model of Efficacy and HLA-B*5701 as a Model of Safety," Neuropsychopharmacology, 2009, 34(1):6-17.
Roses, Allen D., M.D., "An Inherited Variable Poly-T Repeat Genotype in TOMM40 in Alzheimer Disease," Archives of Neurology, May 2010, 67(5):536-541.
Salam et al., "Novel PPAR-γ agonists identified from a natural product library: a virtual screening, induced-fit docking and biological assay study," Chem. Biol. Drug Des., 2008, 71(1):57-70.
Sanderson MJ, "Phylogenetic signal in the eukaryotic tree of life," Science, Jul. 4, 2008, 321:121-123.
Sato et al., "Efficacy of PPAR-γ agonist pioglitazone in mild Alzheimer disease," Neurobiology of Aging, 2011, epub Nov. 17, 2009, 32:1626-1633.
Saunders et al., "Association of apolipoprotein E allele e4 with late-onset familial and sporadic Alzheimer's disease," Neurology, Aug. 1993, 43:1467-1472.
Schapira AH, "Mitochondrial disease," Lancet, Jul. 1, 2006, 368(9529):70-82.
Schellenberg GD, "Genetic dissection of Alzheimer disease, a heterogeneous disorder," Proc. Natl. Acad. Sci. USA, Sep. 1995, 92(19):8552-8559.
Schmitz et al., "Robust association of the APOE e4 allele with premature myocardial infarction especially in patients without hypercholesterolaemia: the Aachen study," European Journal of Clinical Investigation, 2007, 37:106-108.
Seltman et al., "Evolutionary-based association analysis using haplotype data," Genet. Epidemiol., 2003, 25(1):48-58.
Shadlen et al., "Research agenda for understanding Alzheimer disease in diverse populations: work group on cultural diversity, Alzheimer's association," Alzheimer Dis. Assoc. Disord., 2002, 16(Suppl2):S96-S100.
Shankaran et al., "Measurement of Brain Microglial Proliferation Rates In Vivo: A Biomarker for Discovering Novel Anti-Neoruinflammatory Agents," FASEB Journal, Mar. 6 2006, 20(4, Part 1):A686-A687, 435.2. Meeting Info.: Experimental Biology 2006 Meeting. San Francisco, CA, USA. Apr. 1-5, 2006.
Sheline et al., "APOE4 Allele Disrupts Resting State fMRI Connectivity in the Absence of Amyloid Plaques or Decreased CSF Aβ42," The Journal of Neuroscience, Dec. 15, 2010, 30(50):17035-17040.
Shen et al., "Whole genome association study of brain-wide imaging phenotypes for identifying quantitative trait loci in MCI and AD: A study of the ADNI cohort," NeuroImage, 2010, 1051-1063.
Stone et al., "ApoE genotyping as a progression-rate biomarker in phase II disease-modification trials for Alzheimer's disease," Pharmacogenomics Journal, 2010, 10(3):161-164.
Sun et al., "Genetic variability in inflammation pathways and prostate cancer risk," Urol. Oncol., 2007, 25(3):250-259.
Sun et al., "Interactions of sequence variants in interleukin-1 receptor-associated kinase4 and the toll-like receptor 6-1-10 gene cluster increase prostate cancer risk," Cancer Epidemiol. Biomarkers Prev., Mar. 2006, 15(3):480-485.
Sun et al., "Sequence variants in Toll-like receptor gene cluster (TLR6-TLR1-TLR10) and prostate cancer risk," J. Natl. Cancer Inst., Apr. 6, 2005, 97(7):525-532.
Takei et al., "Genetic association study on in and around the APOE in late-onset Alzheimer disease in Japanese," Genomics, 2009, 93(5):441-448.
Templeton et al., "Tree Scanning: A Method for Using Haplotype Trees in Phenotype/Genotype Association Studies," Genetics, Jan. 2005, 169:441-453.
Tsukuda et al., "Cognitive Deficit in Amyloid-β-Injected Mice Was Improved by Pretreatment with a Low Dose of Telmisartan Party Because of Peroxisome Proliferator-Activated Receptor-γ Activation," Hypertension, Oct. 2009, 54(4):782-787.
Tzeng JY, "Evolutionary-based grouping of haplotypes in association analysis," Genet. Epidemiol., 2005, 28(3):220-231.
Tzimopoulou et al., "A Multi-Center Randomized Proof-of-Concept Clinical Trial Applying [$^{18}$F]FDG-PET for Evaluation of Metabolic Therapy with Rosiglitazone XR in Mild to Moderate Alzheimer's Disease," Journal of Alzheimer's Disease, 2010, 22:1241-1256.
Vellas et al., "Endpoints for trials in Alzheimer's disease: a European task force consensus," Lancet Neurol., May 2008, 7:436-450.
Wada et al., "Peroxisome Proliferator-activated Receptor γ-mediated Regulation of Neural Stem Cell Proliferation and Differentiation," Journal of Biological Chemistry, May 5, 2006, 281(18):12673-12681.
Wallace DC, "Mitochondrial diseases in man and mouse," Science, Mar. 5, 1999, 283(5407):1482-1488.
Waring et al., "Genome-wide association studies in Alzheimer disease," Arch. Neruol., Mar. 2008, 65(3):329-334.
Washida et al., "Nonhypotensive Dose of Telmisartan Attenuates Cognitive Impairment Partially Due to Peroxisome Proliferator-Activated Receptor-γ Activation in Mice With Chronic Cerebral Hypoperfusion," Stroke, Aug. 2010, 41(8):1798-1806.
Watson et al., "Insulin resistance, inflammation, and cognition in Alzheimer's Disease: Lessons for multiple sclerosis," Journal of the Neurological Sciences, Jun. 15, 2006, 245(1-2):21-33.
Watson et al., "Pioglitazone modulates plasma levels of β-amyloid in glucose intolerant older adults," Alzheimer's and Dementia, 2007, 3: S164, p. 206.
Watson et al., "Preserved Cognition in Patients with Early Alzheimer Disease and Amnestic Mild Cognitive Impairment During Treatment With Rosiglitazone," The American Journal of Geriatric Psychiatry, Nov. 2005, 13(11):950-958.
Watson et al., "The Role of Insulin Resistance in the Pathogenesis of Alzheimer's Disease: Implications for Treatment," CNS Drugs, 2003, 17(1): 27-45.
Welsh, EM [Editor]. (2006) Frontiers in Alzheimer's Disease Research, Table of Contents, Publisher: Nova Science Publishers, Inc.
Wijsman et al., "Genome-Wide Association of Familial Late-Onset Alzheimer's Disease Replicates BIN1 and CLU and Nominates CUGBP2 in Interaction with APOE," PLoS Genet., 2011, 7(2): e1001308, 1-19.
Winkler et al., "Oligonucleotide conjugates for therapeutic applications," Ther. Deliv., Jul. 2013, 4(7):791-809.
World Alzheimer Report 2009, Alzheimer's Disease International, Prince M and Jackson J, eds., pp. 1-93.
Yu et al., "Comprehensive Analysis of APOE and Selected Proximate Markers for Late-onset Alzheimer Disease: Pattern of Linkage Disequilibrium and Disease/Marker Association," Genomics, Jun. 2007, 89(6):655-665.
Zhang et al., "Mining biomarkers in human sera using proteomic tools," Proteomics, Jan. 2004, 4(1):244-256.
Zhou et al., "Aberrant Functional Connectivity Architecture in Alzheimer's Disease and Mild Cognitive Impairment: A Whole-Brain, Data-Driven Analysis," BioMed Research International, 2015, Article ID 495375, 9 pages.
Office Action from the Israel Patent Office corresponding to Israel Patent Application No. 239277, dated Sep. 24, 2019 (4 pages to include English translation).
Japanese Office Action corresponding to JP 2018-228465; dated Jul. 31, 2020 (8 pages, including English translation).

\* cited by examiner

| ID | APOE | CLADE | VARIANTS | | | | | | | | | | | | | | |
|---|---|---|---|---|---|---|---|---|---|---|---|---|---|---|---|---|---|
| | | | g | - | C | t | A | A | t | g | c | g | c | A | g | g | |
| 07_17 | 3/3 | B | . | . | . | . | . | . | . | . | . | . | . | . | . | . | |
| 07_54 | 3/3 | B | . | . | . | . | . | . | . | . | . | . | . | . | . | . | |
| 07_07 | 3/3 | B | . | . | . | . | . | . | . | . | . | . | . | . | . | . | |
| 95_21 | 3/3 | B | . | . | . | . | . | . | . | . | . | . | . | . | . | . | |
| 96_13 | 3/3 | B | . | . | . | . | . | . | . | . | . | . | . | . | . | . | |
| 07_29 | 2/4 | B | a | - | - | c | - | - | . | . | . | . | . | . | . | . | |
| 06_11 | 2/4 | A | a | T | T | c | T | - | c | a | t | a | g | G | t | c | |
| 07_29 | 2/4 | A | a | T | T | c | T | T | c | a | t | . | a | G | t | c | |
| 02_41 | 2/4 | A | a | T | T | c | T | T | c | a | t | . | a | G | t | c | |
| 06_11 | 2/3 | A | a | T | T | c | T | T | c | a | t | . | a | G | t | c | |
| 89_294 | 2/3 | A | a | T | T | c | T | T | T | a | t | a | a | G | t | c | |
| 07_03 | 3/3 | A | a | T | T | c | T | T | T | a | t | a | a | G | t | c | |
| 98_32 | 3/3 | A | a | T | T | c | T | T | c | a | t | a | a | G | t | c | |
| 93_022 | 3/3 | A | a | T | T | c | T | T | c | a | t | a | a | G | t | c | |
| 90_218 | 3/3 | A | a | T | T | c | - | - | c | a | t | a | a | G | t | c | |
| 89_294 | 2/3 | A | a | T | T | c | T | T | c | a | t | a | a | G | t | c | |
| 96_44 | 3/3 | A | a | T | T | c | T | T | T | a | t | a | a | G | t | c | |
| 94_27 | 3/3 | A | a | C | T | c | T | T | c | a | t | a | a | G | t | c | |
| 95_21 | 3/3 | A | a | C | T | c | T | T | c | a | t | a | a | G | t | c | |

CLADE B (columns left of center), CLADE A (columns right)

FIG. 7A

DISEASE RISK FACTORS AND METHODS OF USE

RELATED APPLICATIONS

This application is a Continuation of U.S. application Ser. No. 13/029,713, filed Feb. 17, 2011, which claims priority under 35 U.S.C. § 119(e) to provisional patent application No. 61/431,294, filed Jan. 10, 2011, the disclosure of which is incorporated by reference herein in its entirety.

This application is a Continuation of U.S. application Ser. No. 13/029,713, filed Feb. 17, 2011, which application also claims priority to and is a continuation-in-part of U.S. application Ser. No. 13/058,724, which is the U.S. National Phase Application under 35 U.S.C. § 371 of PCT Patent Application No. PCT/US2009/053373, filed Aug. 11, 2009, and published on Feb. 18, 2010, as WO 2010/019550, which application claims priority to U.S. Provisional Application No. 61/088,203, filed Aug. 12, 2008; U.S. Provisional Application No. 61/186,673, filed Jun. 12, 2009; and U.S. Provisional Application No. 61/224,647, filed Jul. 10, 2009, the disclosures of each of which is incorporated by reference herein in its entirety.

FIELD OF THE INVENTION

The present invention relates to the field of genomics, genetics, pharmacogenetics, and bioinformatics, including genome analysis and the study of DNA sequence variation. The invention also relates to studies of association between variations in DNA sequences and anticipation of an individual's susceptibility to a particular disease, disorder, or condition and/or response to or suitability for a particular drug or treatment.

BACKGROUND

The search for genetic markers associated with complex diseases is ongoing. Genome-wide scanning studies with SNP arrays continue to highlight the APOE region as the most important area for investigation in the study of Alzheimer's disease (Coon et al., J. Clin. Psychiatry 68: 613-8 (2007); Li et al., Arch. Neurol. 65: 45-53 (2007)).

The APOE 4 isoform has previously been strongly associated with increased risk of developing late-onset Alzheimer's disease. (Pericak-Vance et al., Am. J. Hum. Genet. 48, 1034-50 (1991); Martin et al., 2000, U.S. Pat. No. 6,027,896 to Roses, et al., U.S. Pat. No. 5,716,828 to Roses et al.). The relationship is dose dependent (Yoshizawa et al., 1994; Schellenberg, 1995). That is to say, a carrier of two APOE 4 alleles is more likely to develop late-onset Alzheimer's disease (LOAD) than a carrier of only one APOE 4 allele, and at an earlier age (Corder et al., Science 261, 921-3 (1993)).

Nevertheless, E4 alleles only account for roughly 50% of the inherited risk for late onset Alzheimer's disease. One explanation is that APOE 4 is merely serving as a surrogate marker for something in linkage disequilibrium nearby. Alternatively, considering the recent discovery of a mechanistic role for ApoE 4 in mitochondrial toxicity, the negative effects of APOE 4 may be abrogated or exacerbated by another gene product encoded nearby (Chang et al., 2005).

As APOE status is also associated with risk for coronary artery disease and likely also a host of other diseases and disorders, the implications of the study of the APOE region are not limited to Alzheimer's disease, but are potentially far-reaching (Mahley et al., Proc. Natl. Acad. Sci. USA 103: 5644-51 (2006)). More broadly, the examination of variant sequences for processes or pathways surrounding genes in linkage disequilibrium with other genetic regions known to be involved in complex disease processes will provide valuable information in deciphering the mechanisms of those diseases.

SUMMARY OF THE INVENTION

Provided herein are methods of determining risk for the development of Alzheimer's disease in a subject, including in some embodiment: (a) detecting from a biological sample containing deoxyribonucleic acid taken from said subject a genetic variant of the TOMM40 gene associated with increased or decreased risk of Alzheimer's disease, wherein the variant is rs10524523, and wherein the detecting comprises determining a poly-T length thereof; and/or (b) determining whether the subject is at increased or decreased risk of the development of Alzheimer's disease based upon said poly-T length.

In some embodiments, the method further comprises determining the age of the subject. In some embodiments, the method further comprises determining the APOE genotype of the subject. In some embodiments, the age and/or APOE genotype of the subject may also be use in determining whether the subject is at increased or decreased risk of the development of Alzheimer's disease in conjunction with the poly-T length.

In some embodiments, a poly-T length of at least 19 indicates increased risk of the development of Alzheimer's disease. In some embodiments, a poly-T length of at least 26 indicates increased risk of the development of Alzheimer's disease. In some embodiments, a poly-T length of at least 30 indicates increased risk of the development of Alzheimer's disease.

In some embodiments, the detecting step includes determining a poly-T length of each rs10524523 allele of the TOMM40 gene in said subject.

In some embodiments, the method further includes the step of: (c) administering an active agent to said subject in a treatment effective amount when said subject is determined to be at increased risk of Alzheimer's disease. In some embodiments, the agent is administered in an amount effective to delay the onset of Alzheimer's disease or a symptom thereof.

In some embodiments, the administering step is carried out in said subject at an earlier age when the subject is determined to be at increased risk by the presence of a poly-T length of at least 19, as compared to a subject in which said poly-T length of at least 19 is not present (e.g., beginning at age 45, 46, 47, 48, 49, 50, 51, 52, or 53, and continuously through each year thereafter, rather than beginning at age 55 or more; at age 50, 51, 52, 53, 54, 55, 56, 57, or 58, and continuously through each year thereafter, rather than beginning at age 60 or more; at age 55, 56, 57, 58, 59, 60, 61, 62, or 63, and continuously through each year thereafter, rather than beginning at age 65 or more; and at age 60, 61, 62, 63, 64, 65, 66, 67, or 68, and continuously through each year thereafter, rather than beginning at age 70 or more).

In some embodiments, the active agent is a peroxisome proliferator-activated receptor agonist or modulator, for example, pioglitazone or a pharmaceutically acceptable salt thereof.

Also provided is a method of treating a subject for Alzheimer's disease by administering an active agent to said subject in a treatment-effective amount; the method including administering said active agent to said subject at an earlier age when said subject carries a genetic variant of the TOMM40 gene associated with increased risk of Alzheimer's disease as compared to a corresponding subject who does not carry said genetic variant, wherein said genetic variant of the TOMM40 gene is rs10524523, to thereby treat said Alzheimer's disease.

In some embodiments, treating is carried out by delaying the onset of Alzheimer's disease or a symptom thereof with the administering.

In some embodiments, the active agent is a peroxisome proliferator-activated receptor agonist or modulator, for example, pioglitazone or a pharmaceutically acceptable salt thereof.

In some embodiments, the variant comprises a poly-T of at least 19 contiguous base pairs. In some embodiments, the variant comprises a poly-T of at least 26 contiguous base pairs. In some embodiments, the variant comprises a poly-T of at least 30 contiguous base pairs.

Also provided is a method of determining a risk for developing Alzheimer's disease in a patient including: (a) obtaining a patient profile, wherein said obtaining a patient profile may include: (i) detecting a genetic variant of the TOMM40 gene associated with increased or decreased risk of Alzheimer's disease, wherein said variant is rs10524523, and wherein said detecting comprises determining the poly-T length thereof; wherein the length identifies said patient as a patient at risk for developing Alzheimer's disease at an earlier or later age, (ii) determining the age of said patient, and then (b) converting said patient profile into said risk.

In some embodiments, obtaining a patient profile may include determining the APOE genotype of said patient. In some embodiments, the converting step may be carried out by computer program instructions.

Provided herein is a method for identifying a genetic variant that is associated with development of a condition of interest (e.g., earlier or later onset of a disease of interest), comprising: (a) determining from biological samples containing DNA the nucleotide sequences carried by a plurality of individual human subjects at a genetic locus of interest, wherein subjects include both (i) subjects affected with the condition of interest and (ii) subjects unaffected with the condition of interest; (b) identifying genetic variants at said genetic locus from nucleotide sequences observed in said plurality of subjects (e.g., using a multiple sequence alignment analysis); (c) mapping said genetic variants by constructing a phylogenetic tree of said nucleotide sequences of said subjects, said tree comprising branches that identify variant changes between said subjects (e.g., variant changes on the same cistron); (d) examining the genetic variants represented as branches in said tree and determining the ratio of affected and unaffected subjects to identify those changes that lead to a changed ratio of affected to unaffected subjects (preferably wherein the starting point is the genetic variant representing the greatest number of subjects); and then (e) identifying a genetic variant or group of variants (a haplotype) where the ratio of affected to unaffected subjects is substantially different from one or more adjacent variants on said tree (e.g., at least 5, 10, 15, 20, 25, 30, 35, 40, 45, 50, 55, 60, 65, 70, 75, 80, 85, or 90% different) to thereby identify a genetic variant associated with the development of said condition of interest.

In some embodiments, all subjects carry a same known polymorphism that is associated with the condition of interest.

In some embodiments, the condition of interest is a neurodegenerative disease, a metabolic disease (e.g., dyslipidemia), a cardiovascular disease, a psychiatric disorder, or cancer. In some embodiments, the disease of interest is a disease in which ApoE and/or TOMM40 are implicated in disease pathogenesis.

In some embodiments, the condition of interest is associated with increased or decreased mitochondrial dysfunction. In some embodiments, the condition of interest is schizophrenia. In some embodiments, the condition of interest is coronary artery disease. In some embodiments, the condition of interest is diabetes mellitus, type II. In some embodiments, the condition of interest is Parkinson's disease. In some embodiments, the condition of interest is Alzheimer's disease.

In some embodiments, the known polymorphism risk factor is the Apolipoprotein E allele (e.g., ApoE 2, ApoE 3 or ApoE 4).

In some embodiments, the genetic locus of interest is in linkage disequilibrium with the known polymorphism. In some embodiments, the genetic locus of interest is on the same chromosome and less than 10, 20, 30, 40, or 50 kilobases away from the known polymorphism. In some embodiments, the genetic locus is TOMM40.

Also provided is a method of determining increased risk for development of a condition of interest, comprising: (a) determining from a biological sample containing DNA a genetic variant identified by the method of any of the preceding paragraphs carried by an individual subject; and then (b) determining the subject is at increased risk for development of the condition of interest when the genetic variant is present.

Further provided is a method of determining increased risk for development of Alzheimer's disease in a subject (e.g., a subject carrying at least one Apo E3 allele), comprising: (a) detecting from a biological sample containing DNA taken from the subject the presence or absence of a genetic variant of the TOMM40 gene associated with increased or decreased risk of Alzheimer's disease; and (b) determining the subject is at increased or decreased risk of Alzheimer's disease when the genetic variant is present or absent.

In some embodiments, it is determined whether the subject is an Apo E2/E2, E2/E3, E2/E4, E3/E3, E3/E4, or E4/E4 subject. In some embodiments, it is determined whether the subject is an Apo E3/E3 or E3/E4 subject.

In some embodiments, the method further includes the step of: (c) administering an anti-Alzheimer's disease active agent to the subject in a treatment effective amount when the subject is determined to be at increased risk of Alzheimer's disease.

In some embodiments, the administering step is carried out in the subject at an earlier age when the subject is determined to be at increased risk by the presence or absence of the genetic variant as compared to a subject in which the genetic variant is not present or absent (e.g., for an ApoE 4/4 subject, beginning at age 45, 46, 47, 48, 49, 50, 51, 52, or 53, and continuously through each year thereafter, rather than beginning at age 55 or more; for an ApoE 4/3 subject, at age 50, 51, 52, 53, 54, 55, 56, 57, or 58, and continuously through each year thereafter, rather than beginning at age 60 or more; for an ApoE 3/3 subject, at age 55, 56, 57, 58, 59, 60, 61, 62, or 63, and continuously through each year thereafter, rather than beginning at age 65 or more; and for an ApoE 2/3 subject, at age 60, 61, 62, 63, 64, 65, 66, 67, or 68, and continuously through each year thereafter, rather than beginning at age 70 or more).

In some embodiments, the active agent is selected from the group consisting of acetylcholinesterase inhibitors, NMDA receptor antagonists, PPAR agonists or modulators (e.g., drugs in the thiazolidinedione or glitazar classes), antibodies, fusion proteins, therapeutic RNA molecules, and combinations thereof. In some embodiments, the active agent is rosiglitazone or a pharmaceutically acceptable salt thereof.

In some embodiments, the genetic variant of the TOMM40 is a variant listed in Table 1 as set forth below. In some embodiments, the genetic variant of TOMM40 is rs10524523, and increased risk is determined by a poly-T of 19 or greater at this locus.

Also provided is a method of treating a subject (e.g., a subject having at least one ApoE 3) allele for Alzheimer's disease by administering an anti-Alzheimer's disease active agent to the subject in a treatment-effective amount; the improvement comprising: administering the active agent to the subject at an earlier age when the subject carries a genetic variant of the TOMM40 gene associated with increased risk of Alzheimer's disease as compared to a corresponding subject who does not carry the genetic variant (e.g., for an ApoE 4/4 subject, beginning at age 45, 46, 47, 48, 49, 50, 51, 52, or 53, and continuously through each year thereafter, rather than beginning at age 55 or more; for an ApoE 4/3 subject, at age 50, 51, 52, 53, 54, 55, 56, 57, or 58, and continuously through each year thereafter, rather than beginning at age 60 or more; for an ApoE 3/3 subject, at age 55, 56, 57, 58, 59, 60, 61, 62, or 63, and continuously through each year thereafter, rather than beginning at age 65 or more; and for an ApoE 2/3 subject, at age 60, 61, 62, 63, 64, 65, 66, 67, or 68, and continuously through each year thereafter, rather than beginning at age 70 or more).

In some embodiments, the subject is an Apo E2/E2, E2/E3, E2/E4, E3/E3, E3/E4, E4/E4 subject. In some embodiments, the subject is an Apo E3/E3 or E3/E4 subject.

In some embodiments, the active agent is selected from the group consisting of acetylcholinesterase inhibitors, NMDA receptor antagonists, PPAR agonists or modulators (e.g., drugs in the thiazolidinedione or glitazar classes), antibodies, fusion proteins, therapeutic RNA molecules, and combinations thereof. In some embodiments, the active agent is pioglitazone, rosiglitazone, or a pharmaceutically acceptable salt thereof.

In some embodiments, the genetic variant of the TOMM40 gene is a deletion/insertion polymorphism (DIP). In some embodiments, the DIP is an insertion polymorphism. In some embodiments, the DIP is poly-T deletion/insertion polymorphism (e.g., between 5 and 100, or 10 and 80, or 20 and 50 bp poly-T).

In some embodiments, the genetic variant of the TOMM40 is a variant listed in Table 1 as set forth below. In some embodiments, the DIP is rs10524523, rs10602329 or DIP3. In some embodiments, the genetic variant of TOMM40 is rs10524523, and increased risk is determined by a poly-T of 19 or greater at this locus.

Further provided is a method of treatment for a condition of interest, wherein the condition of interest is associated with ApoE and/or TOMM40, for a patient in need thereof, the method including the steps: (a) determining the presence or absence of a genetic variant identified by the method as detailed herein carried by an individual subject to generate a genetic profile of the patient; and then, if the profile is indicative of the patient being responsive to an active agent, (b) administering the active agent to the subject in a treatment effective amount to treat the condition of interest.

In some embodiments, the active agent is selected from the group consisting of acetylcholinesterase inhibitors, NMDA receptor antagonists, PPAR agonists or modulators (e.g., drugs in the thiazolidinedione or glitazar classes), antibodies, fusion proteins, therapeutic RNA molecules, and combinations thereof. In some embodiments, the active agent is rosiglitazone or a pharmaceutically acceptable salt thereof.

In some embodiments, the genetic variant of the TOMM40 gene is a deletion/insertion polymorphism (DIP). In some embodiments, the DIP is an insertion polymorphism. In some embodiments, the DIP is poly-T deletion/insertion polymorphism (e.g., between 5 and 100, or 10 and 80, or 20 and 50 bp poly-T insertion).

In some embodiments, the genetic variant of the TOMM40 is a variant of TOMM40 listed in Table 1 as set forth below. In some embodiments, the DIP is rs10524523, rs10602329 or DIP3. In some embodiments, the DIP is rs10524523.

Also provided is a method of treatment for Alzheimer's disease in a subject, including: (a) detecting from a biological sample containing DNA taken from the subject the presence or absence of a genetic variant of the TOMM40 gene associated with responsiveness to an active agent; and, if the genetic variant is present, (b) administering the active agent to the subject in a treatment effective amount to treat the Alzheimer's disease.

In some embodiments, the subject carries at least one ApoE 3 allele. In some embodiments, the subject is an Apo E3/E3 or E3/E4 subject.

In some embodiments, the active agent is selected from the group consisting of acetylcholinesterase inhibitors, NMDA receptor antagonists, PPAR agonists or modulators (e.g., drugs in the thiazolidinedione or glitazar classes), antibodies, fusion proteins, therapeutic RNA molecules, and combinations thereof. In some embodiments, the active agent is pioglitazone, rosiglitazone, or a pharmaceutically acceptable salt thereof.

In some embodiments, the genetic variant of the TOMM40 gene is a deletion/insertion polymorphism (DIP). In some embodiments, the DIP is an insertion polymorphism. In some embodiments, the DIP is poly-T deletion/insertion polymorphism (e.g., between 5 and 100, or 10 and 80, or 20 and 50 bp poly-T).

In some embodiments, the genetic variant of the TOMM40 gene is a variant listed in Table 1 as set forth below. In some embodiments, the DIP is rs10524523, rs10602329 or DIP3. In some embodiments, the genetic variant of TOMM40 is rs10524523, and increased risk is determined by a poly-T of 19 or greater at this locus.

A method of determining a prognosis for a patient at risk for developing Alzheimer's disease is provided, including obtaining a patient profile, wherein the obtaining a patient profile includes: detecting the presence or absence of at least one ApoE allele in a biological sample of the patient, and detecting the presence or absence of at least one TOMM40 deletion/insertion polymorphism (DIP) located in intron 6 or intron 9 of the TOMM40 gene, and then, converting the patient profile into the prognosis, wherein the presence of the ApoE allele and the presence of the at least one TOMM40 DIP polymorphism identifies the patient as a patient at risk for developing Alzheimer's disease.

In some embodiments, the DIP is an insertion polymorphism. In some embodiments, the DIP is poly-T deletion/insertion polymorphism (e.g., between 5 and 100, or 10 and 80, or 20 and 50 poly-T).

In some embodiments, the DIP is rs10524523, rs10602329 or DIP3. In some embodiments, the genetic variant of TOMM40 is rs10524523, and increased risk is determined by a poly-T of 19 or greater at this locus.

In some embodiments, the method further includes detecting whether the subject is an Apo E2/E2, E2/E3, E2/E4, E3/E3, E3/E4, E4/E4 subject. In some embodiments, the subject is an Apo E3/E3 or E3/E4 subject.

Also provided is a method for stratifying a subject into a subgroup of a clinical trial of a therapy for the treatment of Alzheimer's disease, the method including: detecting the presence or absence of at least one ApoE allele in a biological sample of the patient, and detecting the presence or absence of at least one TOMM40 deletion/insertion polymorphism (DIP) located in intron 6 or intron 9 of the TOMM40 gene, wherein the subject is stratified into the subgroup for the clinical trial of the therapy based upon the presence or absence of the at least one ApoE and/or TOMM40 DIP allele.

In some embodiments, the DIP is an insertion polymorphism. In some embodiments, the DIP is poly-T insertion polymorphism (e.g., between 5 and 100, or 10 and 80, or 20 and 50 poly-T insertion).

In some embodiments, the DIP is rs10524523, rs10602329 or DIP3. In some embodiments, the genetic variant of TOMM40 is rs10524523, and increased risk is determined by a poly-T of 19 or greater at this locus.

In some embodiments, the method further includes detecting whether the subject is an Apo E2/E2, E2/E3, E2/E4, E3/E3, E3/E4, E4/E4 subject. In some embodiments, the subject is an Apo E3/E3 or E3/E4 subject.

Further provided is a method for identifying a patient in a clinical trial of a treatment for Alzheimer's disease including: a) identifying a patient diagnosed with Alzheimer's disease; and b) determining a prognosis for the patient diagnosed with Alzheimer's disease comprising obtaining a patient profile, wherein the patient profile comprises i) detecting the presence or absence of at least one ApoE allele in a biological sample of the patient, ii) detecting the presence or absence of at least one TOMM40 deletion/ insertion polymorphism (DIP) located in intron 6 or intron 9 of the TOMM40 gene, and converting the patient profile into the prognosis, the prognosis including a prediction of whether the patient is a candidate for the clinical trial for the treatment of Alzheimer's disease.

In some embodiments, the DIP is an insertion polymorphism. In some embodiments, the DIP is poly-T deletion/ insertion polymorphism (e.g., between 5 and 100, or 10 and 80, or 20 and 50 poly-T).

In some embodiments, the DIP is rs10524523, rs10602329 or DIP3. In some embodiments, the genetic variant of TOMM40 is rs10524523, and increased risk is determined by a poly-T of 19 or greater at this locus.

In some embodiments, the method further includes detecting whether the subject is an Apo E2/E2, E2/E3, E2/E4, E3/E3, E3/E4, E4/E4 subject. In some embodiments, the subject is an Apo E3/E3 or E3/E4 subject.

A kit for determining if a subject is at increased risk of developing late onset Alzheimer's disease is provided, including: at least one reagent that specifically detects the presence or absence of at least one TOMM40 deletion/ insertion polymorphism (DIP) located in intron 6 or intron 9 of the TOMM40 gene; and instructions for determining that the subject is at increased risk of developing late onset Alzheimer's disease by: (i) detecting the presence or absence of at least one TOMM40 deletion/insertion polymorphism (DIP) located in intron 6 or intron 9 of the TOMM40 gene; and (iii) observing whether or not the subject is at increased risk of developing late onset Alzheimer's disease by observing if the presence of the TOMM40 DIP is or is not detected with the at least one reagent, wherein the presence of the TOMM40 DIP indicates the subject is at increased risk of developing late onset Alzheimer's disease.

In some embodiments, the at least one reagent and the instructions are packaged in a single container.

In some embodiments, the DIP is an insertion polymorphism. In some embodiments, the DIP is poly-T deletion/ insertion polymorphism (e.g., between 5 and 100, or 10 and 80, or 20 and 50 poly-T).

In some embodiments, the DIP is rs10524523, rs10602329 or DIP3. In some embodiments, the genetic variant of TOMM40 is rs10524523, and increased risk is determined by a poly-T of 19 or greater at this locus.

In some embodiments, the determining step further includes detecting whether the subject is an Apo E2/E2, E2/E3, E2/E4, E3/E3, E3/E4, or E4/E4 subject. In some embodiments, the subject is an Apo E3/E3 or E3/E4 subject.

A kit is provided for determining if a subject is responsive to treatment for a condition of interest, wherein the condition of interest is associated with ApoE and/or TOMM40, with an active agent, the kit including: at least one reagent that specifically detects the presence or absence of at least one TOMM40 deletion/insertion polymorphism (DIP) located in intron 6 or intron 9 of the TOMM40 gene; and instructions for determining that the subject is responsive to treatment for the condition of interest with the active agent of interest by: (i) detecting the presence or absence of at least one TOMM40 deletion/insertion polymorphism (DIP) located in intron 6 or intron 9 of the TOMM40 gene; and (iii) determining whether or not the subject is responsive to treatment by observing if the presence of the TOMM40 DIP is or is not detected with the at least one reagent, wherein the presence of the TOMM40 DIP indicates that the subject is responsive to the treatment with the active agent.

In some embodiments, the at least one reagent and the instructions are packaged in a single container.

In some embodiments, the DIP is an insertion polymorphism. In some embodiments, the DIP is poly-T deletion/ insertion polymorphism (e.g., between 5 and 100, or 10 and 80, or 20 and 50 bp poly-T).

In some embodiments, the DIP is rs10524523, rs10602329 or DIP3. In some embodiments, the DIP is rs10524523. In some embodiments, the genetic variant of TOMM40 is rs10524523, and increased risk is determined by a poly-T of 19 or greater at this locus.

In some embodiments, the determining step further includes detecting whether the subject is an Apo E2/E2, E2/E3, E2/E4, E3/E3, E3/E4, or E4/E4 subject. In some embodiments, the subject is an Apo E3/E3 or E3/E4 subject.

It will be understood that all of the foregoing embodiments can be combined in any way and/or combination. The foregoing and other objects and aspects of the present invention are explained in greater detail in the drawings provided herewith and in the specification set forth below.

BRIEF DESCRIPTION OF THE DRAWINGS

FIGS. 7A and 7B illustrate the SNPs (FIG. 7A) and rs10524523 length polymorphisms (FIG. 7B) in the two major clades. Descriptive statistics are provided for each group of length polymorphisms (FIG. 7B). Several long haplotypes that formed individual outgroups in the tree, or very small clades, are in the group identified as 'Remainder.'

DETAILED DESCRIPTION

Figure 1:
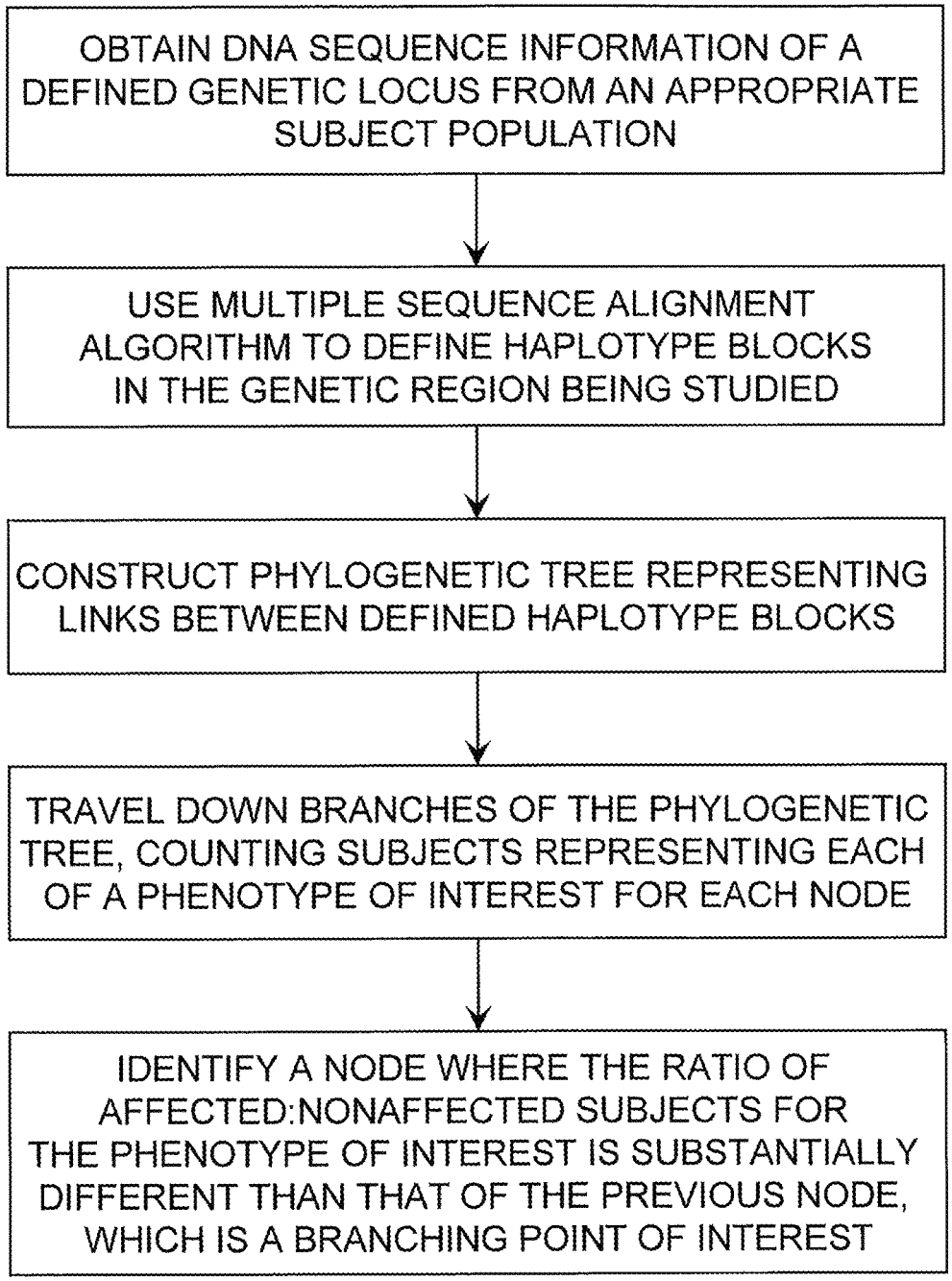
FIG. 1 shows a general flowchart for identifying a genetic variant in a predetermined region of genomic sequence in a genetic locus of interest, which may be associated with a condition of interest, according to some embodiments.

The present invention is explained in greater detail below. This description is not intended to be a detailed catalog of all the different ways in which the invention may be implemented, or all of the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

As used in the description of the invention and the appended claims, the singular forms "a", "an" and "the" are intended to include the plural forms as well, unless the context clearly indicates otherwise. Also, as used herein, "and/or" refers to and encompasses any and all possible combinations of one or more of the listed items, as well as the lack of combinations when interpreted in the alternative ("or").

In one aspect, the analysis of the genetic variation is based on variant sequence data. In a second aspect, the structure is uncovered using diploid genotype data, thereby avoiding the need to either experimentally or computationally infer the component haplotypes (see, e.g., U.S. Pat. No. 6,027,896 to Roses et al.). In another aspect, the present method can be applied onto uncharacterized allelic variation that results from the interrogation of a target nucleic acid with an experimental procedure that provides a record of the sequence variation present but does not actually provide the entire sequence. The underlying structure of genetic variation is also useful for the deduction of the constituent haplotypes from diploid genotype data.

It is preferred and contemplated that the methods described herein be used in conjunction with other clinical diagnostic information known or described in the art which are used in evaluation of subjects with diseases or disorders (e.g., those believed to involve mitochondrial dysfunction (e.g. Alzheimer's disease or other neurodegenerative diseases)) or for evaluation of subjects suspected to be at risk for developing such disease. The invention is also applicable for discovery of genetic risk factors for other complex diseases, disorders, or conditions.

The disclosures of all United States patent references cited herein are hereby incorporated by reference herein in their entirety.

1. Definitions. The following definitions are used herein:

"Condition of interest" refers to a specific condition, disease, or disorder designated for phylogenetic study and/or subsequent diagnosis or prognosis, including, but not limited to, the age of onset thereof. "Condition" as used herein includes, but is not limited to, conditions associated with ApoE and/or TOMM40 and/or mitochondrial dysfunction, e.g., neurodegenerative diseases, metabolic diseases, psychiatric disorders, and cancer.

Examples of conditions in which ApoE and/or TOMM40 have been implicated include, but are not limited to, cardiovascular disease; metabolic disease; neurodegenerative disease; neurological trauma or disease; autoimmune disease (e.g., multiple sclerosis (Pinholt M, et al. Apo E in multiple sclerosis and optic neuritis: the apo E-epsilon4 allele is associated with progression of multiple sclerosis. *Mult Scler.* 11:511-5 (2005); Masterman, T. & Hillert, J. The telltale scan: APOE ε 4 in multiple sclerosis. Lancet Neurol. 3: 331 (2004), neuropsychiatric systemic lupus erythematosus (Pullmann Jr. R, et al. Apolipoprotein E polymorphism in patients with neuropsychiatric SLE. *Clin Rheumatol.* 23:

97-101 (2004)), etc.)); viral infection (e.g., liver disease associated with hepatitis C infection (Wozniak M A, et al. Apolipoprotein E-E4 protects against severe liver disease caused by hepatitis C virus. *Hepatol.* 36: 456-463 (2004)), HIV disease (Burt T D, et al. Apolipoprotein (apo) E4 enhances HIV-1 cell entry in vitro, and the APOE epsilon4/epsilon4 genotype accelerates HIV disease progression. *Proc Natl Acad Sci USA.* 105:8718-23 (2008)), etc.)); hip fracture/osteoporosis (Pluijm S M, et al. Effects of gender and age on the association of apolipoprotein E epsilon4 with bone mineral density, bone turnover and the risk of fractures in older people. *Osteoporos Int.* 13: 701-9 (2002)); mitochondrial diseases (Chang S, et al. Lipid- and receptor-binding regions of apolipoprotein E4 fragments act in concert to cause mitochondrial dysfunction and neurotoxicity. *Proc Natl Acad Sci USA.* 102:18694-9 (2005)); aging (Schächter F, et al. Genetic associations with human longevity at the APOE and ACE loci. *Nat Genet.* 6:29-32 (1994); Rea I M, et al., Apolipoprotein E alleles in nonagenarian subjects in the Belfast Elderly Longitudinal Free-living Ageing Study (BELFAST). *Mech. Aging and Develop.* 122: 1367-1372 (2001)); inflammation (Li L, et al., Infection induces a positive acute phase apolipoprotein E response from a negative acute phase gene: role of hepatic LDL receptors. *J Lipid Res.* 49:1782-93 (2008)); and memory dysfunction (Caselli R J, et al. Longitudinal modeling of age-related memory decline and the APOE epsilon4 effect. *N Engl J Med.* 361:255-63 (2009)).

"Cardiovascular disease" as used herein refers to a disease involving the heart and/or blood vessels, including, but not limited to, coronary artery disease (Song Y, et al. Meta-analysis: apolipoprotein E genotypes and risk for coronary heart disease. *Ann Intern Med.* 141:137-47 (2004); Bennet A M, et al., Association of apolipoprotein E genotypes with lipid levels and coronary risk. *JAMA* 298:1300-11 (2007)), atherosclerosis (Norata G D, et al. Effects of PCSK9 variants on common carotid artery intima media thickness and relation to ApoE alleles. *Atherosclerosis* (2009) Jun. 27. [Epub ahead of print], doi:10.1016/j.atherosclerosis 2009.06.023; Paternoster L, et al. Association Between Apolipoprotein E Genotype and Carotid Intima-Media Thickness May Suggest a Specific Effect on Large Artery Atherothrombotic Stroke. *Stroke* 39:48-54 (2008)), ischemic heart disease (Schmitz F, et al., Robust association of the APOE 4 allele with premature myocardial infarction especially in patients without hypercholesterolaemia: the Aachen study. *Eur. J. Clin. Investigation* 37: 106-108 (2007)), vascular disease such as ischemic stroke (Peck G, et al. The genetics of primary haemorrhagic stroke, subarachnoid haemorrhage and ruptured intracranial aneurysms in adults. *PLoS One.* 3:e3691 (2008); Paternoster L, et al. Association Between Apolipoprotein E Genotype and Carotid Intima-Media Thickness May Suggest a Specific Effect on Large Artery Atherothrombotic Stroke. *Stroke* 39:48-54 (2008)), vascular dementia (Bang O Y, et al. Important link between dementia subtype and apolipoprotein E: a meta-analysis. *Yonsei Med J.* 44:401-13 (2003); Baum L, et al. Apolipoprotein E epsilon4 allele is associated with vascular dementia. *Dement Geriatr Cogn Disord.* 22:301-5 (2006)), etc.

"Neurodegenerative disease" as used herein refers to Alzheimer's disease (Corder E H, et al. Gene dose of apolipoprotein E type 4 allele and the risk of Alzheimer's disease in late onset families. *Science* 261:921-3 (1993); Corder E H, et al. There is a pathologic relationship between ApoE-epsilon 4 and Alzheimer's disease. *Arch Neurol.* 52:650-1 (1995)), Parkinson's disease (Huang X, et al. Apolipoprotein E and dementia in Parkinson disease: a meta-analysis. *Arch Neurol.* 63:189-93 (2006); Huang X et al. APOE-[epsilon]2 allele associated with higher prevalence of sporadic Parkinson disease. *Neurology.* 62:2198-202 (2004); Martinez, M. et al. Apolipoprotein E4 is probably responsible for the chromosome 19 linkage peak for Parkinson's disease. *Am. J. Med. Genet. B Neuropsychiatr. Genet.* 136B, 172-174 (2005)), Huntington's disease, and a plurality of less common diseases and disorders which cause neurons to decline, e.g., age-related macular degeneration (Thakkinstian A, et al. Association between apolipoprotein E polymorphisms and age-related macular degeneration: A HuGE review and meta-analysis. *Am J Epidemiol.* 164:813-22 (2006); Bojanowski C M, et al. An apolipoprotein E variant may protect against age-related macular degeneration through cytokine regulation. *Environ Mol Mutagen.* 47:594-602 (2006)).

"Neurological trauma or disease" includes, but is not limited to, outcome after head injury (Zhou W, et al. Meta-analysis of APOE4 allele and outcome after traumatic brain injury. *J Neurotrauma.* 25:279-90 (2008); Lo T Y, et al. Modulating effect of apolipoprotein E polymorphisms on secondary brain insult and outcome after childhood brain trauma. *Childs Nerv Syst.* 25:47-54 (2009)), migraine (Gupta R, et al. Polymorphism in apolipoprotein E among migraineurs and tension-type headache subjects. *J Headache Pain.* 10:115-20 (2009)), vasogenic edema (James M L, et al. Apolipoprotein E modifies neurological outcome by affecting cerebral edema but not hematoma size after intracerebral hemorrhage in humans. *J Stroke Cerebrovasc Dis.* 18:144-9 (2009); James M L, et al. Pharmacogenomic effects of apolipoprotein e on intracerebral hemorrhage. *Stroke* 40:632-9 (2009)), etc.

"Metabolic disease" as used herein includes, but is not limited to, dyslipidemia (Willer C J, et al. Newly identified loci that influence lipid concentrations and risk of coronary artery disease. *Nat Genet.* 40:161-9 (2008); Bennet A M, et al., Association of apolipoprotein E genotypes with lipid levels and coronary risk. *JAMA* 298:1300-11 (2007)), end stage renal disease (Oda H, et al. Apolipoprotein E polymorphism and renal disease. *Kidney Int Suppl.* 71:S25-7 (1999); Hubacek J A, et al. Apolipoprotein E Polymorphism in Hemodialyzed Patients and Healthy Controls. *Biochem Genet.* (2009) June 30. [Epub ahead of print] DOI 10.1007/s10528-009-9266-y.), chronic kidney disease (Yoshida T, et al. Association of a polymorphism of the apolipoprotein E gene with chronic kidney disease in Japanese individuals with metabolic syndrome. *Genomics* 93:221-6 (2009); Leiva E, et al. Relationship between Apolipoprotein E polymorphism and nephropathy in type-2 diabetic patients. *Diabetes Res Clin Pract.* 78:196-201 (2007)), gallbladder disease (Boland L L, et al. Apolipoprotein E genotype and gallbladder disease risk in a large population-based cohort. *Ann Epidemiol.* 16:763-9 (2006); Andreotti G, et al. Polymorphisms of genes in the lipid metabolism pathway and risk of biliary tract cancers and stones: a population-based case-control study in Shanghai, China. *Cancer Epidemiol Biomarkers Prev.* 17:525-34 (2008)), diabetes mellitus (type II) (Elosua R, et al. Obesity Modulates the Association among APOE Genotype, Insulin, and Glucose in Men. *Obes Res.* 11:1502-1508 (2003); Moreno J A, et al. The Apolipoprotein E Gene Promoter (−219G/T) Polymorphism Determines Insulin Sensitivity in Response to Dietary Fat in Healthy Young Adults. *J. Nutr.* 135:2535-2540 (2005)), metabolic syndrome, cholelithiasis (Abu Abeid S, et al. Apolipoprotein-E genotype and the risk of developing cholelithiasis following bariatric surgery: a clue to prevention of routine prophylactic cholecystectomy. *Obes Surg.* 12:354-7 (2002)), etc.

"Psychiatric Disorder" as used herein refers to schizophrenia (Kampman O, et al. Apolipoprotein E polymorphism is associated with age of onset in schizophrenia. *J Hum Genet.* 49:355-9 (2004); Dean B. et al., Plasma apolipoprotein E is decreased in schizophrenia spectrum and bipolar disorder. *Psychiatry Res.* 158:75-78 (2008)), obsessive compulsive disorder (OCD), addictive behavior (smoking addiction, alcohol addiction, etc.), bipolar disorder (Dean B. et al., Plasma apolipoprotein E is decreased in schizophrenia spectrum and bipolar disorder. *Psychiatry Res.* 158:75-78 (2008)), and other diseases, disorders, or conditions of a psychiatric nature.

"Development of a condition" as used herein refers to either an initial diagnosis of a disease, disorder, or other medical condition, or exacerbation of an existing disease, disorder, or medical condition for which the subject has already been diagnosed.

"Diagnosis" or "prognosis" as used herein refers to the use of information (e.g., genetic information or data from other molecular tests on biological samples, signs and symptoms, physical exam findings, cognitive performance results, etc.) to anticipate the most likely outcomes, timeframes, and/or response to a particular treatment for a given disease, disorder, or condition, based on comparisons with a plurality of individuals sharing common nucleotide sequences, symptoms, signs, family histories, or other data relevant to consideration of a patient's health status.

"Biological sample" as used herein refers to a material suspected of containing a nucleic acid of interest. Biological samples containing DNA include hair, skin, cheek swab, and biological fluids such as blood, serum, plasma, sputum, lymphatic fluid, semen, vaginal mucus, feces, urine, spinal fluid, and the like. Isolation of DNA from such samples is well known to those skilled in the art.

"Gene" as used herein means a segment of DNA that contains all the information for the regulated biosynthesis of an RNA product, including promoters, exons, introns, and other untranslated regions that control expression.

"Genetic locus" or "locus" as used herein means a location on a chromosome or DNA molecule, often corresponding to a gene or a physical or phenotypic feature or to a particular nucleotide or stretch of nucleotides. Loci is the plural form of locus.

"Amplification," as applied to nucleic acids herein refers to any method that results in the formation of one or more copies of a nucleic acid, where preferably the amplification is exponential. One such method for enzymatic amplification of specific sequences of DNA is known as the polymerase chain reaction (PCR), as described by Saiki et al., 1986, Science 230:1350-1354. Primers used in PCR normally vary in length from about 10 to 50 or more nucleotides, and are typically selected to be at least about 15 nucleotides to ensure sufficient specificity. The double stranded fragment that is produced is called an "amplicon," and may vary in length from as few as about 30 nucleotides, to 20,000 or more.

A "marker" or "genetic marker" as used herein is a known variation of a DNA sequence at a particular locus. The variation may be present in an individual due to mutation or inheritance. A genetic marker may be a short DNA sequence, such as a sequence surrounding a single base-pair change (single nucleotide polymorphism, SNP), or a long one, like minisatellites. Markers can be used to study the relationship between an inherited disease and its genetic cause (for example, a particular mutation of a gene that results in a defective or otherwise undesirable form of protein).

A "genetic risk factor" as used herein means a genetic marker that is associated with increased susceptibility to a condition, disease, or disorder. It may also refer to a genetic marker that is associated with a particular response to a selected drug or treatment of interest.

"Associated with" as used herein means the occurrence together of two or more characteristics more often than would be expected by chance alone. An example of association involves a feature on the surface of white blood cells called HLA (HLA stands for human leukocyte antigen). A particular HLA type, HLA type B-27, is associated with an increased risk for a number of diseases including ankylosing spondylitis. Ankylosing spondylitis is 87 times more likely to occur in people with HLA B-27 than in the general population.

A subject "at increased risk of developing a condition" due to a genetic risk factor is one who is predisposed to the condition, has genetic susceptibility for the condition, and/or is more likely to develop the condition than subjects in which the genetic risk factor is absent. For example, a subject who is "at increased risk of developing Alzheimer's disease" due to the presence of one or two ApoE 4 alleles is more likely to develop Alzheimer's disease than a subject who does not carry an ApoE 4 allele.

"Polymorphism" as used herein refers to the existence of two or more different nucleotide sequences at a particular locus in the DNA of the genome. Polymorphisms can serve as genetic markers and may also be referred to as genetic variants. Polymorphisms include nucleotide substitutions, insertions, deletions and microsatellites, and may, but need not, result in detectable differences in gene expression or protein function. A polymorphic site is a nucleotide position within a locus at which the nucleotide sequence varies from a reference sequence in at least one individual in a population.

A "deletion/insertion polymorphism" or "DIP" as used herein is an insertion of one or more nucleotides in one version of a sequence relative to another. If it is known which of the alleles represent minor alleles, the term "deletion" is used when the minor allele is a deletion of one or more nucleotides, and the term "insertion" is used when the minor allele is an addition of one or more nucleotides. The term "deletion/insertion polymorphism" is also used when there are multiple forms or lengths and the minor allele is not apparent. For example, for the poly-T polymorphisms described herein, multiple lengths of polymorphisms are observed.

"Polymorphism data" as used herein means information concerning one or more of the following for a specific gene: location of polymorphic sites; sequence variation at those sites; frequency of polymorphisms in one or more populations; the different genotypes and/or haplotypes determined for the gene; frequency of one or more of these genotypes and/or haplotypes in one or more populations; and any known association(s) between a trait and a genotype or a haplotype for the gene.

"Haplotype" as used herein refers to a genetic variant or combination of variants carried on at least one chromosome in an individual. A haplotype often includes multiple contiguous polymorphic loci. All parts of a haplotype as used herein occur on the same copy of a chromosome or haploid DNA molecule. Absent evidence to the contrary, a haplotype is presumed to represent a combination of multiple loci that are likely to be transmitted together during meiosis. Each human carries a pair of haplotypes for any given genetic locus, consisting of sequences inherited on the homologous chromosomes from two parents. These haplotypes may be identical or may represent two different genetic variants for the given locus. Haplotyping is a process for determining one or more haplotypes in an individual. Haplotyping may include use of family pedigrees, molecular techniques and/or statistical inference.

A "variant" or "genetic variant" as used herein, refers to a specific isoform of a haplotype found in a population, the specific form differing from other forms of the same haplotype in the sequence of at least one, and frequently more than one, variant sites or nucleotides within the sequence of the gene. The sequences at these variant sites that differ between different alleles of a gene are termed "gene sequence variants," "alleles," or "variants." The term "alternative form" refers to an allele that can be distinguished from other alleles by having at least one, and frequently more than one, variant sites within the gene sequence. "Variants" include isoforms having single nucleotide polymorphisms (SNPs) and deletion/insertion polymorphisms (DIPs). Reference to the presence of a variant means a particular variant, i.e., particular nucleotides at particular polymorphic sites, rather than just the presence of any variance in the gene.

"Isoform" as used herein means a particular form of a gene, mRNA, cDNA or the protein encoded thereby, distinguished from other forms by its particular sequence and/or structure. For example, the ApoE 4 isoform of apolipoprotein E as opposed to the ApoE2 or ApoE 3 isoforms.

"Cistron" as used herein means a section of DNA found on a single chromosome that contains the genetic code for a single polypeptide and functions as a hereditary unit. A cistron includes exons, introns, and regulatory elements related to a single functional unit (i.e., a gene). The term derives from the classic cis-trans test for determining whether genetic elements were able to functionally interact regardless of whether they were located on the same DNA molecule ("trans" complementation) or only when they were located on the same DNA molecule ("cis" acting elements).

The term "genotype" in the context of this invention refers to the particular allelic form of a gene, which can be defined by the particular nucleotide(s) present in a nucleic acid sequence at a particular site(s). Genotype may also indicate the pair of alleles present at one or more polymorphic loci. For diploid organisms, such as humans, two haplotypes make up a genotype. Genotyping is any process for determining a genotype of an individual, e.g., by nucleic acid amplification, antibody binding, or other chemical analysis. The resulting genotype may be unphased, meaning that the sequences found are not known to be derived from one parental chromosome or the other.

"Linkage disequilibrium" as used herein means the non-random association of alleles at two or more loci. Linkage disequilibrium describes a situation in which some combinations of alleles or genetic markers occur more or less frequently in a population than would be expected from a random formation of haplotypes from alleles based on their frequencies. Non-random associations between polymorphisms at different loci are measured by the degree of linkage disequilibrium.

"Multiple sequence alignment" or "MSA" as used herein means alignment of three or more nucleotide sequences from genomic DNA derived from a plurality of individuals to determine homology and heterology between the sequences. In general, the input set of query sequences are assumed to have an evolutionary relationship by which they share a lineage and are descended from a common ancestor. Computer algorithms are most often used to perform the analysis of aligned sequences.

Some embodiments of the present invention may include steps implemented by a computer and/or computer program products, including analog and/or digital hardware, and/or computer program instructions. These computer program instructions may be provided to a processor of a general purpose computer, special purpose computer, Application Specific Integrated Circuits (ASIC), and/or other programmable data processing apparatus, such that the instructions, which execute via the processor of the computer and/or other programmable data processing apparatus, create means for implementing the functions/acts specified. Other software, such as an operating system, also may be included. It will be further appreciated that the functionality of the multiple sequence alignment module, mapping module and/or other modules described herein may be embodied, at least in part, using discrete hardware components, one or more ASIC and/or one or more special purpose digital processors and/or computers.

"Mapping" as used herein means creating a phylogenetic tree by assigning a node to each new nucleotide sequence variant observed, connecting that node to another node representing a known sequence carried by the same individual on the same chromosome or cistron, and counting the numbers of each type of subject represented at each node. See FIG. 4 for an example of a phylogenetic tree developed in this manner.

"Phylogenetic" means related to the study of evolutionary connections among various groups of organisms or individuals within a species. Before genetic information was readily available, phylogeny was based mostly on phenotypic observation. "Phylogenetic mapping" as used herein means using DNA sequence data to connect related sequence variants carried by a plurality of individuals in order to determine evolutionary connections and the chronology of divergence. A "phylogenetic tree" is the result of mapping the connections between variants.

"Node" as used herein means a polymorphism data point on a phylogenetic tree representing an actual variant sequence carried by at least one subject. A node is connected by a branch to another node representing a variant sequence carried by the same individual on the same chromosome and in the same cistron but at a different genetic locus within the cistron. The presence of a node indicates that at least one subject carried both the sequence indicated by the node as well as the sequence represented by the neighboring node to which it is connected by a branch.

"Branch" as used herein means a connection between two nodes representing two distinct variant sequences or haplotypes, wherein the two variants are located on the same chromosome and in the same cistron from an individual subject. "Branching point" means any node from which more than two branches extend, but it is especially used herein to refer to a root node from which three or more nodes extend. A "root node" represents the genetic sequence of a common evolutionary ancestor from which genetic divergence has generated the variety of nearby sequence variants represented by the connected nodes.

"Iteratively" as used herein refers to repetitive calculation of values for each character in a series. For example, each node on a phylogenetic tree is analyzed to calculate the ratio of the number of subjects affected with a condition of interest (such as Alzheimer's disease) to control unaffected subjects; this ratio is compared with the connected nodes to locate correlations with increased or decreased risk for developing a disease, disorder, or condition of interest. A substantial change in this ratio between one node and the next indicates the presence of a variant that either increases or decreases the risk of earlier disease onset. "Iteratively examining the genetic variants" means beginning the analysis with nodes representing the sequences shared by the greatest numbers of individual subjects and successively analyzing the nodes connected by branches extending from that node, followed by the second level of nodes, and so on. The analysis then moves overall from the roots of the tree toward the outer branches and nodes of the tree.

"Treatment" as used herein includes any drug, procedure, lifestyle change, or other adjustment introduced in attempt to effect a change in a particular aspect of a subject's health (i.e. directed to a particular disease, disorder, or condition).

"Drug" as used herein refers to a chemical entity or biological product, or combination of chemical entities or biological products, administered to a person to treat or prevent or control a disease or condition. The term "drug" as used herein is synonymous with the terms "medicine," "medicament," "therapeutic intervention," or "pharmaceutical product." Most preferably the drug is approved by a government agency for treatment of at least one specific disease or condition.

"Disease," "disorder," and "condition" are commonly recognized in the art and designate the presence of signs and/or symptoms in an individual or patient that are generally recognized as abnormal and/or undesirable. Diseases or conditions may be diagnosed and categorized based on pathological changes. The disease or condition may be selected from the types of diseases listed in standard texts such as Harrison's Principles of Internal Medicine, 1997, or Robbins Pathologic Basis of Disease, 1998.

"Mitochondrial dysfunction" as used herein means any detrimental abnormalities of the mitochondria within a cell or cells. Some diseases, disorders, or conditions presently known in the art to be associated with mitochondrial dysfunction include Alzheimer's disease, Parkinson's disease, and other neurodegenerative diseases, ischemia-reperfusion injury in stroke and heart attack, epilepsy, diabetes, and aging. Many other diseases, disorders, and conditions have been associated with mitochondrial dysfunction in the art. Indeed, the mitochondrion is critical for proper functioning of most cell types, and mitochondrial decline often leads to cell death. This mitochondrial dysfunction causes cell damage and death by compromising ATP production, disrupting calcium homeostasis and increasing oxidative stress. Furthermore, mitochondrial damage can lead to apoptotic cell death by causing the release of cytochrome c and other pro-apoptotic factors into the cytoplasm (for review, see Wallace, 1999; Schapira, 2006). Regarding a specific example found herein, the ApoE 3 and ApoE 4 isoforms are hypothesized to cause mitochondrial dysfunction through interactions with TOMM40. Some TOMM40 variants may act synergistically with ApoE 3 isoform to accelerate mitochondrial decline. This mitochondrial mechanism is believed to contribute to many complex genetic diseases, disorders, and conditions.

"Subjects" are preferably, but not limited to, human subjects. The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult, and geriatric. Subjects may also include animal subjects, particularly mammalian subjects such as canines, felines, bovines, caprines, equines, ovines, porcines, rodents (e.g., rats and mice), lagomorphs, primates (including non-human primates), etc., screened for veterinary medicine or pharmaceutical drug development purposes.

A "subject" according to some embodiments is an individual whose genotype(s) or haplotype(s) are or have been determined, and may have been recorded in conjunction with the individual's condition (i.e., disease or disorder status, including, but not limited to, the disease risk status and/or age of onset prediction) and/or response to a candidate drug or treatment. Nucleotide sequences from a plurality of subjects are used to construct a phylogenetic tree to identify nucleotide sequences associated with the trait, or condition of interest. Then analogous nucleotide sequences from an individual subject may be compared to those that are identified as being associated with the trait, or condition of interest, for diagnostic, prognostic and/or predictive purposes.

"Treat," "treating," or "treatment" as used herein refers to any type of measure that imparts a benefit to a patient afflicted with or at risk for developing a disease, including improvement in the condition of the patient (e.g., in one or more symptoms), delay in the onset or progression of the disease, etc.

"Late-onset Alzheimer's disease" or "LOAD" as used herein is known in the art, and is the classification used if the Alzheimer's disease has an onset or is diagnosed after the age of 65. It is the most common form of Alzheimer's disease.

"Cognitive impairment" includes deficiencies in information processing. "Mild cognitive impairment" or "MCI" is cognitive impairment that is worse than that expected for a given age and education level, but does not interfere significantly with daily activities. "Amnesic MCI" is MCI where the predominant symptom is memory loss, and may be a risk factor for Alzheimer's disease.

2. Methods for Identifying Genetic Variants

While lists of associations derived from genome-wide scans are useful, they are generally inadequate to explain disease complexity. Families, pathways, and interactions of genes can provide specificities. High-resolution variant mapping may reveal answers to complex genetic interactions. This is particularly applicable where one known genetic risk factor which does not itself entirely explain an association to the disease, disorder, or condition of interest may present an excellent candidate genetic locus for more detailed investigations. Furthermore, pharmacogenetics, while useful for drug development, can also extend biological relevance. The analysis of sequence data from large numbers of individuals to discover variants in the gene sequence between individuals in a population will result in detection of a greater fraction of all the variants in the population.

The initial sequence information to be analyzed by the method of the present invention is derived from the genomic DNA of a plurality of subjects. The organism can be any organism for which multiple sequences are available, but is preferably from human. In identifying new variants it is often useful to screen different population groups based on race, ethnicity, gender, and/or geographic origin because particular variants may differ in frequency between such groups. Most preferably, for diseases or disorders believed to be multigenic (genetically complex diseases/disorders), the phenotypes represented by the subject population are from the extremes of a spectrum. Biological samples containing DNA may be blood, semen, cheek swab, etc. Isolation of DNA from such samples is well known in the art.

In some embodiments, the invention relates to the analysis of nucleotide sequence data from a plurality of subjects having at least one known risk factor for a given disease, disorder, or condition (genetic or otherwise). The nucleotide sequences are analyzed to generate haplotype data, and the haplotypes or genetic variants are then mapped onto a phylogenetic tree to demonstrate the evolution of the sequences represented. By comparing this tree to phenotype data about the plurality of subjects, a prognosis or diagnosis is possible for an individual subject carrying haplotypes observed on the phylogenetic tree.

In other embodiments, the invention relates to the fields of pharmacogenetics and pharmacogenomics and the use of genetic haplotype information to predict an individual's susceptibility to disease and/or their response to a particular drug or drugs, so that drugs tailored to genetic differences of population groups may be developed and/or administered to individuals with the appropriate genetic profile.

Nucleotide sequence information is derived from genomic DNA. Genomic sequence data used may be obtained from clinical or non-human animals or from cultured cells or isolated tissue studies. The organism can be any organism for which multiple sequences are available, but is preferably from human. In identifying new variants it is often useful to screen different population groups based on race, ethnicity, gender, and/or geographic origin because particular variants may differ in frequency between such groups. Most preferably, for diseases or disorders believed to be multigenic (genetically complex diseases/disorders), the phenotypes represented by the subject population are extreme opposites.

Biological samples containing DNA may be blood, semen, cheek swab, etc. Isolation of DNA from such samples is well known in the art. Methods for determining DNA sequence at a particular genetic locus of interest are also known in the art. Automated sequencing is now widely available and requires only an isolated DNA sample and at least one primer that is specifically designed to recognize a highly conserved sequence within or in close proximity to the genetic locus of interest.

According to some embodiments, a defined genetic region or locus of interest (e.g., defined by a set of forward and reverse PCR primers or coordinates on a reference sequence) is carefully sequenced from a cohort of people inclusive of patients who are well characterized for a particular disorder.

A consensus sequence is determined, and all observed sequence variants for a given genetic locus are compiled into a list. Variation in a genomic region during evolution results in divergence from the ancestral sequence. In the absence of recombination events, all the variations that occur in cis on the ancestral sequence are inherited together on a collinear piece of DNA. During initial phases of investigation at least, it is preferred that populations be parsed into groups of subjects sharing a common general phenotype representing similar ancestry. Otherwise, analysis of these data through construction of phylogenetic trees will require a prohibitively large number of subjects.

3. Multiple Sequence Alignments.

Determining the presence of a particular variant or plurality of variants in a gene or gene region in a population can be performed in a variety of ways, all of which involve locating a particular genetic locus by targeting sequences within the region of interest that are known to be highly conserved. From the highly conserved locus, the contiguous sequences are easily obtained through one of many techniques well-known in the art.

The first step in analyzing parallel DNA sequences from a plurality of subjects is multiple sequence alignment ("MSA"). MSA is typically used to display sequence alignment from homologous samples with polymorphic differences within genes or gene regions to show conserved areas and variant sequences. MSAs of the sequence information obtained at the locus of interest may be constructed using one or more various known techniques and publicly available software, and are publicly available from many sources including the Internet. Methods for analyzing multiple sequence alignments known in the art include, e.g., those described in U.S. Pat. No. 6,128,587 to Sjolander; U.S. Pat. No. 6,291,182 to Schork et al.; and U.S. Pat. No. 6,401,043 to Stanton et al.

4. Phylogenetic Trees and Analysis.

Various methods for construction of "phylogenetic trees" are known in the art. (See, e.g., Sanderson, 2008). Sun et al. used "haplotype block" analyses to study associations between toll-like receptor (TLR) variants and prostate cancer (2005) and Bardel et al. (2005) used a cladistic analysis approach to investigate associations between CARD15 gene variants and Crohn's disease. However, neither utilized genetic loci previously associated with the disease to investigate linkages.

Phylogenetic trees according to some embodiments may be constructed with a topology in which haplotype sequence variants observed in individual human subjects studied form nodes (representing each sequence observed in the data) on a tree. Nodes may be joined to other nodes, and the common ancestor is found at the branching site, common root or root node of the tree. A phylogenetic tree reflects the evolutionary relationship between genetic loci for which data are analyzed (see Sanderson, 2008; Tzeng, 2005; Seltman, 2003).

The starting point for phylogenetic tree estimation is generally an MSA (see above). Multiple software applications are available for constructing phylogenetic trees based on sequence data. See, e.g., U.S. Pat. Nos. 7,127,466 and 6,532,467 to Brocklebank, et al. The basic premise is that a genetic locus exhibiting many variants is represented by these variants connected in cis. Polymorphisms create branching points (nodes) in the tree that define groups of related sequences or haplotypes.

The phylogenetic tree is utilized for information by iteratively examining ratios of subjects affected with a condition to unaffected control subjects; the calculations begin with nodes observed in the greatest numbers of subjects and move toward the periphery of the tree to nodes observed in fewer subjects. The goal is to locate a branching point, branch, or node where there is substantial change in the ratio of subjects affected with the condition of interest to unaffected control subjects. Such a branching point represents the evolutionary divergence of higher risk subjects from lower risk subjects or vice versa.

Statistical analysis of the phylogenetic tree generated may be performed in accordance with the methods known in the art. One art-recognized method is the calculation of bootstrap confidence levels (see Efron et al., Proc. Natl. Acad. Sci. USA 93, 13429-13434 (1996)).

5. Patient Evaluation.

Once a phylogenetic tree has been generated for a particular genetic locus, an individual subject may be evaluated by comparing their DNA sequence to the sequences that comprise the phylogenetic tree. The presence of haplotypes or sequence variants corresponding with regions of the tree representing subjects with higher incidence of the condition of interest (i.e., higher ratios of subjects affected with the disease or disorder to unaffected control subjects) would mean that the individual subject is also at increased risk. Conversely, substantially lower ratios correspond to reduced risk of developing the condition of interest.

Phylogenetic trees may also be analyzed based upon responsiveness of the condition of interest to treatment with an active agent or treatment method of interest according to some embodiments.

6. APOE and TOMM40.

ApoE phenotypes and genotypes are well known in the art. The established nomenclature system as well as the phenotypes and genotypes for ApoE are described in, for example, Zannis et al., 1982, which is incorporated by reference herein.

TOMM40 (The Outer Mitochondrial Membrane channel subunit, 40 kDa) phenotypes and genotypes are also known. TOMM40 functions as a channel-forming subunit of the translocase found in the outer mitochondrial membrane and is essential for protein import into mitochondria.

Genome-wide association scanning data from studies of Alzheimer's disease patients have unequivocally identified the linkage disequilibrium region that contains the apolipoprotein E (ApoE) gene. The ApoE 4 allele has been widely replicated as a confirmed susceptibility gene since the initial publications in 1993 (see, e.g., Corder et al.). The genome-wide association scanning studies identified polymorphisms adjacent to APOE within the linkage disequilibrium region, with many of the associated polymorphisms located in the TOMM40 gene. This is a remarkable "coincidence" as cell biology studies have identified co-localization of ApoE and TOMM40 to the outer mitochondrial membrane. This other gene, TOMM40, was first encountered during studies modeling linkage disequilibrium around ApoE in 1998. The polymorphisms were located adjacent to ApoE within a small linkage disequilibrium region.

ApoE binds to mitochondria in human neuronal cultures (Chang, 2005). The localization of ApoE to the outer mitochondrial membrane suggests isoform-specific interactions, leading to a potential role for ApoE-induced mitochondrial apoptosis as an early step in Alzheimer's disease expression. Biological data have demonstrated that the proportion of mobile mitochondria in neuronal cell culture, as well as the speed at which they move and the distance that they traverse, are factors affecting increased mitochondrial apoptosis. Phylogenetic data suggest an independent genetic effect on the development of Alzheimer's disease for TOMM40.

Figure 3:
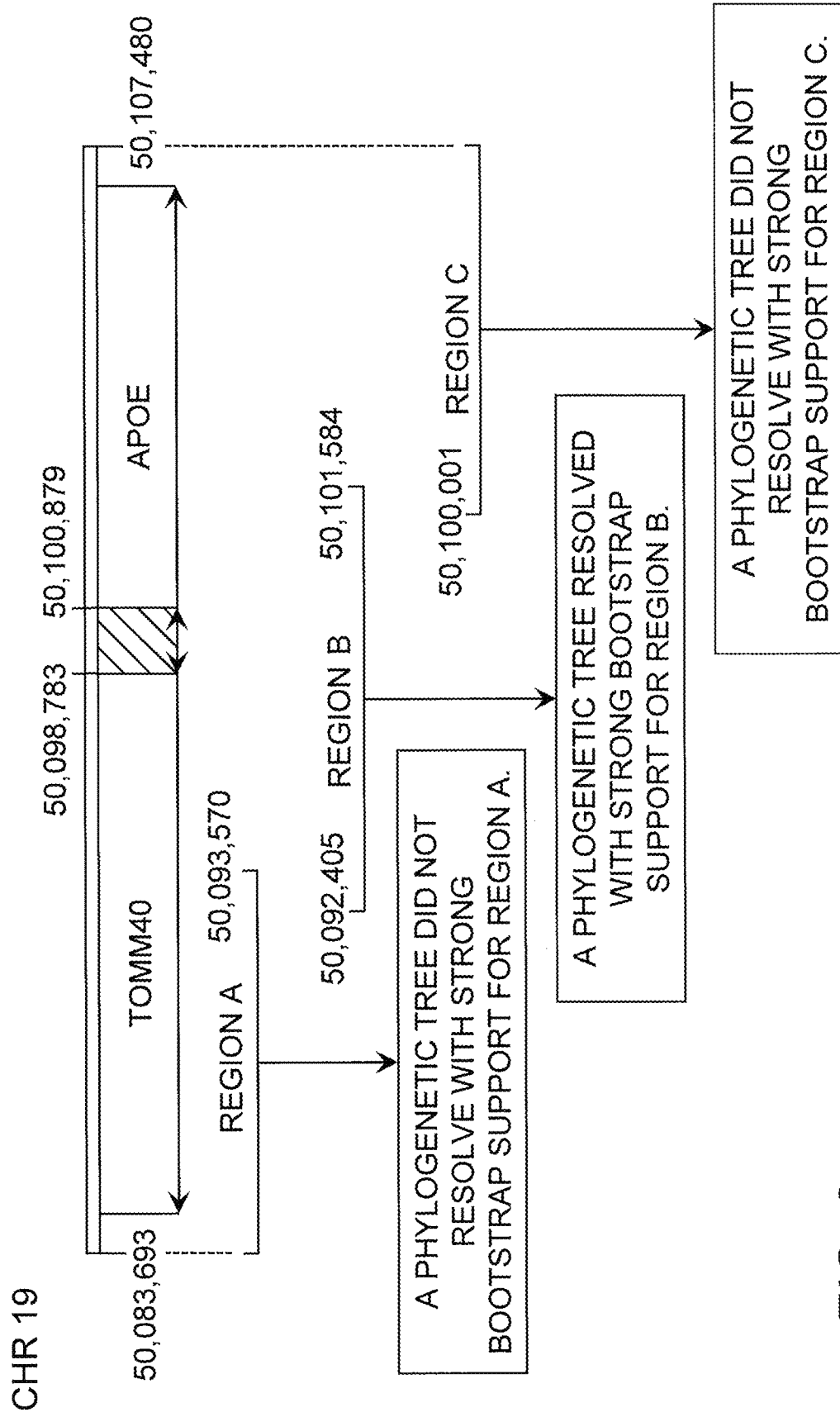
FIG. 3 shows Regions A, B, and C on Chromosome 19, which are exemplary genetic loci of interest. The TOMM40 gene is in close proximity to the ApoE gene and encodes a 40 kD protein directed to the outer mitochondrial membrane. TOMM40 is thought to interact with ApoE directly in regulation of mitochondrial protein import, and a present hypothesis is that the presence of a particular TOMM40 variant(s) exacerbates the increased risk for Alzheimer's disease associated with the dose-dependent presence of the APOE 3 allele.

TOMM40 and ApoE proteins are, therefore, of particular interest for Alzheimer's disease. The TOMM40 and APOE genes are in linkage disequilibrium on chromosome 19. Sequencing of the linkage disequilibrium region in hundreds of disease patients and matched controls, combined with mapping the evolution of genetic variants in TOMM40, identifies the region of particular interest in TOMM40-APOE, as shown in FIG. 3. Phylogenetic data suggest an independent genetic effect from TOMM40 on the development of Alzheimer's disease. These data support the hypothesis that a genetic interaction between APOE and TOMM40 contributes to Alzheimer's disease risk and suggest that mitochondrial dysfunction could be responsible for neuronal cell death occurring over many years and leading to disease.

As detailed herein, the interaction between multiple haplotypes of TOMM40 variants and APOE alleles contribute to Alzheimer's disease pathogenesis; in particular, haplotypes of TOMM40 in linkage to the E 3 allele of APOE contribute to disease pathogenesis. Several of the TOMM40 gene variants evolved only cis-linked to APOE 3. (Similarly, specific TOMM40 variants may have evolved cis-linked to APOE 4 or APOE 2.) Thus, any added genetic effect of the TOMM40 variants that are cis-linked to APOE 3 segregates independently of APOE 4 but the two variant protein products, ApoE and Tom40, may functionally interact, in trans, to produce a given observable phenotype or trait. This "coincidence" of adjacent interacting genes may account for the extraordinarily significant statistical association signal for this genomic region found in all Alzheimer's disease genome-wide association scanning studies. It is of interest to note that the initial commercially available genome-wide association scanning platforms did not contain any APOE polymorphisms, but the disease associations were identified with TOMM40 and ApoC1 SNPs—but the region is virtually always referred to as the "APOE region."

These data, which combine disease genetics and putative molecular mechanisms of pathogenesis, can also be viewed within a pharmacogenetics context. Because of the strong genetic effect of inheriting an ApoE 4 allele, ApoE 4 has been referred to as a complex susceptibility gene for more than a decade. Consistent replications of the age of onset distributions as a function of ApoE genotype confirm that the role of ApoE 3 inheritance is not totally benign, but it has been viewed as a lower risk factor than inheritance of APOE 4 and is observed as a later disease onset. There are genetic variants of TOMM40 that are located only on DNA strands containing ApoE 3 in the linkage disequilibrium regions (Roses et al., The Pharmacogenomics Journal (2010) 10, 375-384), and thus not in Hardy-Weinberg equilibrium as was required for SNPs in genome-wide association panels. Evolutionary changes in TOMM40 sequences that are cis-linked only to ApoE 3 act to increase the risk of Alzheimer's disease associated with ApoE 3, while other variants of TOMM40 cis-linked to ApoE 3 decrease the risk associated with ApoE 3. An independent genetic test would be to determine whether those TOMM40 polymorphisms associated with less Alzheimer's disease segregate at a later age in age of onset distribution plots for ApoE 3 containing genotypes [ApoE 3/3 or ApoE 4/3].

Detecting the presence or absence of APOE 2, 3 or 4, and/or TOMM40 haplotypes or of DNA encoding the same (including, in some embodiments, the number of alleles for each) in a subject may be carried out either directly or indirectly by any suitable means. A variety of techniques are known to those skilled in the art. All generally involve the step of collecting a sample of biological material containing nucleic acid and/or protein from the subject, and then detecting whether or not the subject possesses the haplotype of interest. The detecting step with respect to ApoE, for example, may also be carried out by collecting an ApoE sample from the subject (for example, from cerebrospinal fluid, or any other fluid or tissue containing ApoE), and then determining the presence or absence of an ApoE 2, 3, or 4 isoform in the ApoE sample (e.g., by isoelectric focusing or immunoassay).

Determining the presence or absence of DNA encoding an ApoE and/or TOMM40 isoform may be carried out by direct sequencing of the genomic DNA region of interest, with an oligonucleotide probe labeled with a suitable detectable group, and/or by means of an amplification reaction such as a polymerase chain reaction or ligase chain reaction (the product of which amplification reaction may then be detected with a labeled oligonucleotide probe or a number of other techniques). In embodiments in which an insertion/deletion polymorphism is determined, detection can also be performed by making use of assays that detect the relative length of the relevant portion of genomic DNA (e.g., by electrophoresis). Further, the detecting step may include the step of detecting whether the subject is heterozygous or homozygous for the gene encoding an ApoE and/or TOMM40 haplotype. Numerous different oligonucleotide probe assay formats are known which may be employed to carry out the present invention. See, e.g., U.S. Pat. No. 4,302,204 to Wahl et al.; U.S. Pat. No. 4,358,535 to Falkow et al.; U.S. Pat. No. 4,563,419 to Ranki et al.; and U.S. Pat. No. 4,994,373 to Stavrianopoulos et al. (applicants specifically intend that the disclosures of all U.S. Patent references cited herein be incorporated herein by reference).

In some embodiments, detection may include multiplex amplification of the DNA (e.g., allele-specific fluorescent PCR). In some embodiments, detection may include hybridization to a microarray (a chip, beads, etc.). In some embodiments, detection may include sequencing appropriate portions of the gene containing the haplotypes sought to be detected. In some embodiments, haplotypes that change susceptibility to digestion by one or more endonuclease restriction enzymes may be used for detection. For example, restriction fragment length polymorphism (RFLP), which refers to the digestion pattern when various restriction enzymes are applied to DNA, may be used. In some embodiments, the presence of one or more haplotypes can be determined by allele specific amplification. In some embodiments, the presence of haplotypes can be determined by primer extension. In some embodiments, the presence of haplotypes can be determined by oligonucleotide ligation. In some embodiments, the presence of haplotypes can be determined by hybridization with a detectably labeled probe. See, e.g., U.S. Patent Application Publication No. 2008/0153088 to Sun et al.; Kobler et al., Identification of an 11T allele in the polypyrimidine tract of intron 8 of the CFTR gene, Genetics in Medicine 8(2):125-8 (2006); Costa et al., Multiplex Allele-Specific Fluorescent PCR for Haplotyping the IVS8 (TG)m(T)n Locus in the CFTR Gene, Clin. Chem., 54:1564-1567 (2008); Johnson et al., A Comparative Study of Five Technologically Diverse CFTR Testing Platforms, J. Mol. Diagnostics, 9(3) (2007); Pratt et al., Development of Genomic Reference Materials for Cystic Fibrosis Genetic Testing, J. Mol. Diagnostics, 11:186-193 (2009).

Amplification of a selected, or target, nucleic acid sequence may be carried out by any suitable means on DNA isolated from biological samples. See generally D. Kwoh and T. Kwoh, 1990. Examples of suitable amplification techniques include, but are not limited to, polymerase chain reaction, ligase chain reaction, strand displacement amplification (see generally Walker et al., 1992a; Walker et al., 1992b), transcription-based amplification (see Kwoh et al., 1989), self-sustained sequence replication (or "3SR") (see Guatelli et al., 1990), the Qβ replicase system (see Lizardi et al., 1988), nucleic acid sequence-based amplification (or "NASBA") (see Lewis, 1992), the repair chain reaction (or "RCR") (see Lewis, supra), and boomerang DNA amplification (or "BDA") (see Lewis, supra). Polymerase chain reaction is currently preferred.

DNA amplification techniques such as the foregoing can involve the use of a probe, a pair of probes, or two pairs of probes which specifically bind to DNA encoding ApoE 4, but do not bind to DNA encoding ApoE 2 or ApoE 3 under the same hybridization conditions, and which serve as the primer or primers for the amplification of the ApoE 4 DNA or a portion thereof in the amplification reaction. Likewise, one may use a probe, a pair of probes, or two pairs of probes which specifically bind to DNA encoding ApoE 2, but do not bind to DNA encoding ApoE 3 or ApoE 4 under the same hybridization conditions, and which serve as the primer or primers for the amplification of the ApoE 2 DNA or a portion thereof in the amplification reaction; and one may use a probe, a pair of probes, or two pairs of probes which specifically bind to DNA encoding ApoE 3, but do not bind to DNA encoding ApoE 2 or ApoE 4 under the same hybridization conditions, and which serve as the primer or primers for the amplification of the ApoE 3 DNA or a portion thereof in the amplification reaction.

Similarly, one may use a probe, a pair of probes, or two pairs of probes which specifically bind to DNA encoding a TOMM40 haplotype of interest, but do not bind to other TOMM40 haplotypes under the same hybridization conditions, and which serve as the primer or primers for the amplification of the TOMM40 DNA or a portion thereof in the amplification reaction.

In general, an oligonucleotide probe which is used to detect DNA encoding ApoE and/or TOMM40 haplotypes is an oligonucleotide probe which binds to DNA encoding the haplotype of interest, but does not bind to DNA encoding other haplotypes under the same hybridization conditions. The oligonucleotide probe is labeled with a suitable detectable group, such as those set forth below in connection with antibodies.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques, or by direct visualization on a gel.

When PCR conditions allow for amplification of all ApoE allelic types, the types can be distinguished by hybridization with allelic specific probe, by restriction endonuclease digestion, by electrophoresis on denaturing gradient gels, or other techniques. A PCR protocol for determining the ApoE genotype is described in Wenham et al. (1991), incorporated by reference herein. Examples of primers effective for amplification and identification of the ApoE isoforms are described therein. Primers specific for the ApoE polymorphic region (whether ApoE 4, E3 or E2) can be employed. In Wenham, for example, PCR primers are employed which amplify a 227 bp region of DNA that spans the ApoE polymorphic sites (codons 112 and 158, which contain nucleotides 3745 and 3883). The amplified fragments are then subjected to restriction endonuclease CfoI which provides different restriction fragments from the six possible ApoE genotypes which may be recognizable on an electrophoresis gel. See also, Hixon et al. (1990); Houlston et al. (1989) Wenham et al. (1991); and Konrula et al. (1990) for additional methods, all of which are incorporated by reference herein.

7. Active Agents, Compositions and Treatment.

As noted above, phylogenetic trees created using the methods detailed herein may also be analyzed based upon responsiveness of the condition of interest to treatment with an active agent or treatment method of interest according to some embodiments, and treatment decisions for a subject or patient may be based upon specific genetic variants identified.

Active agents. Active agents include those known for treatment of a condition of interest, and are inclusive of anti-Alzheimer's disease active agents, including, but are not limited to, acetylcholinesterase inhibitors, NMDA receptor antagonists, and peroxisome proliferator-activated receptor (PPAR) agonists or modulators, including but not limited to those drugs in the thiazolidinedione (rosiglitazone and pioglitazone) or glitazar classes. The active agent could also be a biopharmaceutical product, for example an antibody (e.g., monoclonal, polyclonal, derivatives of or modified antibodies such as Domain Antibodies™, Bapineuzumab, etc.), fusion proteins or therapeutic RNA molecules. The active agent could also be a combination of any of these products.

Examples of acetylcholinesterase inhibitors include, but are not limited to, donepezil (commercially available as ARICEPT), galantamine (commercially available as RAZADYNE), and rivastigmine (commercially available as EXELON) and the pharmaceutically acceptable salts thereof. Additional examples include, but are not limited to, those described in U.S. Pat. Nos. 6,303,633; 5,965,569; 5,595,883; 5,574,046; and 5,171,750 (the disclosures of all U.S. Patent references cited herein are to be incorporated by reference herein in their entirety).

Examples of NMDA receptor antagonists include, but are not limited to, memantine (commercially available as AKATINOL, AXURA, EBIXIA/ABIXIA, MEMOX and NAMENDA) and the pharmaceutically acceptable salts thereof. Additional examples include, but are not limited to, those described in U.S. Pat. Nos. 6,956,055; 6,828,462; 6,642,267; 6,432,985; and 5,990126.

Examples of PPAR agonists or modulators include, but are not limited to, glitazones (e.g., troglitazone, pioglitazone, englitazone, MC-555, rosiglitazone, balaglitazone, netoglitazone, ciglitazone, rivoglitazone, and the like), and those without a glitazone structure (e.g., K-111, INT-131, MBX-102 (metaglidisen), MBX-2044, FK614 including SPPARgammaM GSK-376501 and the like). Another is psi-baptigenin (Chemical Biology and Drug Design, 71(1): 57-70 (2008)).

Thiazolidinedione drugs include rosiglitazone (commercially available as AVANDA). Thiazolidinedione compounds related to rosiglitazone, include, but are not limited to: 5-(4-[2-(N-methyl-N-(2-benzothiazolyl)amino)ethoxy]benzyl)-2,4-thiazolidine dione; 5-(4-[2-(N-methyl-N-(2-benzothiazolyl)amino)ethoxy]benzylidene)-2,4-thiazolidinedione; 5-(4-[2-(N-methyl-N-(2-benzoxazolyl)amino)ethoxy]benzylidene)-2,4-thiazolidinedione; 5-(4-[2-(N-methyl-N-(2-benzoxazolyl)amino)ethoxy]benzylidene)-2,4-thiazolidinedione; 5-(4-[2-(N-methyl-N-(2-pyrimidinyl)amino)ethoxy]benzyl)-2,4-thiazolidinedione; 5-(4-[2-(N-methyl-N-(2-pyrimidinyl)amino)ethoxy]benzylidene)-2,4-thiazolidinedione; 5-(4-(2-(N-methyl-N-[2-(4,5-dimethylthiazolyl)]amino)ethoxy]benzyl)-2,4-thiazolidinedione; 5-(4-[2-(N-methyl-N-[2-(4,5-dimethylthiazolyl)]amino)ethoxy]benzylidene)-2,4-thiazolidinedione; 5-(4-[2-(N-methyl-N-(2-thiazolyl)amino)ethoxy]benyl)-2,4-thiazolidinedione; 5-(4-[2-(N-methyl-N-(2-thiazolyl)amino)ethoxy]benzylidene)-2,4-thiazolidinedione; 5-[4-(2-(N-methyl-N-(2-(4-phenylthiazolyl))amino)ethoxy)benzyl]-2,4-thiazolidinedione; 5-(4-[2-(N-methyl-N-(2-(4-phenylthiazolyl))amino)ethoxy]benzylidene)-2,4-thiazolidinedione; 5-(4-[2-(N-methyl-N-[2-(4-phenyl-5-methylthiazolyl)]amino)ethoxy]benzyl)-2,4-thiazolidinedione; 5-(4-[2-(N-methyl-N-[2-(4-phenyl-5-methylthiazoly)]amino)ethoxy]benzylidene)-2,4-thiazolidinedione; 5-(4-[2-(N-methyl-N-[2-(4-methyl-5-phenylthiazolyl)]amino)ethoxy]benzyl)-2,4-thiazolidinedione; 5-(4-[2-(N-methyl-N-[2-(4-methyl-5-phenylthiazolyl)]amino)ethoxy]benzylidene)-2,4-thiazolidinedione; 5-(4-[2-(N-methyl-N-[2-(4-methylthiazolyl)]amino)ethoxy]benzyl)-2,4-thiazolidinedione; 5-(4-[2-(N-methyl-N-[2-(4-methylthiazolyl)]amino) ethoxy]benzylidene)-2,4-thiazolidinedione; 5-[4-(2-(N-methyl-N-[2-(5-phenyloxazolyl)]amino) ethoxy)benzyl]-2,4-thiazolidinedione; 5-(4-[2-(N-methyl-N-[2-(5-phenyloxazolyl)]amino) ethoxy]benzylidene)-2,4-thiazolidinedione; 5-(4-[2-(N-methyl-N-[2-(4,5-dimethyloxazolyl)]amino) ethoxy]benzyl)-2,4-thiazolidinedione; 5-(4-[2-(N-methyl-N-[2-(4,5-dimethyloxazolyl)]amino)ethoxy]benzylidene)-2,4-thiazolidinedione; 5-[4-(2-(2-pyrimidinylamino)ethoxy)benzyl]-2,4-thiazolidinedione; 5-[4-(2-(2-pyrimidinylamino)ethoxy)benzylidene]-2,4-thiazolidinedione; 5-(4-[2-(N-acetyl-N-(2-pyrimidinyl)amino)ethoxy]benzyl)-2,4-thiazolidinedione; 5-(4-(2-(N-(2-benzothiazolyl)-N-benzylamino)ethoxy) benzylidene)-2,4-thiazolidinedione; 5-(4-(2-(N-(2-benzothiazolyl)-N-benzylamino)ethoxy) benzyl)-2,4-thiazolidinedione; 5-(4-[3-(N-methyl-N-(2-benzoxazolyl)amino)propoxy]benzyl)-2,4-thiazolidinedione; 5-(4-[3-(N-methyl-N-(2-benzoxazolyl)amino)propoxy]benzylidene)-2,4-thiazolidinedione; 5-(4-[2-(N-methyl-N-(2-pyridyl)amino) ethoxy]benzyl)-2,4-thiazolidinedione; 5-(4-[2-(N-methyl-N-(2-pyridyl)amino)ethoxy]benzylidene)-2,4-thiazolidinedione; 5-(4-[4-(N-methyl-N-(2-benzoxazolyl) amino)butoxy]benzylidene)-2,4-thiazolidinedione; 5-(4-[4-(N-methyl-N-(2-benzoxazolyl)amino)butoxy]benzyl)-2,4-thiazolidinedione; 5-(4-[2-(N-(2-benzoxazolyl)amino) ethoxy]benzylidene)2,4-thiazolidinedione; 5-(4-[2-(N-(2-benzoxazolyl)amino)ethoxy]benzyl)-2,4-thiazolidinedione; 5-(4-[2-(N-isopropyl-N-(2-benzoxazolyl)amino)ethoxy] benzyl)-2,4-thiazolidinedione, and pharmaceutically acceptable salts thereof. See, e.g., U.S. Pat. No. 5,002,953.

Thiazolidinedione drugs also include pioglitazone ((±)-5 [p-[2-(5-ethyl-2-pyridyl)ethoxy]benzyl]-2,4-thiazolidinedione, or a salt, solvate, co-crystal, polymorphic forms and optical isomers thereof) (commercially available as ACTOS). Thiazolidinedione compounds include, but are not limited to, 5-{4-[2-(5-ethyl-2-pyridyl)ethoxy]benzyl}-2,4-thiazolidinedione, 5-{4-[2-(6-ethyl-2-pyridyl)ethoxy]benzyl}-2,4-thiazolidinedione, 5-(4-(2-(3-ethyl-2-pyridyl)ethoxy)benzyl]-2,4-thiazolidinedione, 5-(4-(2-(4-ethyl-2-pyridyl)ethoxy)benzyl)-2,4-thiazolidinedione, 5-(4-(2-(5-ethyl-2-pyridyl)ethoxy)benzyl)-2,4-thiazolidinedione, 5-(4-(2-(6-ethyl-2-pyridyl)ethoxy)benzyl)-2,4-thiazolidinedione, (R)-(+)-5-(3-(4-(2-(2-furyl)-5-methyl-4-oxazolylmethoxy)-3-methoxyphenyl)propyl)-2,4-oxazolidinedione, 5-((3,4-dihydro-2-(phenylmethyl)-2H-1-benzopyran-6-yl)methyl)-2,4thiazolidinedione, 5-((4-(3-(5-methyl-2-phenyl-4-oxazolyl)-1-oxopropyl)phenyl)methyl)-2,4-thiazolidinedione, 5-(2-(5-methyl-2-phenyl-4-oxazolylmethyl)benzofuran-5-ylmethyl)-2,4-oxazolidinedione, 5-(2-naphthalenylsulfonyl)-2,4- thiazolidinedione, 5-((4-(2-methyl-2-pyridylamino)ethoxy)phenyl)-methyl)-2,4-thiazolidinedione, and pharmaceutically acceptable salts thereof. See U.S. Pat. Nos. 4,687,777 and 5,965,584.

The active agents disclosed herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Active agents can be administered as prodrugs. "Prodrugs" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299. Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. Nos. 6,680,324 and 6,680,322.

Compositions. The active agents described above may be formulated for administration in a pharmaceutical carrier in accordance with known techniques. See, e.g., Remington, *The Science And Practice of Pharmacy* (9$^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound(s), which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active agent(s), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

Dosage. The therapeutically effective dosage of any specific active agent, the use of which is in the scope of present invention, will vary somewhat from compound to compound, and patient to patient, and will depend upon the condition of the patient and the route of delivery. For oral administration, a total daily dosage of from 1, 2 or 3 mg, up to 30, 40 or 50 mg, may be used, given as a single daily dose or divided into two or three daily doses. For example, when administering rosigitazone in accordance with the methods of the present invention, a single daily dose may be the FDA approved dose for Avandia® of 2 mg, 4 mg or 8 mg. By further example, when administering pioglitazone in accordance with the methods of the present invention, a single daily dose may be the FDA approved dose for Actos® of 15 mg, 30 mg or 45 mg.

Treatment. Genetic variants as described herein or discovered using the methods as taught herein may be used to determine the course of treatment of a patient afflicted with a condition (e.g., a condition associated with ApoE and/or TOMM40), by, e.g., determining which active agent and/or course of treatment and/or dosage to administer based upon the presence or absence of the genetic variant or variants. The presence or absence of the genetic variants may indicate efficacy of an active agent and/or course of treatment for the patient, predict age of onset for a condition, indicate preferred dose regimens, etc. A genetic profile may be generated for a patient, and the profile consulted to determine whether the patient is among a group of patients that are likely to be responsive to a particular active agent.

Instructions for use may be packaged with or otherwise associated with an active agent indicating recommendations for treatment, time to treatment, dose regimens, etc., based upon the presence or absence of the genetic variants.

8. Methods of Determining a Prediction of Disease Risk or a Prognosis.

To determine a prediction of disease risk for a non-symptomatic individual or a prognosis (the prospect of affliction or disease course as anticipated from the usual course of disease or peculiarities of the case) according to some embodiments of the present invention, diagnostic data, including the patient's diagnosis or medical history or age, and genetic data, such as the patient's genotype (e.g., ApoE and/or TOMM40 genotype), may be processed to provide therapeutic options and outcome predictions. Processing may include obtaining a "patient profile" such as the collection of a patient's medical history including age and gender, genotyping of the loci of interest (e.g., using appropriately designed primers and using an RT-PCR or PCR amplification step and/or phenotyping, e.g., using an antibody-mediated method or enzymatic test), and statistical or other analyses that converts this raw data into a prognosis. The prognosis may include a prediction of a patient's age of disease onset, response to drug therapy, time to treatment, treatment efficacy, etc. In some embodiments, the prognosis may include the use of a computer software program to analyze patient data and run statistical cross-checks against relational databases in order to convert the patient data or profile to a prognosis.

A "patient profile" includes data and/or materials pertaining to the patient for whom the predictive and/or prognostic analysis is being performed. Data may include information on the patient's diagnosis, age, gender, and/or genotype. The patient profile may also include materials from the patient such as blood, serum protein samples, cerebrospinal fluid, or purified RNA or DNA.

A physician may choose to prescribe an active agent that treats Alzheimer's disease, cognitive impairment, etc., according to an individual's risk of developing the disease. An individual's risk according to some embodiments is determined by a TOMM40 genotype (e.g., at rs10524523), optionally in conjunction with any of a number of other factors that may include, for example, the individual's age, gender, APOE genotype, cognitive status, brain images (e.g., of atrophy or brain volume generated using magnetic resonance imaging (MM) or metabolic activity assayed by BOLD functional MRI), biochemical markers (e.g. serum or CSF amyloid beta, tau or phospho-tau), etc., or a combination of these factors.

9. Genotype Stratification in Clinical Trials.

Detection of a genotype taught herein or as determined with the methods herein can be used in conducting a clinical trial in like manner as other genotype information is used to conduct a clinical trial, such as described in, e.g., U.S. Pat. Nos. 6,573,049 6,368,797 and 6,291,175.

In some embodiments, such methods advantageously stratify or permit the refinement of the patient population (e.g., by division of the population into one or more subgroups) so that advantages of particular treatment regimens can be more accurately detected, particularly with respect to particular sub-populations of patients with particular genotypes. In some embodiments, such methods comprise administering a test active agent or therapy to a plurality of subjects (a control or placebo therapy typically being administered to a separate but similarly characterized plurality of subjects) and detecting the presence or absence of a genotype (e.g., ApoE and/or TOMM40) as described above in the plurality of subjects. The genotype may be detected before, after, or concurrently with the step of administering the test therapy. The influence of one or more detected alleles on the test therapy can then be determined on any suitable parameter or potential treatment outcome or consequence, including, but not limited to, the efficacy of said therapy, lack of side effects of the therapy, etc.

A clinical trial can be set up to test the efficacy of test compounds to treat any number of diseases for which a particular genotype has been determined to be associated, for subjects who are diagnosed with the disease or are at risk for developing the disease. If subjects are genotyped after the completion of a clinical trial, the analyses may still be aimed at determining a relationship between a treatment for a disease and the allele to be assessed for efficacy. Alternatively, if a symptomatic or asymptomatic subject has not yet been diagnosed with the disease but has been determined to be at risk of developing the disease, a similar clinical trial to the clinical trial described above may be carried out.

The underlying biological mechanisms may also be considered when designing the treatment groups. For example, the ApoE 4 (1-272) fragment binds to mitochondria, decreases mitochondrial cellular dynamics and decreases synaptogenesis more than ApoE 3 (1-272). Rosiglitazone, a drug candidate for the treatment of Alzheimer's disease, increases mitogenesis and increases synaptogenesis—opposing the effects of ApoE fragment binding—for ApoE 3 greater than with ApoE 4. Therefore, the drug or treatment candidate (e.g., rosiglitazone or pioglitazone) may be selected based upon an underlying mechanism of action as it relates to the genetic markers used for the stratifications (e.g., ApoE 2, E 3, E 4 and/or TOMM40 variants).

Assessment of the efficacy of a drug chosen for the trial may include monitoring the subject over a period of time and analyzing the delay of onset of the disease and the intensity of the disease at the time of onset, as well as measuring the onset of symptoms which are associated with the disease. A drug that, in a clinical trial, eliminates or delays the onset of the disease, or reduces the symptoms of the disease may be a beneficial drug to use in patients diagnosed with the disease or at risk of developing the disease. Test compounds which may be used in such trials include the agents as described above, including those previously approved for clinical use and new compounds not yet approved for use, or approved for treating a particular disease. Thus, in some embodiments the clinical trial may include the optimization of drug administration, including dosage, timing of administration, toxicities or side effects, route of administration, formulation, and efficacy of the treatment.

10. Kits Useful for the Detection of Genotype Variants at Loci of Interest and/or Determining Treatment.

Kits for determining if a subject is at increased risk of developing a disease, developing a disease at an earlier age of onset, and/or a candidate for a particular treatment, where the disease is associated with ApoE and/or TOMM40 (e.g., late onset Alzheimer's disease), are provided herein. The kits include at least one reagent specific for detecting for the presence or absence of an ApoE and/or TOMM40 variant as described herein, and may include instructions to aid in determining whether the subject is at increased risk of developing the disease. The kit may optionally include a nucleic acid for detection of an ApoE gene (e.g., ApoE 2, ApoE 3 and/or ApoE 4) or instructions for isoelectric focusing methods for detecting the ApoE genotype; and/or a nucleic acid or multiple nucleic acids for detection of a TOMM40 variant (e.g., the length of a TOMM40 variant) as described herein. In some embodiments, the kit may optionally include one or more antibodies which binds to ApoE 2, ApoE 3, ApoE 4, or to isoforms of TOMM40. The test kit may be packaged in any suitable manner, typically with all elements in a single container along with a sheet of printed instructions for carrying out the test.

In some embodiments, the kit may optionally contain buffers, enzymes, and reagents for amplifying the genomic nucleic acids via primer-directed amplification. The kit also may include one or more devices for detecting the presence or absence of particular haplotypes in the amplified nucleic acid. Such devices may include one or more probes that hybridize to a haplotype nucleic acid, which may be attached to a bio-chip or microarray device, such as any of those described in U.S. Pat. No. 6,355,429. The bio-chip or microarray device optionally has at least one capture probe attached to a surface that can hybridize to a haplotype sequence. In preferred embodiments, the bio-chip or microarray contains multiple probes, and most preferably contains at least one probe for a haplotype sequence which, if present, would be amplified by a set of flanking primers. For example, if five pairs of flanking primers are used for amplification, the device would contain at least one haplotype probe for each amplified product, or at least five probes. The kit also preferably includes instructions for using the components of the kit.

The kit may include a device that permits the determination of length of the polyT variant. Such a device may include a microcapillary electrophoresis device such as those described in U.S. Pat. No. 5,112,460 or a component thereof, or a microfluidic electrophoresis device such as those described in U.S. Pat. No. 5,904,824.

11. Computer Program Products Useful for Determining Risk and/or Treatment.

Determining risk and/or treatment for a disease such as Alzheimer's disease according to some embodiments of the present invention may be implemented by computer program instructions for convenient implementation in a clinic. In some embodiments, a user may be prompted to enter specific information about an individual, e.g., one or more of the following: TOMM40 genotype (including, but not limited to, poly-T length at rs10524523, and optionally, for each TOMM40 allele), age, APOE genotype, signs or symptoms of a disease of interest (if present), family history, etc. The data may be processed and a readout provided of relative risk of onset of the disease or symptoms thereof, in the form of a list, chart, etc., and/or may determine a course of treatment for the individual (e.g., what active agent to prescribe, what dosage and administrations, etc.).

In some embodiments, the determining may make use a prospectively validated algorithm, a retrospectively validated algorithm, or a planned retrospectively validated algorithm.

These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the desired operations.

These computer program instructions may also be stored in a computer-readable memory that can direct a computer or other programmable data processing apparatus to function in a particular manner, such that the instructions stored in the computer-readable memory produce an article of manufacture including instructions which implement the operations.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the operations.

Accordingly, the present invention may be embodied in hardware and/or in software (including firmware, resident software, micro-code, etc.). Furthermore, embodiments of the may take the form of a computer program product on a computer-usable and/or computer-readable storage medium having computer-usable or computer-readable program code embodied in the medium for use by or in connection with an instruction execution system. As used herein, a computer-usable or computer-readable medium may be any medium that can contain or store the program for use by or in connection with the instruction execution system, apparatus, or device.

The computer-usable and/or computer-readable medium may be, for example but not limited to, an electronic, magnetic, optical, electromagnetic, infrared, or semiconductor system, apparatus or device. More specific examples (a non-exhaustive list) of the computer-readable medium would include the following: a portable computer diskette, a random access memory (RAM), a read-only memory (ROM), an erasable programmable read-only memory (EPROM or Flash memory), and a portable compact disc read-only memory (CD-ROM).

The present invention is explained in greater detail in the following non-limiting Examples.

Example 1: Construction of Phylogenetic Trees

Figure 2:
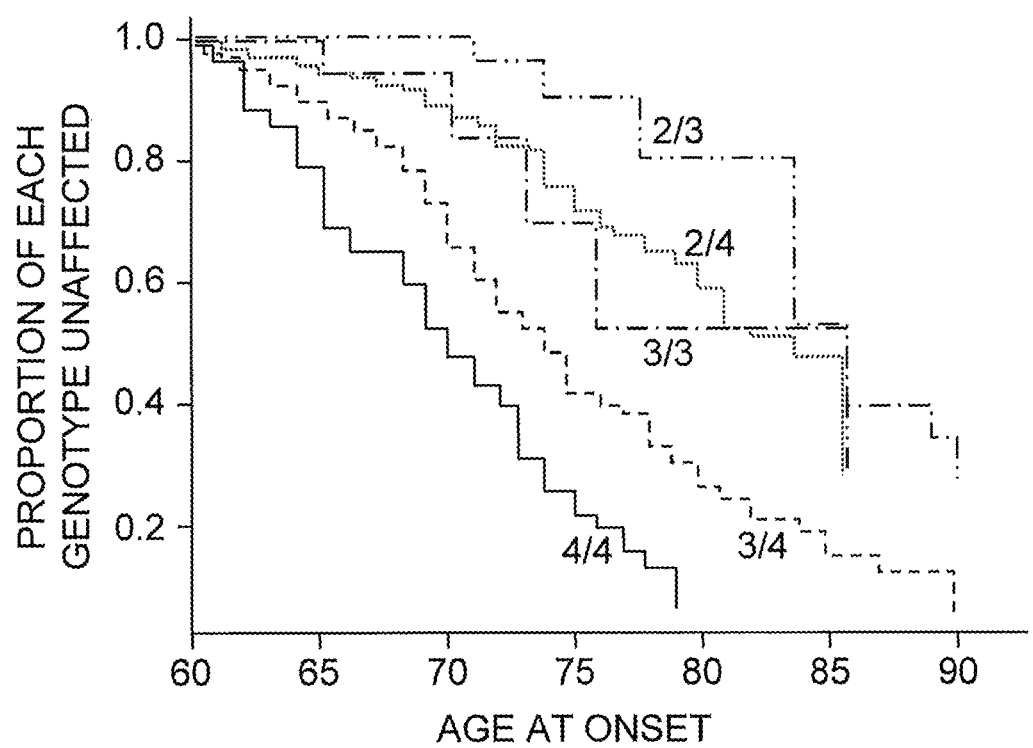
FIG. 2 shows a graph of the mean age of onset of Alzheimer's disease as a function of the inheritance of the five common APOE genotypes, and representing APOE 4 as a risk factor for Alzheimer's disease (1993).

All of the known genome-wide scanning studies demonstrate extremely significant p values around the apolipoproteinC1 [ApoC1] locus. (Mahley et al., Proc. Natl. Acad. Sci. USA 103: 5644-51 (2006), Coon et al., J. Clin. Psychiatry 68: 613-8 (2007); Li et al., Arch. Neurol. 65: 45-53 (2007)). Of equal importance is that each series identified a "favored" borderline significant candidate gene outside of the ApoE linkage disequilibrium area, but these favored candidate genes were different in each study. TOMM40 is near ApoC1 and in linkage disequilibrium with ApoE. Interactions between ApoE 3 or ApoE 4 and different TOMM40 isoforms are believed to be associated with increased or decreased risk of developing Alzheimer's disease within an earlier age range. Age of Alzheimer's disease onset curves for Apo 4/4, 3/4, 3/3, 2/4, and 2/3 genotypes is shown in FIG. 2, indicating a range of risk for earlier development of the disease, depending upon the ApoE profile. ApoE alone does not appear to explain all of the data in these age of onset curves, however.

Various methods for polymorphic profiling of Alzheimer's disease risk associated with the different ApoE alleles have been proposed (see, e.g., U.S. Application of Cox et al., No. 20060228728; U.S. Application of Li and Grupe, No. 20080051318). A phylogenetic approach to the ApoE 4 puzzle is demonstrated herein.

Biological samples, DNA isolation, amplification of loci of interest. A total of 148 subjects included 74 Alzheimer's disease cases and 31 controls in the AS cohort and 40 cases and 33 controls in the DS cohort. All subjects carried the ApoE genotypes previously associated with higher risk for earlier disease onset (i.e. 3/3, 3/4, or 4/4). Biological samples containing DNA were collected from all subjects. Genomic DNA was then isolated according to conventional methods for sequencing of genetic loci on Chromosome 19.

FIG. 3 shows the genetic regions on Chromosome 19 targeted for study using multiple sequence alignment and phylogenetic analysis. The region is encompassed within GenBank reference sequence AF050154. Software was used to generate multiple sequence alignments for variant loci (e.g., ClustalW2, European Bioinformatics Institute). Subsequently, the multiple sequence alignments were analyzed using software for developing phylogenetic trees (e.g., MEGA version 2.1, Center for Evolutionary Functional Genomics, TREEVOLVE, Department of Zoology, University of Oxford, or parsimony-based construction software such as PAUP, Sinauer Associates). Statistical analyses may be performed with, e.g., Genetic Data Analysis (GDA: Software for the Analysis of Discrete Genetic Data, The Bioinformatics Research Center of North Carolina State University). The results of Region B analysis are demonstrated in the phylogenetic tree of FIG. 4.

Figure 4:
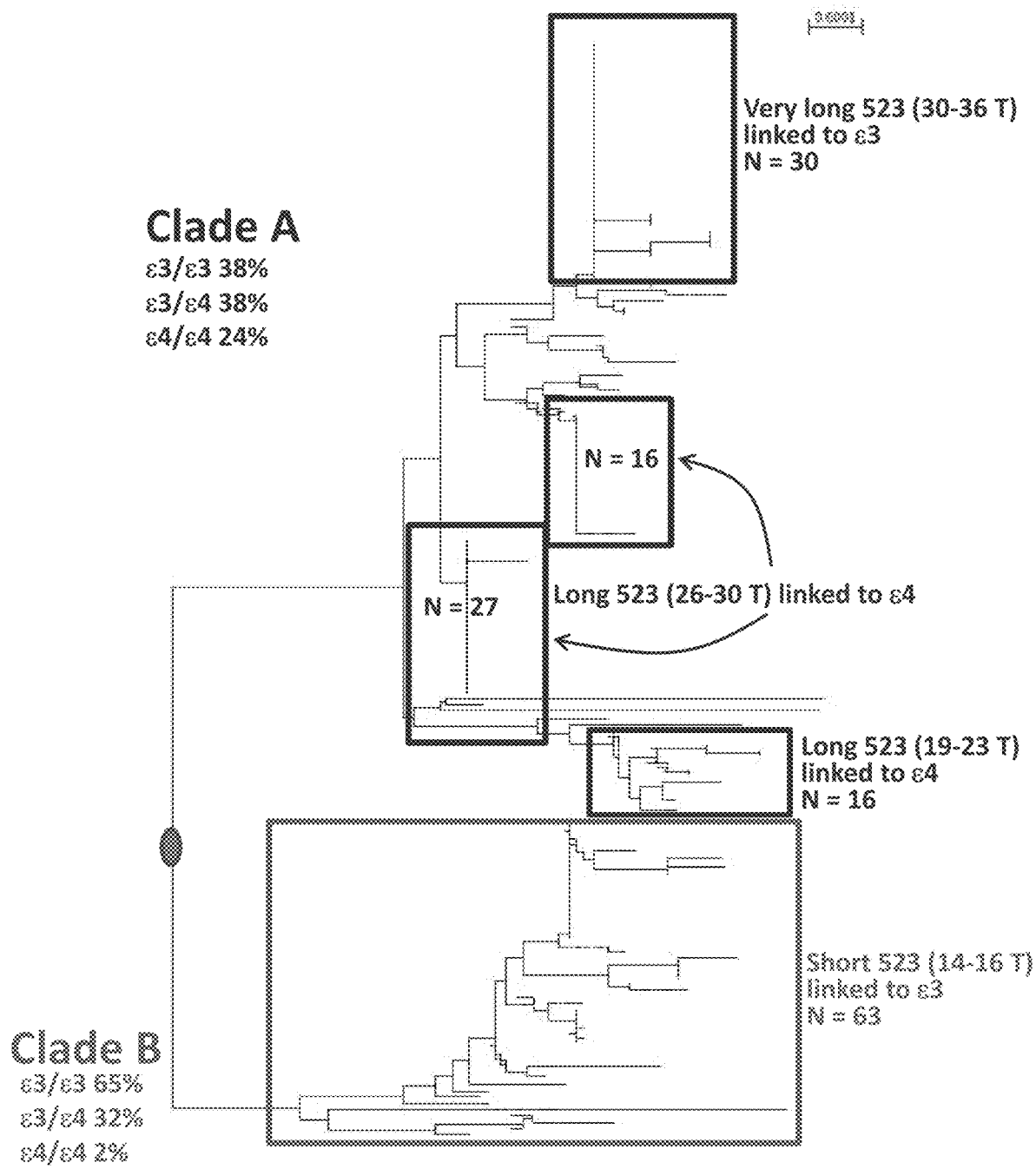
FIG. 4 shows the phylogenetic tree that is formed using the sequence data for the AS case/control cohort of subjects. 'A' and 'B' refer to the two major clades that arise from the first branch point. The lengths of the various alleles of rs10524523 ('523) in each of the terminal clades of this tree are indicated. The APOE allele that is linked in cis to each rs10524523 length allele is also indicated. The number (N) of haplotypes in each square is indicated.

Each piece of data in FIG. 4 represents an observed sequence variant. These variants may be nucleotide substitutions, insertions, deletions, or microsatellites and may or may not result in detectable differences in gene expression or protein function. Each node represents a variant (or a number of variants) that occurs on more than one chromosome. Adjacent nodes define the boundaries of sequences that are in cis, and therefore more likely to be inherited as a unit, in the region of interest on a subject's chromosome. Nodes that precede the greatest number of subsequent nodes represent evolutionarily ancestral variants from which genetic divergence has occurred over time.

The presence of haplotypes or sequence variants corresponding with regions of the tree representing subjects with substantially higher incidence of Alzheimer's disease (i.e., higher ratios of subjects affected with the disease to unaffected control subjects) would mean that the individual subject is also at increased risk. Conversely, substantially lower ratios correspond to reduced risk of developing Alzheimer's disease.

While not wishing to be bound by theory, it is thought that TOMM40 interacts with ApoE directly in regulation of mitochondrial protein import, and a present hypothesis is that the expression of a particular TOMM40 variant(s) exacerbates the relatively moderate risk for Alzheimer's disease associated with the dose-dependent presence of the ApoE 3 allele. Such a TOMM40 variant is discovered within Region B using the methods of the present invention.

Testing new drugs on human subjects carries immense risk (see Kenter and Cohen, Lancet, 368: 1387-91 (2006)). The use of phylogenetic trees to anticipate individual response to a drug or treatment of interest has potential to alleviate that risk significantly. Preliminary studies indicated that rosiglitazone (Avandia) may have genetic-profile specific efficacy in the treatment of Alzheimer's disease (see Risner et al., The Pharmacogenomics Journal 6, 246-254 (2006); Brodbeck et al., Proc. Nat. Acad. Sci. 105, 1343-6 (2008)). Phase II clinical trial data indicate that Alzheimer's disease patients without an ApoE 4 allele responded better to rosiglitazone than patients who carry either 1 or 2 ApoE 4 alleles (data not shown). This supports the hypothesis that variants identified with the methods taught herein may be used to anticipate individual response to treatment based upon genotype.

Example 2: Identification of TOMM40 Variants of Interest 210 sequences (from 105 subjects in the AS cohort) were aligned using the CLUSTAL X program (version 2.0.10, Larkin et al., Clustal W and Clustal X version 2.0. Bioinformatics, 23:2947-2948 (2007)). The multiple sequence alignment was used to construct a phylogenetic tree using a neighbor joining algorithm (Saitou and Nei, The neighbor-joining method: a new method for reconstructing phylogenetic trees. Mol. Evol. Biol., 4:406-425 (1987)) as implemented on the European Bioinformatics Institute (EBI) website.

The resulting phylogenetic tree has a structure of two major clades (A, B) at the first divergence. The ApoE genotype frequencies for these clades are tabulated and shown in FIG. 5. It is clear that group B contains subject-haplotypes of primarily ε3/ε3 and ε3/ε4 ApoE genotypes and almost no ε4/ε4. Clade A contains almost all of the subject haplotypes with the ε4/ε4 genotype.

The list of polymorphisms generated by the SNP discovery platform (Polymorphic) were used to identify specific variants in the TOMM40 gene that separated the data into the two groups. A likelihood ratio test was used to identify significant variants with a p value less than 0.005.

The list of variants is summarized in Table 1. In the table, the term "deletion" is used when the minor allele is a deletion of a nucleotide, and the term "insertion" is used when the minor allele is an addition of a nucleotide. The term "deletion/insertion polymorphism" is used when there are more than two possible forms and the minor allele is not apparent. For example, for the poly-T polymorphisms, there are multiple length polymorphisms observed. The second column of the table provides information on the identities of the specific alleles associated with the variant that divide the sequences into the two groups. For example, T>A indicates that the T allele segregates sequences into group "A" on the phylogenetic tree. When two alleles are listed, e.g. G>B; A>A, each allele uniquely segregates the sequence data into the two groups, while when a single allele is listed it is associated with the predominate separation of the data, and the remaining allele does not uniquely separate the data into a homogenous group, but instead a mixture of both groups.

TABLE 1

TOMM40 variants associated with groups on phylogenetic tree that distribute by ApoE genotype.

| Variant | Allele > tree group | Genomic Location | Function | UCSC Classification |
|---|---|---|---|---|
| 50,092,565 | T > A | 50,092,565 | Intron 6 | single |
| 50,092,587 | T > A | 50,092,587 | Intron 6 | single |
| rs8106922 | G > B; A > A | 50,093,506 | Intron 6 | single |
| rs34896370, rs55821237, rs56290633 | T12_C_T15, T12_C_T16, T13_C_T14_T13_C_T15, T13_C_T16 > A; T14_C_T14, T14_C_T15 > B | 50,093,609 | Intron 6 | complex |
| rs34878901 | T > B; C > A | 50,094,317 | Intron 6 | single |
| rs35568738 | C > B | 50,094,558 | Intron 6 | single |
| rs10602329 | T16, 17, 18 > A T14, 15 > B | 50,094,716 | Intron 6 | insertion/deletion |
| 50,094,733 | ->A | 50,094,733 | Intron 7 | insertion |
| rs10524523 | T12, 14, 15, 16, 17 > B T19, T20, T21, 22, 26, 27, 28, 29, 30, 31, 32, 33, 34 35, 36 > A | 50,094,889 | Intron 6 | insertion/deletion |
| rs1160985 | T > B; C > A | 50,095,252 | Intron 6 | single |
| 50,095,056 | T > A | 50,095,506 | Intron 6 | single |
| rs760136 | A > A; G > B | 50,095,698 | Intron 6 | single |
| rs1160984 | T > B | 50,095,764 | Intron 6 | single |
| rs741780 | C > B; T > A | 50,096,271 | Intron 8 | single |
| rs405697 | A > A | 50,096,531 | Intron 9 | single |
| 50,096,647 (DIP3) | ->A | 50,096,647 | Intron 9 | deletion |
| 50,096,697 | C > A | 50,096,697 | Intron 9 | single |
| rs1038025 | C > B; T > A | 50,096,812 | Intron 9 | single |
| rs1038026 | G > B; A > A | 50,096,902 | Intron 9 | single |
| rs1305062 | C > B; G > A | 50,097,361 | Intron 9 | single |
| rs34215622 | G > B; ->A | 50,098,378 | Exon 10 | insertion |
| rs10119 | A > A | 50,098,513 | Exon 10 | single |
| rs7259620 | G > A; A > B | 50,099,628 | unknown | single |

Example 3: Two Distinct Forms of ApoE 3: those Linked to TOMM40 Haplotypes that Increase Risk and Decrease Age of Onset, and those that Decrease Risk The association of apolipoprotein E (ApoE) genotypes, particularly ApoE ε4 (ApoE 4), with the risk and age of onset of Alzheimer's disease (AD) remains the most confirmed genetic association for any complex disease. Estimates of the heritability of ApoE 4 for late onset AD range from 58% to 79%, and the population attributable risk due to the ApoE 4 allele is between 20% and 70%. These estimates suggest that other genetic variants and/or interactions between variants incur additional disease risk and modify age of onset distributions.

Genome wide scan association results for AD have consistently reproduced the extraordinary Alzheimer's disease association of the LD region containing ApoE. TOMM40, the protein translocase of the outer mitochondrial membrane, is in high LD with ApoE, and codes for the membrane channel through which cytoplasmic peptides and proteins traverse in order to synthesize new mitochondria. Our objectives were to identify additional haplotypes within the LD region that increase the estimates of heritability.

Methods: We examined the LD region containing both ApoE and TOMM40 using deep (10×) primary sequencing in AD patients and controls. We performed phylogenetic analyses of the LD region covering TOMM40 and ApoE in 74 Alzheimer's disease cases and 31 age-matched, unaffected controls with respect to disease risk. Age of onset distribution was also analyzed.

Conclusion: We found that unique and distinct inherited families of different TOMM40 variants are located on the same genomic interval as ApoE 3, versus different and distinct TOMM40 variants on the ApoE 4-containing genomic interval, and can either increase or decrease the age of risk distribution of AD. Therefore, the genetic inheritance of these APOE3-linked TOMM40 variants are independent of the inheritance of ApoE 4, effectively providing a differentiation of two distinct forms of ApoE 3: those linked to TOMM40 haplotypes that increase risk and decrease age of onset of disease, and those that decrease risk and increase age of onset. These data increase the accuracy of genetic age of onset risk, dependent on age, ApoE and TOMM40 genotypes and provide the opportunity to define high risk of AD over the next 5-7 years, versus lower risk of AD.

Example 4: Analysis of Three Identified TOMM40 DIP Variants

Three of the TOMM40 variants identified in this application are deletion/insertion polymorphisms (DIPs) located in intron 6 or intron 9. These DIPs are identified as rs10524523 and rs10602329 in the National Center for Biotechnology Information dbSNP database, and a previously undescribed polymorphism, designated as DIP3. These polymorphisms are located at chr19:50,094,889, chr19:50,094,731, and chr19:50,096,647, respectively, according to NCBI build 36. This invention describes the identification of these DIPs using phylogenetic analysis of the TOMM40 gene, specifically of a 10 Kb fragment of the gene, and that the DIPs are associated with different evolutionary groups determined by phylogenetic analysis. This invention further discloses the utility of these DIPs for (1) determining risk of a healthy person for developing Alzheimer's disease in the future, and (2) for predicting age of onset of AD within an approximately 8 year time-frame.

The three DIP polymorphisms characterized herein correspond to different lengths of DIP poly-T repeats in the TOMM40 gene. The association of DIP poly-T variants with disease risk has precedence. For example a poly-T variant in intron 8 of the cystic fibrosis transmembrane conductance regulator (CFTR) gene is associated with skipping of exon 9 and the development of cystic fibrosis (Groman et al., Am J Hum Genet 74(1):176-9 (2004)). Herein is disclosed: (1) use of the novel method—phylogenetic association analysis (described above)—to identify DIPs that are predictive of disease risk and/or differences in age of disease onset, (2) the identity of three specific DIPs associated with differences in AD age of onset and AD risk, (3) the use of these DIPs individually, together, or with other sequence variants in TOMM40 or ApoE to diagnose disease or predict or determine disease characteristics such as age of disease onset, disease prognosis, disease sub-types, disease severity, and also to analyze or determine the response to drugs.

Figure 5:
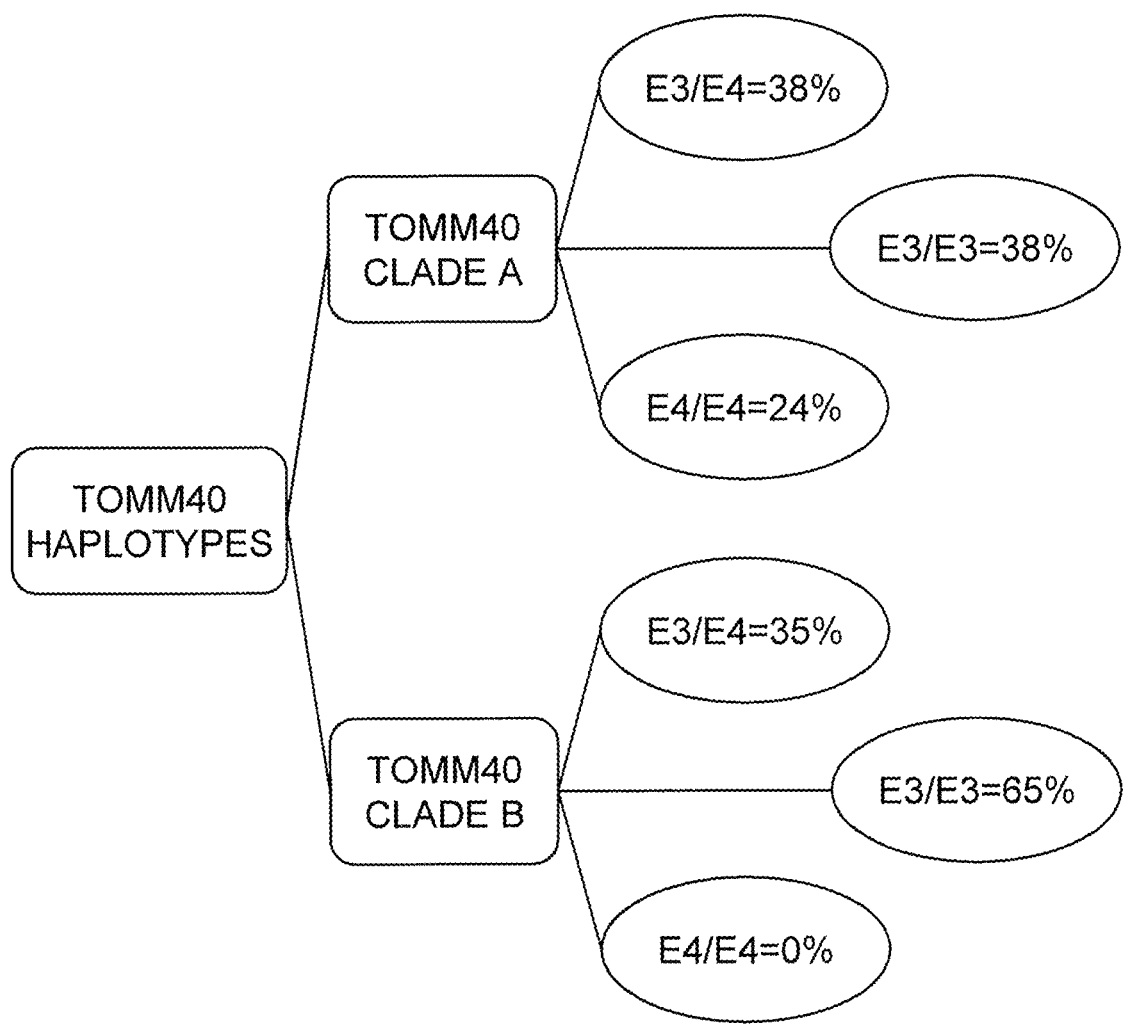
FIG. 5 is a schematic diagram of the phylogenetic tree based on Region B constructed for TOMM40, showing the percentages of the APOE genotypes comprising each of the two major groupings, or clades, of the TOMM40 variants in this region.
Figure 6:
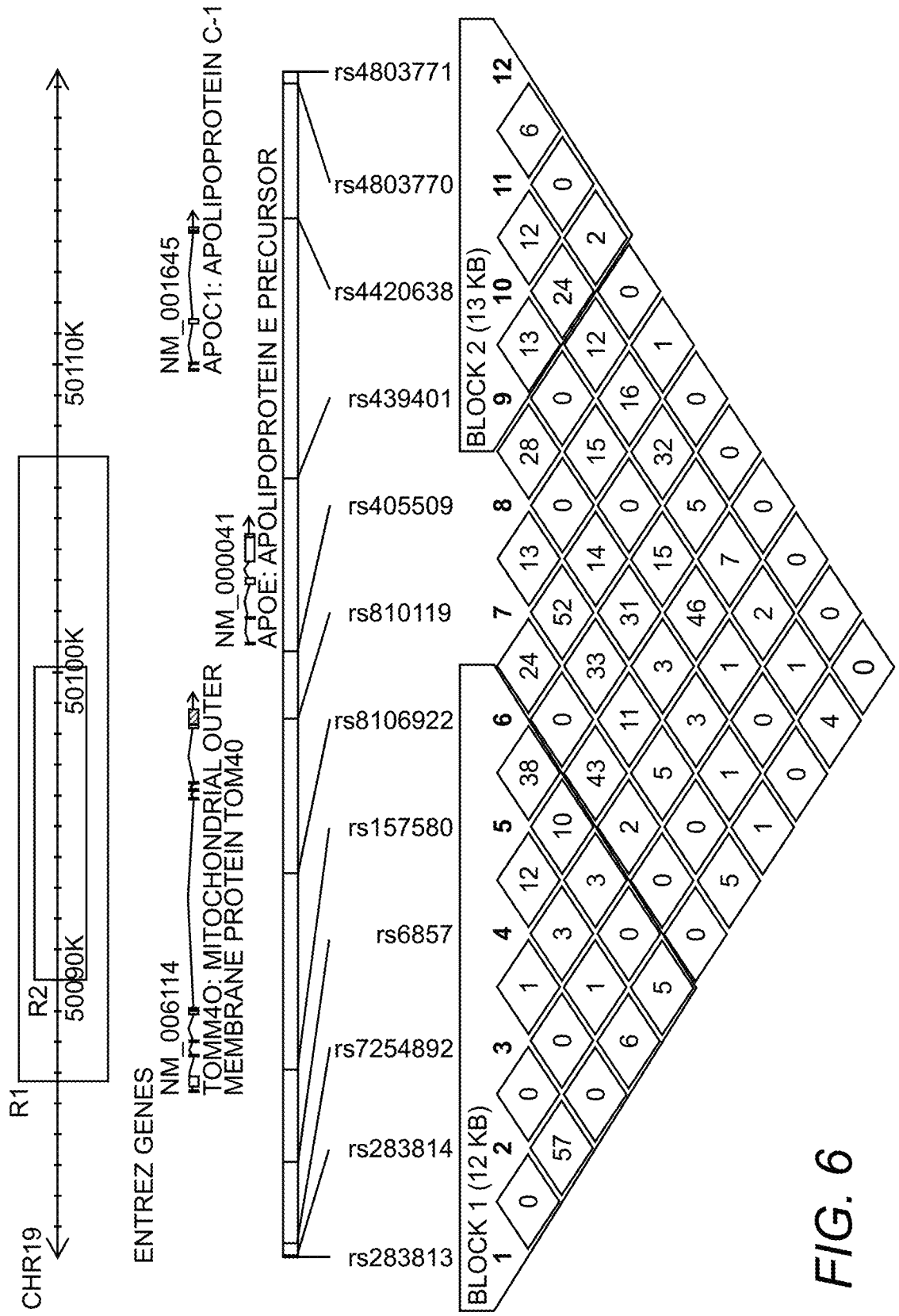
FIG. 6 is a schematic overview of the TOMM40 APOE locus including an LD plot showing haplotype blocks and regions subject to primary sequencing in the exploratory (R1) (23 Kb) and confirmatory (R2) (10 Kb) studies (NCBI Build 36.3). The LD plot is shown for Hapmap data (CEU analysis panel), solid spine haplotype block definition, and $r^2$ values.

Phylogenetic analysis reveals the distribution of rs10524523 and rs10602329 DIPs into two different clades. This analysis reveals that shorter poly-T lengths at these loci map to the phylogenetically-identified clades in group B, the group that also comprises higher percentages of ApoE e3/e3 genotype subjects, effectively few (0%) ApoE e4/e4 subjects and lower case/control ratios (i.e., lower AD disease risk) (FIG. 5). The association between DIP length and phylogenetic group is statistically significant (p<0.0001) by the likelihood ratio test or Pearson Chi-square test.

Due to the genomic architecture, the high linkage disequilibrium and the evolutionary relationships as indicated the phylogenetic analysis, between the two genes, and the putative physical interaction between the two gene products, the influence of TOMM40 genotype is likely to extend to other diseases that are influenced by ApoE genotype. These diseases include, but are not limited to, Parkinson's disease, Multiple sclerosis, cardiovascular disease, dyslipidemia, recovery from traumatic brain injury, recovery from brain ischemic events, response to anaesthetics, and response to drugs used to treat AD and the diseases listed here. These polymorphisms could also be used to, prospectively or retrospectively, stratify subjects in a clinical trial.

These polymorphisms could also be used in drug discovery efforts for the screening of compounds useful for treating diseases influenced by variations in TOMM40 or ApoE protein or gene variants.

In addition, the variants may influence or determine therapies based on specifically targeted biopharmaceuticals as exemplified by monoclonal antibodies and siRNA molecules.

The DIP polymorphisms in TOMM40 that are disclosed herein can be identified from an individual's DNA sample using many different molecular nucleotide analysis methodologies, including, but not limited to, DNA sequencing with the primers denoted in Table 4 listed below.

Example 5: Longer Poly-T Tracts at rs10524523 are Significantly Associated with Earlier Age of Onset of LOAD Phylogenetic analysis has been used to identify genomic relationships between low frequency genetic variants and to cluster evolutionarily related haplotypes (Hahn et al. Population genetic and phylogenetic evidence for positive selection on regulatory mutations at the factor VII locus in humans. Genetics 167, 867-77 (2004)). This methodology was employed to explore the ApoE-TOMM40 LD block for the existence of novel risk determinants for late-onset Alzheimer's disease (LOAD). In an exploratory study, 23 Kb of DNA containing the TOMM40 and ApoE genes were amplified and sequenced, and phase-resolved haplotypes were determined, for 83 LOAD cases and 67 age-matched controls (Li et al. Candidate single-nucleotide polymorphisms from a genome-wide association study of Alzheimer disease. Arch Neurol 65, 45-53 (2008)). It was possible to construct a distinct phylogenetic tree for 10 Kb, encoding exons 2-10, of this region. Two clades (A and B) were distinguished with strong bootstrap support (98%, 1000 replicates). There was a significant difference in the distribution of the ApoE genotypes between the two clades of TOMM40 haplotypes on this phylogenetic tree, suggesting that this region could be functionally significant. Both clades contained subjects with the ε3/ε3 genotype, but 98% of all clade B haplotypes occurred in cis with the ApoE ε3 allele ($P=1.2 \times 10^{-18}$, Fisher's exact test, two-tailed).

The phylogenetic structure of this 10 Kb region of TOMM40, the ApoE ε3-specific inheritance of particular haplotypes, and the identify of the clade-specific polymorphisms were subsequently confirmed in two independent LOAD case/control cohorts, including one cohort with autopsy-confirmed AD status and age of disease onset data. The association between the two clades and disease risk and age of disease onset, where the data was available, was also explored for these two cohorts. The first cohort (AS) comprised AD cases (n=74) and controls (n=31) ascertained at the Arizona Alzheimer's Disease Research Center (ADRC). The second cohort (DS) was assembled at the Duke Bryan ADRC and comprised ApoE ε3/ε4 subjects only (40 autopsy-confirmed cases with known age of disease onset and 33 controls) (Table 2). Although DNA sequencing was successful for a subset of the DS cohort who had disease onset from 50 to 68 years of age, association analyses were limited to a subset of patients who developed AD after the age of 60.

TABLE 2

Cohort compositions. The number of cases and controls, mean age, and percentage that are female are shown for each series. Mean age is given as age-at-diagnosis of AD for cases and age-at-examination for controls. The standard deviation from the mean is given in parenthesis.

| Series | n | | Mean Age (SD) | | % Females | |
|---|---|---|---|---|---|---|
| | Cases | Controls | Cases | Controls | Cases | Controls |
| AS | 74 | 31 | 81.7 (8.01) | 77 (8.93) | 56.3 | 46.7 |
| DS | 40 | 33 | 69.3 (8.3) | 71.9 (7.5) | 70 | 66.7 |

A phylogenetic tree of similar structure to that generated in the exploratory study was developed with strong bootstrap support (97%, 1000 replicates) for the AS cohort. ApoE ε4/ε4 subjects occurred only in clade A (98% separation between groups, $P=2.0\times10^{-4}$ Fisher's exact test, two-tailed), while the remaining ApoE genotypes were distributed between clades A and B. (FIG. 5). That is, ApoE ε4 was always in LD with clade A variants whereas ApoE ε3 occurred in both clade A and clade B haplotypes. Examination of the distribution of the few ApoE ε2/ε4 subjects on the phylogenetic tree suggests that ApoE ε2-TOMM40 haplotypes share a similar evolutionary history with ApoEε3-TOMM40 haplotypes (data not shown). To verify the phylogenetic structure using a separate method, and to ensure that recombination within the genetic interval did not confound the phylogenetic tree structure developed for the AS cohort, haplotype networks were also constructed using statistical parsimony (TCS version 1.21 (Clement et al. TCS: a computer program to estimate gene genealogies. *Mol Ecol* 9, 1657-9 (2000))). The major subject-haplotype clusters derived from the two methods (maximum parsimony and TCS) were congruent.

Clade A was more frequently associated with AD cases than was clade B (OR=1.44, 95% CI=0.76-2.70). ApoE ε3/ε4 heterozygotes (n=36) were analyzed to estimate disease risk associated with clade A haplotypes while controlling for the effect of ApoE ε4. There was a trend to higher incidence of LOAD for the subset that was homozygous for TOMM40 clade A relative to the subset that was heterozygous for clade A and clade B (OR=1.36, 95% CI=0.40-4.61) and thus it was postulated that at least some of the TOMM40 variants which define clade A confer ApoE ε4-independent risk of LOAD.

Analysis of the AS cohort sequence data identified 39 polymorphic sites in the TOMM40 10 Kb region, of which there were 30 parsimony-informative sites (at least two different nucleotides, each represented in at least two sequences). Of the 30 parsimony-informative sites, 18 had a minor allele frequency (MAF)>0.10 and six SNPs were outside the boundary of the TOMM40 gene (FIG. 7A). 10 SNPs occurred exclusively in the context of ApoE ε3 ($P=6.07\times10^{-50}$, Fisher's exact test, two-tailed, n=210) and were never observed in ApoE ε4/ε4 homozygous subjects (n=16). The majority of the ε3-specific TOMM40 variants were located in intronic regions.

Figure 7B:
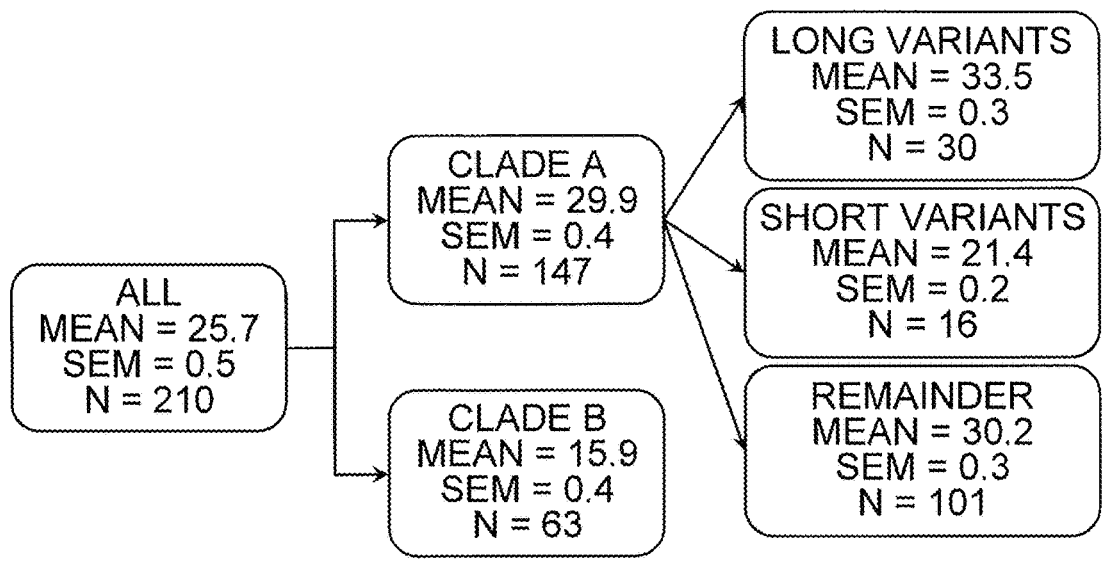

FIG. 7B gives descriptive statistics for the rs10524523 polyT length polymorphism in clades A and B for the AS cohort. Table 3 lists the SNPs that were tested individually and as haplotypes for association with LOAD risk. The odds ratios for disease risk for each clade B distinguishing SNP, in all cases the minor allele, suggest that the clade B alleles are protective of AD risk in the AS cohort, however, in each case the association narrowly missed significance. To account for the effect of ApoE ε4 on the odds ratios reported in Table 3, a balanced set of 48 AD cases and 48 AD controls was constructed by selecting sequences at random from ApoE ε3/ε4 subjects from the pooled AS and DS cohorts. Single SNPs again were not significantly associated with LOAD in this balanced data set. However, the minor alleles of four of the SNPs (r58106922, rs1160985, rs760136, r5741780) that distinguish TOMM40 clade B were assayed previously in three LOAD case/control genome-wide association studies and were found to be protective of disease risk (OR<1 in each case), which is consistent with the trend observed in our study (Abraham et al. A genome-wide association study for late-onset Alzheimer's disease using DNA pooling. *BMC Med Genomics* 1, 44 (2008); Carrasquillo et al. Genetic variation in PCDH11X is associated with susceptibility to late-onset Alzheimer's disease. *Nat Genet* 41, 192-198 (2009); Takei et al. Genetic association study on in and around the ApoE in late-onset Alzheimer disease in Japanese. Genomics 93, 441-448 (2009)).

TABLE 3

Descriptive statistics and allelic and genotypic association results for the individual SNPs.

| SNP ID | Position | Allele | clade B allele | MAF (all) | MAF (cases) | MAF (controls) | LOAD (M) | LOAD (m) | Control (M) | Control (m) |
|---|---|---|---|---|---|---|---|---|---|---|
| All ApoE genotypes | | | | | | | | | | |
| rs1038025 | 50096812 | T/c | c | 0.31 | 0.28 | 0.37 | 106 | 41 | 39 | 23 |
| rs1038026 | 50096902 | A/g | g | 0.31 | 0.28 | 0.37 | 106 | 41 | 39 | 23 |
| rs1160985 | 50095252 | C/t | t | 0.30 | 0.28 | 0.37 | 107 | 41 | 39 | 23 |
| rs1305062 | 50097361 | G/c | c | 0.28 | 0.26 | 0.31 | 106 | 38 | 43 | 19 |
| rs34215622 | 50098378 | —/g | g | 0.28 | 0.26 | 0.34 | 110 | 38 | 40 | 21 |
| rs34878901 | 50094317 | C/t | t | 0.26 | 0.25 | 0.28 | 105 | 35 | 44 | 17 |
| rs7259620 | 50099628 | G/a | a | 0.30 | 0.27 | 0.37 | 108 | 40 | 39 | 23 |
| rs741780 | 50096271 | T/c | c | 0.30 | 0.28 | 0.37 | 107 | 41 | 39 | 23 |
| rs760136 | 50095698 | A/g | g | 0.30 | 0.28 | 0.37 | 107 | 41 | 39 | 23 |
| rs8106922 | 50093506 | A/g | g | 0.28 | 0.26 | 0.31 | 109 | 39 | 43 | 19 |

TABLE 3-continued

Descriptive statistics and allelic and genotypic association results for the individual SNPs.

| | | | | | | | | | | | |
|---|---|---|---|---|---|---|---|---|---|---|---|
| APOE ε3/e4 | | | | | | | | | | | |
| rs1038025 | 50096812 | T/c | c | | 0.28 | 0.25 | 0.38 | 68 | 28 | 63 | 33 |
| rs1305062 | 50097361 | G/c | c | | 0.27 | 0.24 | 0.38 | 69 | 25 | 64 | 32 |
| rs34215622 | 50098378 | —/g | g | | 0.28 | 0.25 | 0.38 | 70 | 26 | 64 | 32 |
| rs34878901 | 50094317 | C/t | t | | 0.24 | 0.20 | 0.38 | 69 | 25 | 61 | 31 |
| rs8106922 | 50093506 | A/g | g | | 0.28 | 0.25 | 0.38 | 70 | 25 | 64 | 32 |

| SNP ID | LOAD (MM) | LOAD (Mm) | LOAD (mm) | Control (MM) | Control (Mm) | Control (mm) | OR | 95% CI lower | 95% CI upper |
|---|---|---|---|---|---|---|---|---|---|
| All ApoE genotypes | | | | | | | | | |
| rs1038025 | 40 | 27 | 7 | 11 | 17 | 3 | 0.66 | 0.35 | 1.23 |
| rs1038026 | 40 | 27 | 7 | 11 | 17 | 3 | 0.66 | 0.35 | 1.23 |
| rs1160985 | 40 | 27 | 7 | 11 | 17 | 3 | 0.65 | 0.34 | 1.19 |
| rs1305062 | 43 | 24 | 7 | 13 | 17 | 1 | 0.81 | 0.42 | 1.56 |
| rs34215622 | 42 | 26 | 6 | 12 | 17 | 2 | 0.66 | 0.35 | 1.25 |
| rs34878901 | 45 | 23 | 6 | 15 | 15 | 1 | 0.86 | 0.44 | 1.70 |
| rs7259620 | 41 | 26 | 7 | 11 | 17 | 3 | 0.63 | 0.33 | 1.18 |
| rs741780 | 40 | 27 | 7 | 11 | 17 | 3 | 0.65 | 0.34 | 1.19 |
| rs760136 | 40 | 27 | 7 | 11 | 17 | 3 | 0.65 | 0.34 | 1.19 |
| rs8106922 | 42 | 25 | 7 | 13 | 17 | 1 | 0.81 | 0.42 | 1.55 |
| APOE ε3/e4 | | | | | | | | | |
| rs1038025 | 22 | 24 | 2 | 17 | 29 | 2 | 0.79 | 0.43 | 1.45 |
| rs1305062 | 25 | 21 | 2 | 17 | 30 | 1 | 0.72 | 0.39 | 1.35 |
| rs34215622 | 24 | 22 | 2 | 17 | 30 | 1 | 0.74 | 0.40 | 1.38 |
| rs34878901 | 25 | 21 | 2 | 18 | 29 | 1 | 0.71 | 0.38 | 1.34 |
| rs8106922 | 25 | 21 | 2 | 17 | 30 | 1 | 0.71 | 0.38 | 1.33 |

Figure 8A:
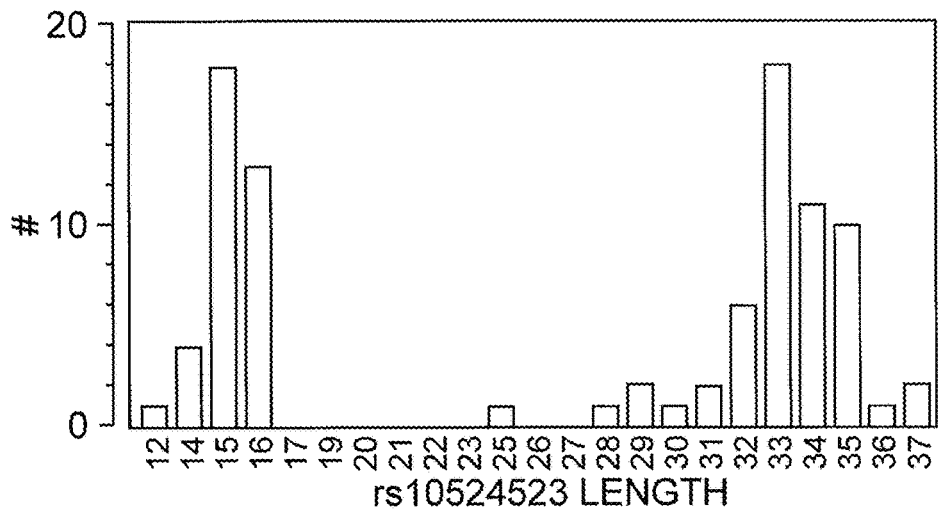
FIGS. 8A-8C present histograms of the length of the rs10524523 length polymorphism stratified by ApoE genotypes 3/3 (8A), 3/4 (8B), and 4/4 (8C). N=210 haplotypes (AS cohort).
Figure 8B:
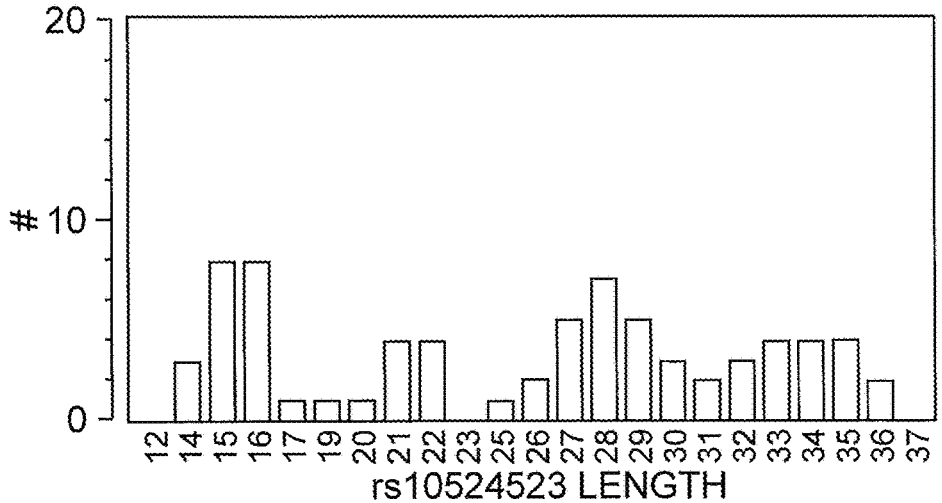
Figure 8C:
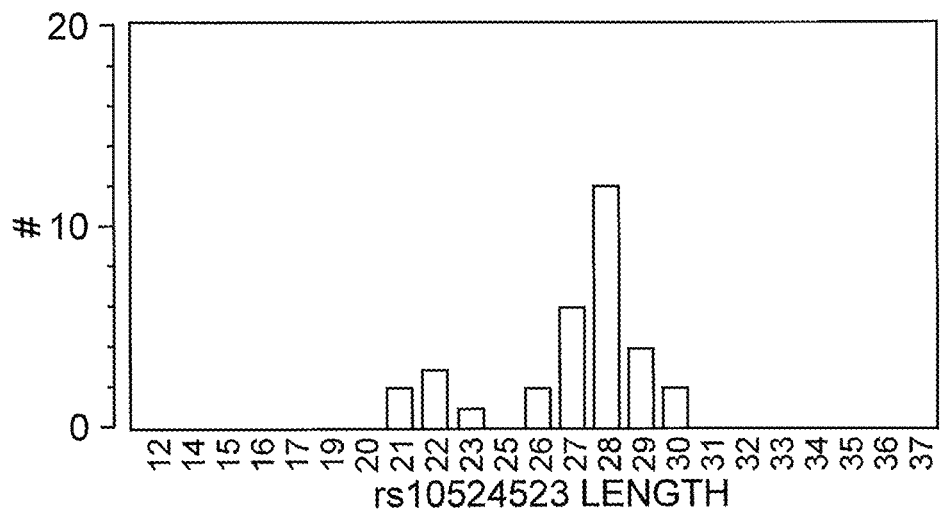
Figure 9:
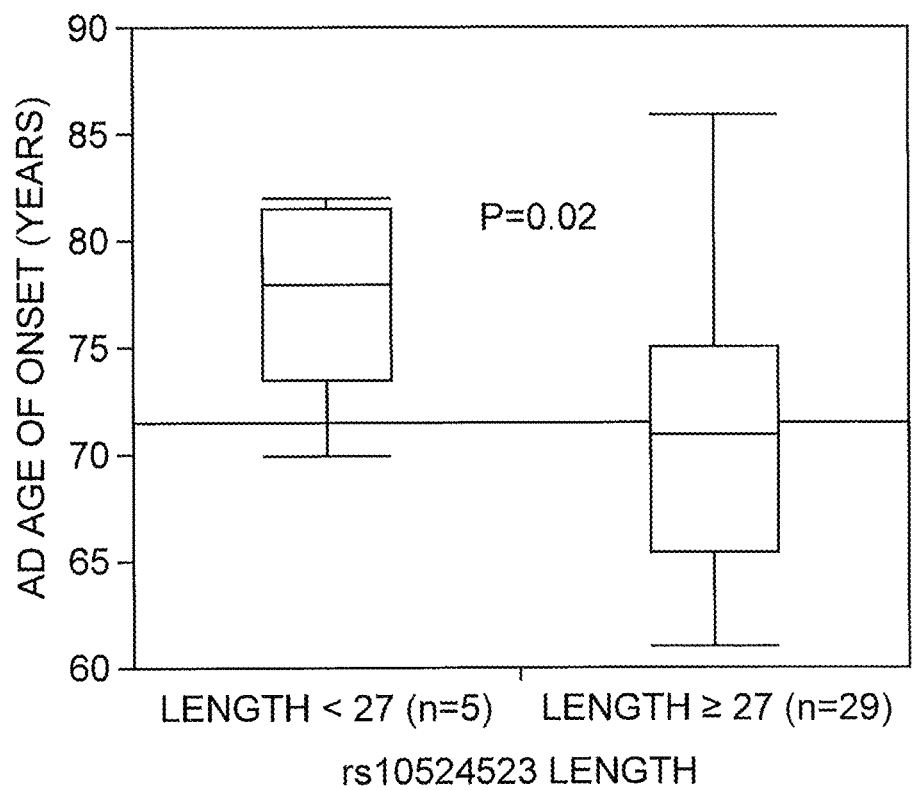
FIG. 9 shows the association between AD age of onset and length of the rs10524523 polymorphism for AD patients with the APOE3/4 genotype with onset between 60 and 86 years. Box plots indicate the 95% range (vertical lines), median (horizontal line in box) and interquartile range (box). "Length" refers to poly-T length of the rs10524523 allele that is inferred to be linked to APOE.
Figure 10:
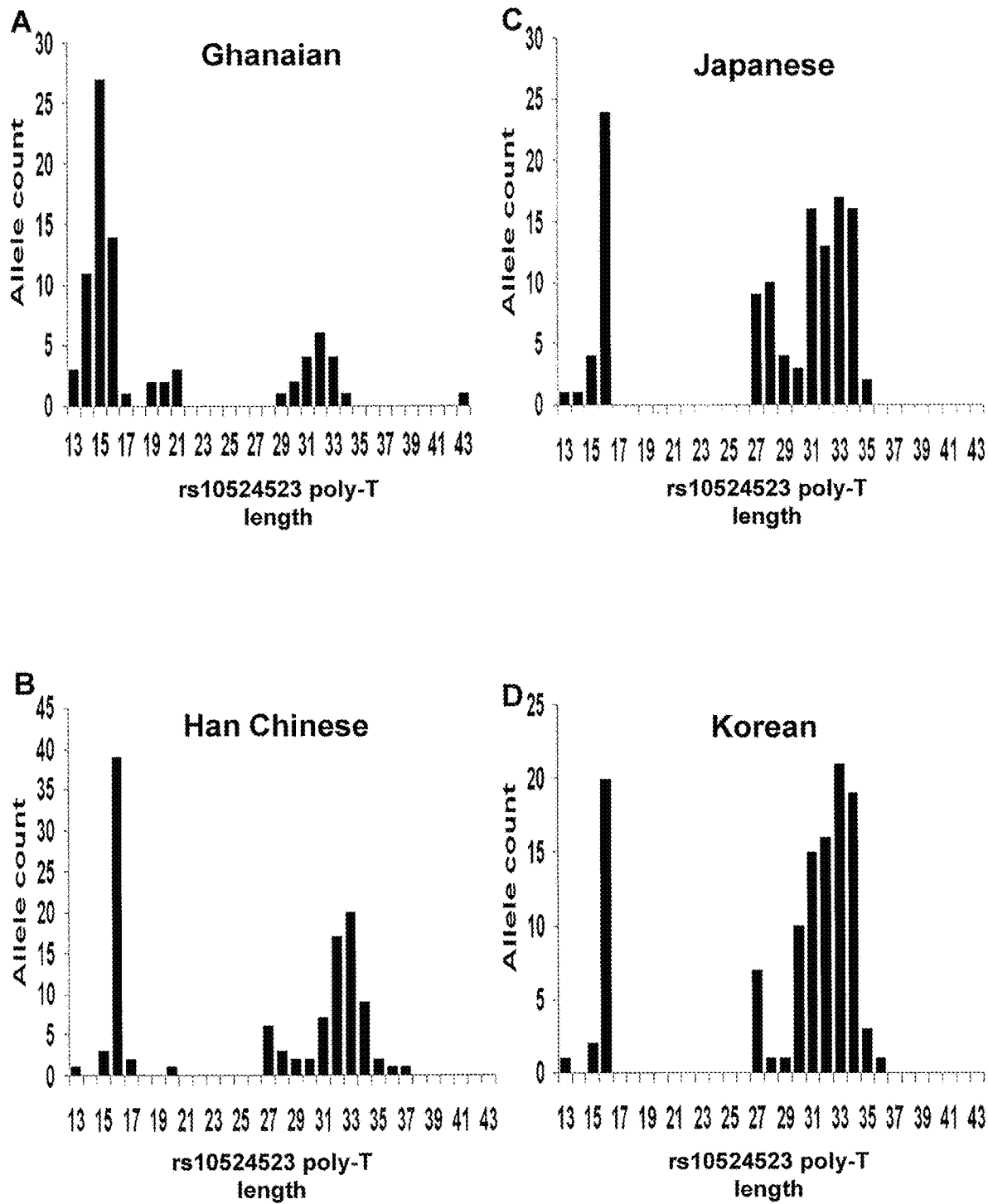
FIG. 10 shows the frequency distributions of the different rs10524523 length alleles in diverse populations, Ghanaian (A, n=41), Han Chinese, Japanese, Korean (B-D respectively, n=60 in each case). As with Caucasians, there are three peaks in the distribution of TOMM40 rs10524523 poly-T lengths in Japanese, Han Chinese, Korean (collectively Far Eastern) and Ghanaian populations. The frequency and mode of the distribution of the Ghanaian and Far Eastern populations are different from each other and different from Caucasians. Poly-T length is in number of deoxythymidine residues.

Another polymorphism that distinguished the two clades and, therefore, two groups of ApoE ε3 haplotypes, was a poly-T variant (r510524523) located in intron 6 of TOMM40. On ApoE ε4 chromosomes, the variant was relatively long, with a narrow, unimodal distribution of lengths (19–30 T residues, mean=26.78, s.d.=2.60, n=32), whereas on ApoE ε3 chromosomes, a bimodal distribution of lengths was evident with peaks at 15.17 (s.d.=0.85, n=36) and 33.15 (s.d.=2.09, n=55) T residues (FIGS. 8B and 8C). Longer poly-T lengths (T>=19) segregated almost exclusively into clade A, the higher risk clade, in the AS cohort (P=7.6×10$^{-46}$, n=210, Fisher's exact test, two-tailed). The case/control ratio for the category containing the two, most common, shorter lengths (15 or 16 T residues) was 1.46 (95% CI=1.25–1.75), and the case/control ratio for the longer length category (28, 29, 33 and 34 T residues) was 2.02 (95% CI=1.13–2.87). This data showed a trend to an association between the longer rs10524523 poly-T length and AD (OR=1.38, 95% CI=0.80–2.39).

While there were only trends toward association of TOMM40 haplotypes or individual polymorphisms with LOAD for the AS cohort, there was a significant association between poly-T length category of rs10524523 and age of LOAD onset. This was tested using the DS cohort of autopsy-confirmed ApoE ε3/ε4 subjects for whom there was disease onset data. Longer poly-T alleles (>=27 T residues) were significantly associated with onset of disease at a much younger age (70.5 years+/−1.2 versus 77.6 years+/−2.1, P=0.02, n=34) (FIG. 5).

This polymorphism, therefore, significantly impacted age of disease onset for individuals who carry an ApoE ε3 allele. Three other poly-T length polymorphisms located in intron 6 (rs34896370, rs56290633 and rs10602329) also distinguish clades A and B, but these polymorphisms were not associated with age of disease onset. Similarly, there was no relationship between haplotypes of clade-distinguishing SNPs and age of LOAD, or for the single SNP, rs8106922, which had been significantly associated with AD risk in three genome-wide association studies (Abraham et al. A genome-wide association study for late-onset Alzheimer's disease using DNA pooling. BMC Med Genomics 1, 44 (2008); Carrasquillo et al. Genetic variation in PCDH11X is associated with susceptibility to late-onset Alzheimer's disease. Nat Genet 41, 192-198 (2009); Takei et al. Genetic association study on in and around the ApoE in late-onset Alzheimer disease in Japanese. Genomics 93, 441-448 (2009)) (data not shown).

We conclude that longer poly-T tracts at rs10524523 are significantly correlated with earlier age of onset of LOAD. The length of this variant is relatively homogeneous, and relatively long, on APOE4 chromosomes, whereas there are two categories of poly-T lengths linked to APOE3. APOE2 chromosomes also appear to carry variable-length poly-T repeats similar to APOE3 chromosomes, and we anticipate the inheritance of the polyT with APOE2 will be similar to that of APOE3.

While it is possible that there are other variants that influence age of onset of LOAD for individuals who are not homozygous for APOE4, the length of the poly-T polymorphism in TOMM40 intron 6 appears to be the most powerful genetic predictor in this linkage region and should be validated prospectively. These data suggest that ApoE genotype-stratified age of onset curves (Corder et al. Gene dose of apolipoprotein E type 4 allele and the risk of Alzheimer's disease in late onset families. Science 261, 921-3 (1993); Li et al. Candidate single-nucleotide polymorphisms from a genomewide association study of Alzheimer disease. Arch Neurol 65, 45-53 (2008)) are, in reality, sets of curves with each curve reflecting a specific interaction of linked polymorphisms in ApoE and TOMM40. Therefore, these data add resolution to the prediction of age of LOAD onset, within a 5-7 year window, at least for individuals over 60 years of age, and likely for younger individuals. The study to validate the association of ApoE genotypes and TOMM40 haplotypes or rs10524523 with age of disease onset is currently being planned. This study will be a prospective, 5 year, population-based study conducted in several ethnic groups, and will be combined with a prevention or delay of disease onset drug trial.

Methods

The two cohorts analyzed in this study were from the Arizona Alzheimer's Disease Research Center (ADRC), Phoenix, Ariz. and the Duke Bryan ADRC, Durham, N.C. All subjects were of European descent. The Arizona and Duke studies were approved by institutional review boards and appropriate informed consent was obtained from all participants. Age and gender data for the cases and controls in each cohort are shown in Table 2. For the Duke cohort, the age of disease onset was determined retrospectively and disease diagnosis was confirmed by autopsy.

Samples were plated on 96 well plates for long-range PCR and DNA sequencing at Polymorphic DNA Technologies (Alameda, Calif.).

Long-range PCR was performed using Takara LA Taq Polymerase (Takara Minis Bio). The reaction mix and PCR conditions were the same as those recommended by the manufacturer. PCR was conducted in a 50 µL it volume with 2.5 U of LA Taq and 200-400 ng human genomic DNA. Thermocycling was carried out with the following conditions: 94° C., 1 min for 1 cycle; 94° C., 30 sec; 57° C., 30 sec; 68° C., 9 min for 14 cycles; 94° C., 30 sec; 57° C., 30 sec; 68° C., 9 min+15 sec/cycle for 16 cycles; 72° C., 10 min for 1 cycle. Primers for long-range PCR are shown in Table 4.

TABLE 4

Forward and reverse sequencing primers are listed. The shaded row indicates the forward and reverse primers used for long-range PCR of R2 (FIG. 2)

| Forward Primers | | | | Reverse Primers | | | |
|---|---|---|---|---|---|---|---|
| Sequence | UCSC Primer Coordinate (of 3' end of primer) | Primer Position in Cloned PCR Product (of 3' end of primer) | SEQ ID NO: | Sequence | UCSC Primer Coordinate (of 3' end of primer) | Primer Position in Cloned PCR Product (of 3' end of primer) | SEQ ID NO: |
| AACTCAGAGAGGCCAGAGATTCTAAGT | 50,092,429 | 25 | 1 | AACAGCCTAATCCCAGCACATTTAC | 50,101,560 | 9,156 | 2 |
| CAGGAAACAGCTATGAC | 50,092,292 | -112 | 3 | CCCACTGGTTGTTGA | 50,093,034 | 630 | 4 |
| GTGTGATGGTGATTCAAC | 50,093,038 | 634 | 5 | GAATAGGGGCCTTTCA | 50,093,282 | 878 | 6 |
| CTGCAGGTATGAAAG | 50,093,287 | 883 | 7 | CAATCTCCTAGGGTGC | 50,093,512 | 1108 | 8 |
| GTCTCTGCAGATGTG | 50,093,601 | 1197 | 9 | CGGAAGTTGCAGTAAG | 50,093,706 | 1302 | 10 |
| TACTGCAACTTCCGC | 50,093,722 | 1318 | 11 | AAGGTCAAGGTTACACT | 50,094,318 | 1914 | 12 |
| TCTCTGTTGCCACG | 50,094,289 | 1885 | 13 | ACAAGCCTAGTGACAT | 50,094,790 | 2386 | 14 |
| CCCAACTAATTTTTGTATTCG | 50,094,609 | 2205 | 15 | CCTGTAATCCCAGCTAT | 50,095,002 | 2598 | 16 |
| ACATTTGTGGCCTGTAC | 50,095,129 | 2725 | 17 | TCATCTCTGTGACCTAA | 50,095,324 | 2920 | 18 |
| CCACATGGGCTTGTGT | 50,095,603 | 3199 | 19 | GGCAAAATGACGATCAGT | 50,095,804 | 3400 | 20 |
| CCCAGATGCCCAAATC | 50,096,082 | 3678 | 21 | GCAGCACCAGCTAGT | 50,096,218 | 3814 | 22 |
| AACTCTGAGTGGATGTG | 50,096,471 | 4067 | 23 | GATGGTCTCAATCTCCTTA | 50,096,620 | 4216 | 24 |
| CTATAGTCCCAACTACTGA | 50,096,730 | 4326 | 25 | TTTTTTCCAAGCATAAAACATAGTA | 50,096,863 | 4459 | 26 |
| AGTCCCGCTACTTA | 50,097,080 | 4676 | 27 | GGGGATGGACAAAGCT | 50,097,268 | 4864 | 28 |
| ACCACAGGTGTATGCC | 50,097,451 | 5047 | 29 | TGAAAAGCCCTCTAGAC | 50,097,898 | 5494 | 30 |
| GAACAGATTCATCCCA | 50,097,864 | 5460 | 31 | CACCCACGATCCAGTT | 50,098,141 | 5737 | 32 |
| TGTGGATAGCAACTGGAT | 50,098,148 | 5744 | 33 | CAAAGCCACACTGAAACTT | 50,098,231 | 5827 | 34 |
| GGGATTCTGAGTAGCA | 50,098,469 | 6065 | 35 | CAGAATCCTGCGT | 50,098,526 | 6122 | 36 |
| TGCTGCCTTAAGTCCG | 50,098,937 | 6533 | 37 | ACACTTGAGAAAACGG | 50,098,797 | 6393 | 38 |
| CTGGGGTCAGCTGAT | 50,099,350 | 6946 | 39 | ACAAAGTCCTCTATAGCC | 50,099,077 | 6673 | 40 |

TABLE 4-continued

Forward and reverse sequencing primers are listed. The shaded row indicates the forward and reverse primers used for long-range PCR of R2 (FIG. 2)

| Forward Primers | | | | Reverse Primers | | | |
|---|---|---|---|---|---|---|---|
| Sequence | UCSC Primer Coordinate (of 3' end of primer) | Primer Position in Cloned PCR Product (of 3' end of primer) | SEQ ID NO: | Sequence | UCSC Primer Coordinate (of 3' end of primer) | Primer Position in Cloned PCR Product (of 3' end of primer) | SEQ ID NO: |
| TGAAACATCTGGGATTTATAAC | 50,099,679 | 7275 | 41 | TAACCTGGGGTTGGTT | 50,099,429 | 7025 | 42 |
| CTGGAAACCACAATACC | 50,099,990 | 7586 | 43 | AAGTTCCTTTGCTCATCAG | 50,099,829 | 7425 | 44 |
| ATCTCGGCTCACTGTA | 50,100,261 | 7857 | 45 | GCAAGAGGGAGACTGT | 50,100,207 | 7803 | 46 |
| GTCAAAAGACCTCTATGC | 50,100,739 | 8335 | 47 | TGTGCCTGGATGAATGTA | 50,100,567 | 8163 | 48 |
| AGGACTCCACGAGT | 50,101,197 | 8793 | 49 | TGAGCTTCATCCCCGT | 50,100,960 | 8556 | 50 |
| | | | | CCGTGTTCCATTTATGAG | 50,101,328 | 8924 | 51 |
| | | | | GTAAAACGACGGCCAG | 50,101,681 | 9277 | 52 |

PCR products were run on a 0.8% agarose gel, visualized by crystal violet dye, compared to size standards, cut out of the gel, and extracted with purification materials included with the TOPO XL PCR Cloning kit (Invitrogen). Long-range PCR products were cloned into a TOPO XL PCR cloning vector. This system uses a TA cloning vector and is recommended for inserts of up to 10 kb. Per the manufacturer's instructions, electro-competent cells (from the same kit) were transformed by the vector, plated in the presence of antibiotic, and incubated. Ten clones from each plate were picked and cultured in a 96-well format.

Diluted cultures were transferred to a denaturing buffer that was part of the TempliPhi DNA Sequencing Template Amplification kit (GE HealthCare/Amersham Biosciences). This buffer causes the release of plasmid DNA but not bacterial DNA. Cultures were heated, cooled, spun, and transferred to fresh plates containing the TempliPhi enzyme and other components. This mixture was incubated at 30° C. for 18 hours to promote amplification of the plasmid templates. These products were then spun and heated to 65° C. to destroy the enzyme.

Plasmid templates were used in DNA sequencing reactions using the Big Dye, version 3.1 sequencing kit (Applied Biosystems). For each reaction, an appropriate sequencing primer (Table 4) was used that was designed to anneal to a unique location of the template. Cycle sequencing was carried out with an annealing temperature of 50° C., an elongation temperature of 60° C., and a denaturation temperature of 96° C., for a total of 30 cycles. Sequencing reaction products were run on an ABI 3730XL DNA sequencer with a 50 cm capillary array using standard run mode.

A proprietary sequencing analysis program called 'Agent' (developed by Celera) was used to align sequencing reads to the appropriate reference sequence, and produce 'contigs' associated with each clone. The system provides estimated quality scores for all bases for which there is any variation for any of the samples. The sequencing report for each sample was analyzed for the presence of SNPs that were correlated in one haplotype pattern for one subset of clones and in a different haplotype pattern for the remaining clones. A reference file for the region of interest was prepared by listing the known variations for that region publicly available from NCBI dbSNP. A genotype file for the region of interest was created by searching each subject's haplotype report for all variations between the known reference sequence and the consensus haplotype sequences.

The magnitude of the length-reading error for the poly-T variants (e.g., rs10524523) was estimated by examining the observed lengths from the 10 clones that were prepared for samples that had a single haplotype. For a typical sample with short poly-T length of 16, the standard deviation for the 10 clones was 0.97. For a typical sample with longer poly-T length, e.g., 27, the standard deviation was 1.58.

Phylogenetic analysis was conducted. A multiple sequence alignment of the sequences was performed using the ClustalW2 (version 2.0.10) program using default parameters. Manual adjustment of the alignments was completed using Genedoc (version 2.7.000). Phylogenetic trees were constructed using Bayesian, maximum likelihood and distance-based reconstructions. The phylogenetic tree construction software used was Paup* (version 4.0b10), ClustalX2 (neighbor-joining methods, version 2.0.10) and Mr. Bayes (version 3.1.2).

Tree-bisection and reconnection branch swapping were used in all methods. The best fitting model of sequence evolution was estimated using the Modeltest program (version 3.7) which provided estimates for the following key determinants: rate matrix, shape of the gamma distribution and proportion of invariant sites. Bootstrap analysis was performed using 1000 replicates to determine statistical support for specific tree morphology.

Haplotype networks were also constructed from the sequence data using the program TCS (version 1.21 (Clement et al. TCS: a computer program to estimate gene genealogies. *Mol Ecol* 9, 1657-9 (2000))) to compare the phylogenetic trees to cladograms estimated using statistical parsimony. The phylogenetic trees and haplotype networks were constructed twice, with gaps treated as missing data for the first instance and as a fifth character for the second instance. Nucleotide diversity in the region of interest was calculated using DnaSP (version 5.00.02 (Librado et al. DnaSP v5: a software for comprehensive analysis of DNA polymorphism data. *Bioinformatics* 25, 1451-2 (2009))).

After construction of the phylogenetic trees, the haplotype network, and completion of the analysis of nucleotide diversity in the region of interest, the results from the different methods were compared and reconciled to a consensus tree. Groups of sequences sharing a recent disease mutation were presumed to segregate more closely on the phylogenetic tree, however, sporadic cases due to phenocopies, dominance and epistasis can introduce noise into the phenotype-haplotype relationship (Tachmazidou et al. Genetic association mapping via evolution-based clustering of haplotypes. *PLoS Genet* 3, e111 (2007)).

However, sporadic cases due to phenocopies, dominance and epistasis can introduce noise into the phenotype-haplotype relationship. This phylogenetic analysis focused on a high-level aggregation of clades in order to minimize these effects. The clades determined at the first split in the phylogenetic tree were used to test the hypothesis that TOMM40 subject-haplotypes from clade 'B' were associated with onset of AD at a later age than subject-haplotypes from clade 'A', (each subject contributed two haplotypes to the AD age of onset association signal). The number of tests of association that are performed using this approach was orders of magnitude less than in typical genomewide association studies since the phylogenetic analysis identified categories of evolutionarily-related subject-haplotypes. If the tests of association confirmed that the different clades classified the subject-haplotype data by age of onset, further statistical analysis was done to identify the variants that separated the sequences into each clade. Effectively, this analysis assessed the significance of each variant as a factor that influences age of onset using a series of one-degree of freedom tests guided by the tree structure. The phylogenetic analyses were conducted using single nucleotide and insertion/deletion polymorphisms. The statistical tests of association were adjusted with a Bonferroni correction for the number of polymorphic sites included in the analysis.

Haplotype reports from the Polymorphic analysis software and reports from DnaSP software (version 5.00.02 (Librado et al. DnaSP v5: a software for comprehensive analysis of DNA polymorphism data. *Bioinformatics* 25, 1451-2 (2009))) were used for subsequent statistical analyses. We analyzed individual TOMM40 SNP variants, TOMM40 haplotypes and length of poly-T repeats for association with LOAD risk for the AS cohort and LOAD age of onset for the DS cohort. Differences in the proportions of specific TOMM40 alleles associated with each ApoE allele or ApoE genotype were compared using Fisher's exact test (two-tailed). Starting with 30 parsimony-informative sites and α=0.05, a Bonferroni correction for the significance of a specific allelic association would require a P value of 0.001. Odds ratios (OR) were calculated as the (number of minor alleles in cases/number of minor alleles in controls)/(number of major alleles in cases/number of major alleles in controls) and reported with 95% confidence interval. Means for defined LOAD age of onset groups were compared by t tests, two-tailed. A standard F test on group variances was performed to determine whether the t test was calculated assuming equal or unequal variances. Statistical analysis was completed using JMP software (version 8, SAS Institute, Cary, N.C.).

Accession Codes: GenBank: TOMM40, translocase of outer mitochondrial membrane 40 homolog, 10452; ApoE, apolipoprotein E, 348

The foregoing is illustrative of the present invention, and is not to be construed as limiting thereof. The invention is defined by the following claims, with equivalents of the claims to be included therein.

That which is claimed is:

1. An in vitro method of detecting a deletion/insertion polymorphism (DIP) located in intron 6 of the TOMM40 gene, comprising detecting from a biological sample containing DNA from a human subject a poly-T length of 19, 20, 21, 22, 23, 26, 27, 28, 29, 30 or 31 T residues at rs10524523 of the TOMM40 gene.

2. The method of claim 1, said method further comprising detecting from the biological sample the presence or absence of an Apo E2, E3, or E4 allele.

3. The method of claim 1, said method further comprising detecting from the biological sample the presence of an Apo E2/E2, E2/E3, E2/E4, E3/E3, E3/E4, or E4/E4 genotype.

4. The method of claim 1, wherein said DIP has a poly-T length of 21, 22, 27, 28, 29, 30 or 31 T residues.

5. The method of claim 1, wherein said detecting comprises DNA sequencing.

6. The method of claim 1, wherein said detecting comprises PCR amplification.

7. The method of claim 1, wherein said detecting comprises electrophoresis.

8. The method of claim 1, wherein said detecting comprises determining the poly-T length at each rs10524523 allele.

9. The method of claim 8, further comprising detecting from the biological sample the presence of an Apo E2/E2, E2/E3, E2/E4, E3/E3, E3/E4, or E4/E4 genotype.

10. The method of claim 8, further comprising detecting from the biological sample the presence of an Apo E3/E3 or E3/E4 genotype.

* * * * *

SEQUENCE LISTING

```
<160> NUMBER OF SEQ ID NOS: 52

<210> SEQ ID NO 1
<211> LENGTH: 25
<212> TYPE: DNA
<213> ORGANISM: Artificial
<220> FEATURE:
<223> OTHER INFORMATION: Long range PCR primer

<400> SEQUENCE: 1
aactcagagg ccagagattc taagt                                25

<210> SEQ ID NO 2
<211> LENGTH: 25
<212> TYPE: DNA
<213> ORGANISM: Artificial
<220> FEATURE:
<223> OTHER INFORMATION: Long range PCR primer

<400> SEQUENCE: 2
aacagcctaa tcccagcaca tttac                                25

<210> SEQ ID NO 3
<211> LENGTH: 17
<212> TYPE: DNA
<213> ORGANISM: Artificial
<220> FEATURE:
<223> OTHER INFORMATION: Sequencing primer

<400> SEQUENCE: 3
caggaaacag ctatgac                                         17

<210> SEQ ID NO 4
<211> LENGTH: 15
<212> TYPE: DNA
<213> ORGANISM: Artificial
<220> FEATURE:
<223> OTHER INFORMATION: Sequencing primer

<400> SEQUENCE: 4
cccactggtt gttga                                           15

<210> SEQ ID NO 5
<211> LENGTH: 18
<212> TYPE: DNA
<213> ORGANISM: Artificial
<220> FEATURE:
<223> OTHER INFORMATION: Sequencing primer

<400> SEQUENCE: 5
gtgtgatggt gattcaac                                        18

<210> SEQ ID NO 6
```

<211> LENGTH: 16
<212> TYPE: DNA
<213> ORGANISM: Artificial
<220> FEATURE:
<223> OTHER INFORMATION: Sequencing primer

<400> SEQUENCE: 6 gaatagggc ctttca                                                    16

<210> SEQ ID NO 7
<211> LENGTH: 15
<212> TYPE: DNA
<213> ORGANISM: Artificial
<220> FEATURE:
<223> OTHER INFORMATION: Sequencing primer

<400> SEQUENCE: 7
ctgcaggtat gaaag                                                    15

<210> SEQ ID NO 8
<211> LENGTH: 16
<212> TYPE: DNA
<213> ORGANISM: Artificial
<220> FEATURE:
<223> OTHER INFORMATION: Sequencing primer

<400> SEQUENCE: 8
caatctccta gggtgc                                                   16

<210> SEQ ID NO 9
<211> LENGTH: 15
<212> TYPE: DNA
<213> ORGANISM: Artificial
<220> FEATURE:
<223> OTHER INFORMATION: Sequencing primer

<400> SEQUENCE: 9
gtctctgcag atgtg                                                    15

<210> SEQ ID NO 10
<211> LENGTH: 16
<212> TYPE: DNA
<213> ORGANISM: Artificial
<220> FEATURE:
<223> OTHER INFORMATION: Sequencing primer

<400> SEQUENCE: 10
cggaagttgc agtaag                                                   16

<210> SEQ ID NO 11
<211> LENGTH: 15
<212> TYPE: DNA
<213> ORGANISM: Artificial
<220> FEATURE:
<223> OTHER INFORMATION: Sequencing primer

<400> SEQUENCE: 11
tactgcaact tccgc                                                    15

<210> SEQ ID NO 12
<211> LENGTH: 17
<212> TYPE: DNA
<213> ORGANISM: Artificial
<220> FEATURE:
<223> OTHER INFORMATION: Sequencing primer

<400> SEQUENCE: 12
aaggtcaagg ttacact                                              17

<210> SEQ ID NO 13
<211> LENGTH: 15
<212> TYPE: DNA
<213> ORGANISM: Artificial
<220> FEATURE:
<223> OTHER INFORMATION: Sequencing primer

<400> SEQUENCE: 13
tctctgttgc ccacg                                                15

<210> SEQ ID NO 14
<211> LENGTH: 17
<212> TYPE: DNA
<213> ORGANISM: Artificial
<220> FEATURE:
<223> OTHER INFORMATION: Sequencing primer

<400> SEQUENCE: 14
acaagcctag gtgacat                                              17

<210> SEQ ID NO 15
<211> LENGTH: 21
<212> TYPE: DNA
<213> ORGANISM: Artificial
<220> FEATURE:
<223> OTHER INFORMATION: Sequencing primer

<400> SEQUENCE: 15
cccaactaat ttttgtattc g                                         21

<210> SEQ ID NO 16
<211> LENGTH: 17
<212> TYPE: DNA
<213> ORGANISM: Artificial
<220> FEATURE:
<223> OTHER INFORMATION: Sequencing primer

<400> SEQUENCE: 16
cctgtaatcc cagctat                                              17

<210> SEQ ID NO 17
<211> LENGTH: 17
<212> TYPE: DNA
<213> ORGANISM: Artificial
<220> FEATURE:
<223> OTHER INFORMATION: Sequencing primer

<400> SEQUENCE: 17
acatttgtgg cctgtac                                              17

<210> SEQ ID NO 18
<211> LENGTH: 20
<212> TYPE: DNA
<213> ORGANISM: Artificial
<220> FEATURE:
<223> OTHER INFORMATION: Sequencing primer

<400> SEQUENCE: 18
tcatctctct gtgaacctaa                                           20

<210> SEQ ID NO 19
<211> LENGTH: 16
<212> TYPE: DNA

```
<213> ORGANISM: Artificial
<220> FEATURE:
<223> OTHER INFORMATION: Sequencing primer

<400> SEQUENCE: 19
ccacatgggc ttgtgt                                                    16

<210> SEQ ID NO 20
<211> LENGTH: 18
<212> TYPE: DNA
<213> ORGANISM: Artificial
<220> FEATURE:
<223> OTHER INFORMATION: Sequencing primer

<400> SEQUENCE: 20
ggcaaaatga cgatcagt                                                  18

<210> SEQ ID NO 21
<211> LENGTH: 16
<212> TYPE: DNA
<213> ORGANISM: Artificial
<220> FEATURE:
<223> OTHER INFORMATION: Sequencing primer

<400> SEQUENCE: 21
cccagatgcc caaatc                                                    16

<210> SEQ ID NO 22
<211> LENGTH: 15
<212> TYPE: DNA
<213> ORGANISM: Artificial
<220> FEATURE:
<223> OTHER INFORMATION: Sequencing primer

<400> SEQUENCE: 22
gcagcaccag ctagt                                                     15

<210> SEQ ID NO 23
<211> LENGTH: 17
<212> TYPE: DNA
<213> ORGANISM: Artificial
<220> FEATURE:
<223> OTHER INFORMATION: Sequencing primer

<400> SEQUENCE: 23
aactctgagt ggatgtg                                                   17

<210> SEQ ID NO 24
<211> LENGTH: 19
<212> TYPE: DNA
<213> ORGANISM: Artificial
<220> FEATURE:
<223> OTHER INFORMATION: Sequencing primer

<400> SEQUENCE: 24
gatggtctca atctcctta                                                 19

<210> SEQ ID NO 25
<211> LENGTH: 19
<212> TYPE: DNA
<213> ORGANISM: Artificial
<220> FEATURE:
<223> OTHER INFORMATION: Sequencing primer

<400> SEQUENCE: 25
ctatagtccc aactactga                                                 19
```

```
<210> SEQ ID NO 26
<211> LENGTH: 25
<212> TYPE: DNA
<213> ORGANISM: Artificial
<220> FEATURE:
<223> OTHER INFORMATION: Sequencing primer

<400> SEQUENCE: 26 tttttccaa gcataaaaca tagta                                        25

<210> SEQ ID NO 27
<211> LENGTH: 15
<212> TYPE: DNA
<213> ORGANISM: Artificial
<220> FEATURE:
<223> OTHER INFORMATION: Sequencing primer

<400> SEQUENCE: 27
agtccccgct actta                                                  15

<210> SEQ ID NO 28
<211> LENGTH: 16
<212> TYPE: DNA
<213> ORGANISM: Artificial
<220> FEATURE:
<223> OTHER INFORMATION: Sequencing primer

<400> SEQUENCE: 28
ggggatggac aaagct                                                 16

<210> SEQ ID NO 29
<211> LENGTH: 16
<212> TYPE: DNA
<213> ORGANISM: Artificial
<220> FEATURE:
<223> OTHER INFORMATION: Sequencing primer

<400> SEQUENCE: 29
accacaggtg tatgcc                                                 16

<210> SEQ ID NO 30
<211> LENGTH: 17
<212> TYPE: DNA
<213> ORGANISM: Artificial
<220> FEATURE:
<223> OTHER INFORMATION: Sequencing primer

<400> SEQUENCE: 30
tgaaaagccc tctagac                                                17

<210> SEQ ID NO 31
<211> LENGTH: 17
<212> TYPE: DNA
<213> ORGANISM: Artificial
<220> FEATURE:
<223> OTHER INFORMATION: Sequencing primer

<400> SEQUENCE: 31
gaacagattc atccgca                                                17

<210> SEQ ID NO 32
<211> LENGTH: 16
<212> TYPE: DNA
<213> ORGANISM: Artificial
<220> FEATURE:
```

-continued

<223> OTHER INFORMATION: Sequencing primer

<400> SEQUENCE: 32
cacccacgat ccagtt                                                          16

<210> SEQ ID NO 33
<211> LENGTH: 18
<212> TYPE: DNA
<213> ORGANISM: Artificial
<220> FEATURE:
<223> OTHER INFORMATION: Sequencing primer

<400> SEQUENCE: 33
tgtggatagc aactggat                                                        18

<210> SEQ ID NO 34
<211> LENGTH: 19
<212> TYPE: DNA
<213> ORGANISM: Artificial
<220> FEATURE:
<223> OTHER INFORMATION: Sequencing primer

<400> SEQUENCE: 34
caaagccaca ctgaaactt                                                       19

<210> SEQ ID NO 35
<211> LENGTH: 16
<212> TYPE: DNA
<213> ORGANISM: Artificial
<220> FEATURE:
<223> OTHER INFORMATION: Sequencing primer

<400> SEQUENCE: 35
gggattctga gtagca                                                          16

<210> SEQ ID NO 36
<211> LENGTH: 13
<212> TYPE: DNA
<213> ORGANISM: Artificial
<220> FEATURE:
<223> OTHER INFORMATION: Sequencing primer

<400> SEQUENCE: 36
cagaatcctg cgt                                                             13

<210> SEQ ID NO 37
<211> LENGTH: 16
<212> TYPE: DNA
<213> ORGANISM: Artificial
<220> FEATURE:
<223> OTHER INFORMATION: Sequencing primer

<400> SEQUENCE: 37
tgctgcctta agtccg                                                          16

<210> SEQ ID NO 38
<211> LENGTH: 16
<212> TYPE: DNA
<213> ORGANISM: Artificial
<220> FEATURE:
<223> OTHER INFORMATION: Sequencing primer

<400> SEQUENCE: 38
acacttgaga aaacgg                                                          16

```
<210> SEQ ID NO 39
<211> LENGTH: 15
<212> TYPE: DNA
<213> ORGANISM: Artificial
<220> FEATURE:
<223> OTHER INFORMATION: Sequencing primer

<400> SEQUENCE: 39
ctggggtcag ctgat                                                        15

<210> SEQ ID NO 40
<211> LENGTH: 18
<212> TYPE: DNA
<213> ORGANISM: Artificial
<220> FEATURE:
<223> OTHER INFORMATION: Sequencing primer

<400> SEQUENCE: 40
acaaagtcct ctatagcc                                                     18

<210> SEQ ID NO 41
<211> LENGTH: 22
<212> TYPE: DNA
<213> ORGANISM: Artificial
<220> FEATURE:
<223> OTHER INFORMATION: Sequencing primer

<400> SEQUENCE: 41
tgaaacatct gggatttata ac                                                22

<210> SEQ ID NO 42
<211> LENGTH: 16
<212> TYPE: DNA
<213> ORGANISM: Artificial
<220> FEATURE:
<223> OTHER INFORMATION: Sequencing primer

<400> SEQUENCE: 42
taacctgggg ttggtt                                                       16

<210> SEQ ID NO 43
<211> LENGTH: 17
<212> TYPE: DNA
<213> ORGANISM: Artificial
<220> FEATURE:
<223> OTHER INFORMATION: Sequencing primer

<400> SEQUENCE: 43
ctggaaacca caatacc                                                      17

<210> SEQ ID NO 44
<211> LENGTH: 19
<212> TYPE: DNA
<213> ORGANISM: Artificial
<220> FEATURE:
<223> OTHER INFORMATION: Sequencing primer

<400> SEQUENCE: 44
aagttccttt gctcatcag                                                    19

<210> SEQ ID NO 45
<211> LENGTH: 16
<212> TYPE: DNA
<213> ORGANISM: Artificial
<220> FEATURE:
<223> OTHER INFORMATION: Sequencing primer
```

```
<400> SEQUENCE: 45
atctcggctc actgta                                                       16

<210> SEQ ID NO 46
<211> LENGTH: 16
<212> TYPE: DNA
<213> ORGANISM: Artificial
<220> FEATURE:
<223> OTHER INFORMATION: Sequencing primer

<400> SEQUENCE: 46
gcaagaggga gactgt                                                       16

<210> SEQ ID NO 47
<211> LENGTH: 18
<212> TYPE: DNA
<213> ORGANISM: Artificial
<220> FEATURE:
<223> OTHER INFORMATION: Sequencing primer

<400> SEQUENCE: 47
gtcaaaagac ctctatgc                                                     18

<210> SEQ ID NO 48
<211> LENGTH: 18
<212> TYPE: DNA
<213> ORGANISM: Artificial
<220> FEATURE:
<223> OTHER INFORMATION: Sequencing primer

<400> SEQUENCE: 48
tgtgcctgga tgaatgta                                                     18

<210> SEQ ID NO 49
<211> LENGTH: 14
<212> TYPE: DNA
<213> ORGANISM: Artificial
<220> FEATURE:
<223> OTHER INFORMATION: Sequencing primer

<400> SEQUENCE: 49
aggactccac gagt                                                         14

<210> SEQ ID NO 50
<211> LENGTH: 15
<212> TYPE: DNA
<213> ORGANISM: Artificial
<220> FEATURE:
<223> OTHER INFORMATION: Sequencing primer

<400> SEQUENCE: 50
tgagctcatc cccgt                                                        15

<210> SEQ ID NO 51
<211> LENGTH: 18
<212> TYPE: DNA
<213> ORGANISM: Artificial
<220> FEATURE:
<223> OTHER INFORMATION: Sequencing primer

<400> SEQUENCE: 51
ccgtgttcca tttatgag                                                     18

<210> SEQ ID NO 52
<211> LENGTH: 16
```

```
<212> TYPE: DNA
<213> ORGANISM: Artificial
<220> FEATURE:
<223> OTHER INFORMATION: Sequencing primer

<400> SEQUENCE: 52
gtaaaacgac ggccag                                                        16
```